United States Patent
Kori et al.

(10) Patent No.: US 11,500,292 B2
(45) Date of Patent: Nov. 15, 2022

(54) MATERIAL FOR FORMING ORGANIC FILM, SUBSTRATE FOR MANUFACTURING SEMICONDUCTOR DEVICE, METHOD FOR FORMING ORGANIC FILM, PATTERNING PROCESS, AND COMPOUND FOR FORMING ORGANIC FILM

(71) Applicant: SHIN-ETSU CHEMICAL CO., LTD., Tokyo (JP)

(72) Inventors: Daisuke Kori, Joetsu (JP); Keisuke Niida, Joetsu (JP); Takashi Sawamura, Joetsu (JP); Seiichiro Tachibana, Joetsu (JP); Takeru Watanabe, Joetsu (JP); Tsutomu Ogihara, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 193 days.

(21) Appl. No.: 16/850,094

(22) Filed: Apr. 16, 2020

(65) Prior Publication Data

US 2020/0333709 A1    Oct. 22, 2020

(30) Foreign Application Priority Data

Apr. 16, 2019 (JP) ................ JP2019-78082

(51) Int. Cl.
  *G03F 7/09*    (2006.01)
  *H01L 21/02*   (2006.01)
  (Continued)

(52) U.S. Cl.
  CPC ............ *G03F 7/094* (2013.01); *C07C 43/215* (2013.01); *C07C 235/84* (2013.01);
  (Continued)

(58) Field of Classification Search
  CPC . C08L 101/02; G03F 7/11; G03F 7/26; G03F 7/36; G03F 7/075; G03F 7/30;
  (Continued)

(56) References Cited

U.S. PATENT DOCUMENTS 4,276,407 A   6/1981   Bilow et al.
4,303,775 A   12/1981  Chow et al.
(Continued)

FOREIGN PATENT DOCUMENTS

CN    101423610 A    5/2009
CN    101775138 A    7/2010
(Continued)

OTHER PUBLICATIONS

Hirose, JP 2005-272483, English Machine Translation (Year: 2005).*
(Continued)

*Primary Examiner* — Caleen O Sullivan
(74) *Attorney, Agent, or Firm* — Oliff PLC

(57) ABSTRACT

An object of the present invention is to provide: a compound containing an imide group which is not only cured under film formation conditions of inert gas as well as air and has excellent heat resistance and properties of filling and planarizing a pattern formed on a substrate, but can also form an organic underlayer film with favorable adhesion to a substrate, and a material for forming an organic film containing the compound. A material for forming an organic film, including: (A) a compound for forming an organic film shown by the following general formula (1A); and (B) an organic solvent, $$W_1 \!\!-\!\!(X_1)_{n1} \tag{1A}$$

(Continued)

-continued (1B) X1 = [N-phthalimide with R₁ substituent]

(1C) X1 = [N-H amide with R₂O-C(=O) and R₁ on benzene ring]

(1D) R₁ = —≡ , —≡—CH₃ , —≡—[phenyl] , —C≡N noting that in the general formula (1B), when W₁ represents W₁ = [phenyl-O-phenyl-C(CH₃)₂-phenyl-O-phenyl]

R₁ does not represent any of

R₁ = —≡ , —≡—CH₃ , —C≡N.

25 Claims, 3 Drawing Sheets

(51) Int. Cl.

| | | |
|---|---|---|
| H01L 21/3105 | (2006.01) | |
| H01L 21/027 | (2006.01) | |
| H01L 21/033 | (2006.01) | |
| G03F 7/16 | (2006.01) | |
| C07C 235/84 | (2006.01) | |
| C07D 403/14 | (2006.01) | |
| C07C 43/215 | (2006.01) | |
| C07D 207/448 | (2006.01) | |
| C08G 73/06 | (2006.01) | |
| G03F 7/20 | (2006.01) | |
| G03F 7/38 | (2006.01) | |
| G03F 7/32 | (2006.01) | |
| C07D 209/48 | (2006.01) | |
| G03F 7/027 | (2006.01) | |

(52) U.S. Cl.
CPC ....... *C07D 207/448* (2013.01); *C07D 209/48* (2013.01); *C07D 403/14* (2013.01); *C08G 73/0672* (2013.01); *G03F 7/027* (2013.01); *G03F 7/091* (2013.01); *G03F 7/162* (2013.01); *G03F 7/168* (2013.01); *G03F 7/2006* (2013.01); *G03F 7/2041* (2013.01); *G03F 7/322* (2013.01); *G03F 7/38* (2013.01); *H01L 21/0276* (2013.01); *H01L 21/02118* (2013.01); *H01L 21/02282* (2013.01); *H01L 21/0332* (2013.01); *H01L 21/0335* (2013.01); *H01L 21/0337* (2013.01); *H01L 21/0338* (2013.01); *H01L 21/31058* (2013.01); *C07C 2603/18* (2017.05)

(58) Field of Classification Search
CPC .......... G03F 7/094; G03F 7/027; G03F 7/091; G03F 7/162; G03F 7/168; G03F 7/2006; G03F 7/2041; G03F 7/322; G03F 7/38; H01L 21/0271; H01L 21/31144; H01L 21/32139; H01L 21/02118; H01L 21/02282; H01L 21/0276; H01L 21/0332; H01L 21/0335; H01L 21/0337; H01L 21/0338; H01L 21/31058; C07C 2603/18; C07C 233/75; C07C 233/80; C07C 39/17; C07C 43/215; C07C 235/84; C08G 73/1017; C08G 73/1032; C08G 73/1067; C08G 73/124; C08G 73/1014; C08G 73/0672; C08F 38/00; C08F 220/24; C08F 220/283; C08F 22/40; C09D 179/08; C07D 207/448; C07D 209/48; C07D 403/14
USPC .................. 438/700; 430/270.1, 271.1, 272.1
See application file for complete search history.

(56) References Cited

U.S. PATENT DOCUMENTS

| | | |
|---|---|---|
| 4,649,189 A | 3/1987 | Achar et al. |
| 4,952,666 A | 8/1990 | Landis |
| 5,108,840 A | 4/1992 | Mercer |
| 2002/0106909 A1 | 8/2002 | Kato et al. |
| 2004/0006196 A1 | 1/2004 | Scola et al. |
| 2005/0255712 A1 | 11/2005 | Kato et al. |
| 2006/0019195 A1 | 1/2006 | Hatakeyama et al. |
| 2006/0204891 A1 | 9/2006 | Hatakeyama |
| 2009/0082368 A1 | 3/2009 | Vohra et al. |
| 2009/0274978 A1 | 11/2009 | Ohashi et al. |
| 2010/0099044 A1 | 4/2010 | Hatakeyama et al. |
| 2012/0252217 A1 | 10/2012 | Minegishi et al. |
| 2013/0302990 A1 | 11/2013 | Watanabe et al. |
| 2016/0085152 A1 | 3/2016 | Nakafuji et al. |
| 2016/0215132 A1 | 7/2016 | Zheng et al. |
| 2017/0184968 A1 | 6/2017 | Kori et al. |
| 2018/0024434 A1 | 1/2018 | Takemura et al. |
| 2018/0120702 A1 | 5/2018 | Urano et al. |
| 2019/0067021 A1 | 2/2019 | Kori et al. |

FOREIGN PATENT DOCUMENTS

| | | |
|---|---|---|
| CN | 101985498 A | 3/2011 |
| CN | 104130177 A | 11/2014 |
| CN | 105504282 A | 4/2016 |
| CN | 105778090 A | 7/2016 |
| CN | 107429024 A | 12/2017 |
| CN | 109426076 A | 3/2019 |
| CN | 110499137 A | 11/2019 |
| JP | S61-076459 A | 4/1986 |
| JP | H04-214727 A | 8/1992 |
| JP | H07-100693 B2 | 11/1995 |
| JP | 2002-334869 A | 11/2002 |
| JP | 2005-128509 A | 5/2005 |
| JP | 2005-272483 A | 10/2005 |
| JP | 2006-285095 A | 10/2006 |
| JP | 2006-293298 A | 10/2006 |
| JP | 2007-137960 A | 6/2007 |
| JP | 2007-164149 A | 6/2007 |
| JP | 2007-199653 A | 8/2007 |
| JP | 2009-269953 A | 11/2009 |
| JP | 2010-122656 A | 6/2010 |

(56) References Cited

FOREIGN PATENT DOCUMENTS

| | | | |
|---|---|---|---|
| JP | 2010-173981 A | 8/2010 | |
| JP | 2010-181605 A | 8/2010 | |
| JP | 2011-132168 A | 7/2011 | |
| JP | 2012-215842 A | 11/2012 | |
| JP | 2013-137334 A | 7/2013 | |
| JP | 2013-253227 A | 12/2013 | |
| JP | 2015-007033 A | 1/2015 | |
| JP | 2016-044272 A | 4/2016 | |
| JP | 2016-060886 A | 4/2016 | |
| JP | 2017-119671 A | 7/2017 | |
| KR | 1020170134334 A | 12/2017 | |
| RU | 2663160 C2 | 8/2018 | |
| TW | I633084 B | 8/2018 | |
| TW | I637942 B | 10/2018 | |
| WO | 89/10946 A1 | 11/1989 | |
| WO | 91/09070 A1 | 6/1991 | |
| WO | 2004/066377 A1 | 8/2004 | |
| WO | 2009039635 A1 | 4/2009 | |
| WO | 2011/132641 A1 | 10/2011 | |
| WO | 2014/208324 A1 | 12/2014 | |
| WO | 2015/140016 A1 | 9/2015 | |
| WO | 2016/118873 A1 | 7/2016 | |
| WO | 2017/222291 A2 | 12/2017 | |
| WO | 2018/212116 A1 | 11/2018 | |
| WO | 2019/146378 A1 | 8/2019 | |
| WO | 2020/009016 A1 | 1/2020 | |

OTHER PUBLICATIONS

Aug. 31, 2020 Extended Search Report issued in European Patent Application No. 20166913.2.
Zhubanov, B. A. et al. "Synthesis of polymers of ladder structure from nitriles". Vysokomolekularnye Soedinenia, Seriya B, vol. 26, pp. 669-672, 1984.
Ie, Y. et al. "Electron-accepting pi-Conjugated Systems Based on Cyclic Imide and Cyano-substituted Benzothiadiazole for Non-fullerene Organic Photovoltaics". Chemistry Letters, vol. 44, pp. 694-696, 2015.
Watson, K. A. et al. "Polymer Synthesis via a Diels-Alder Reaction between Bis(Isobenzofuran)s and Bis(Phenylacetylene)s Containing Preformed Phthalimide Rings". High Performance Polymers, vol. 12, pp. 299-314, 2000.
Li, X. et al. "Preparation of low-k polyimide resin with outstanding stability of dielectric properties versus temperature by adding a reactive Cardo-containing diluent". Composites, Part B: Engineering, vol. 177, pp. 1-11, 2019.
Sep. 16, 2020 Extended Search Report issued in European Patent Application No. 20166912.4.
Paul, C.W. et al.: "High-temperature-curing end caps for polyimide oligomers", Advances in Polyimide Science and Technology: Proceedings of the Fourth International Conference on Polyimides, pp. 220-244, XP009522290.
Voznesenskaya, N.N. et al.: "Synthesis and Properties of Oligomers With Terminal Acetylenic Groups", Doklady Chemistry, vol. 279, No. 11, 1984, pp. 388-390, XP009522287.
Nosova, G.I. et al.: "Synthesis, thermal and relaxation properties of oligoimide with acetylene end groups", Vysokomolekulyarnye Soedineniya, Seriya A, vol. 34, No. 6, 1992, pp. 14-23, XP009522289.
Kumar, U. et al.: "Hybrid Polyimide-Prophenylenes by the Diels-Alder Polymerization Between Biscyclopentadienones and Ethnyl-Terminated Imides", Water-Soluble Polymers: Synthesis, Solution Properties and Applications, vol. 614, 1995, pp. 518-526, XP002047532.
Li, X. et al.: "Properties of a Silicone-Containing Arylacetylene Resin Modified with an Acetylene-Terminated Polyetherimide", Shiyou Huagong—Petrochemical Technology, vol. 44, No. 9, 2015, pp. 1115-1120, XP009522299.
Unroe, M.R. et al.: "Thermoset resins containing sterically hindered alkyne groups for redused crosslink density", Journal of Polymer Science Part A: Polymer Chemistry, vol. 28, No. 8, 1990, pp. 2207-2221, XP0055723148.
Kumar, D. et al.: "Melt—Polymerizable Bisimido-Bisphthalonitriles Containing Silicon, Fluoro, and Ether Groups: Synthesis, Characterization, and NMR Study", Journal of Polymer Science, Part A: Polymer Chemistry Edition, vol. 30, No. 7, 1992, pp. 1477-1487, XP000281802.
Achar, B.N. et al.: "New polymerizable bis(phthalonitrile) derivatives with ester-imide linkages", Journal of Polymer Materials, vol. 1, No. 3, 1984, pp. 149-155, XP009522300.
Achar, B.N. et al.: "Synthesis and characterization of polymerizable bisphthalonitrile monomers", Journal of Polymer Science, Polymer Chemistry Edition, vol. 21, No. 1, 1983, pp. 111-120, XP055723144.
Jun. 25, 2021 Office Action issued in Korean Patent Application No. 2020-0045935.
Jun. 29, 2021 Office Action issued in Korean Patent Application No. 2020-0045934.
U.S. Appl. No. 16/850,099, filed Apr. 16, 2020 in the name of Daisuke Kori et al.
Sep. 24, 2021 Office Action and Search Report issued in Taiwanese Patent Application No. 109112279.
Aug. 30, 2022 Office Action issued in U.S. Appl. No. 16/850,099.
Jul. 20, 2022 Office Action issued in Chinese Patent Application No. 202010295641.X.
Jiashen et al., "Studies on a Kind of Negative Photoresist Based on Photosensitive Polyimides," vol. 17, No. 4, pp. 334-337, Nov. 1999 (with partial translation).
Wilson et al., "Electronic Devices and Material No. 06," pp. 40-45, Dec. 27, 1986 (with partial translation).
CAS Registry No. 642446-27-3, Jan. 28, 2004.

\* cited by examiner

[FIG. 1]
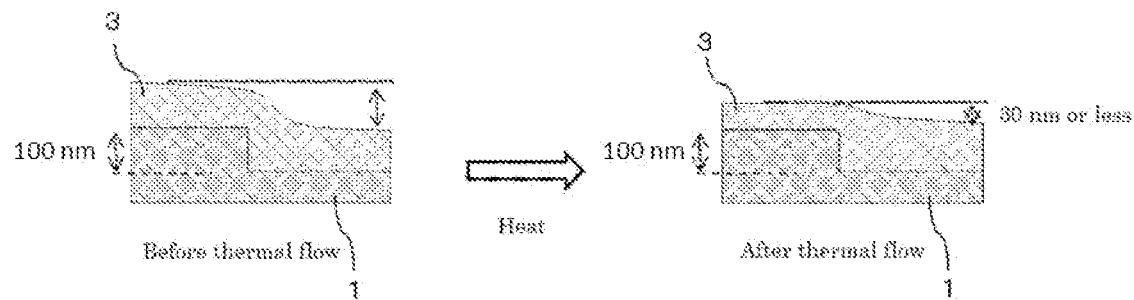
[FIG. 2]
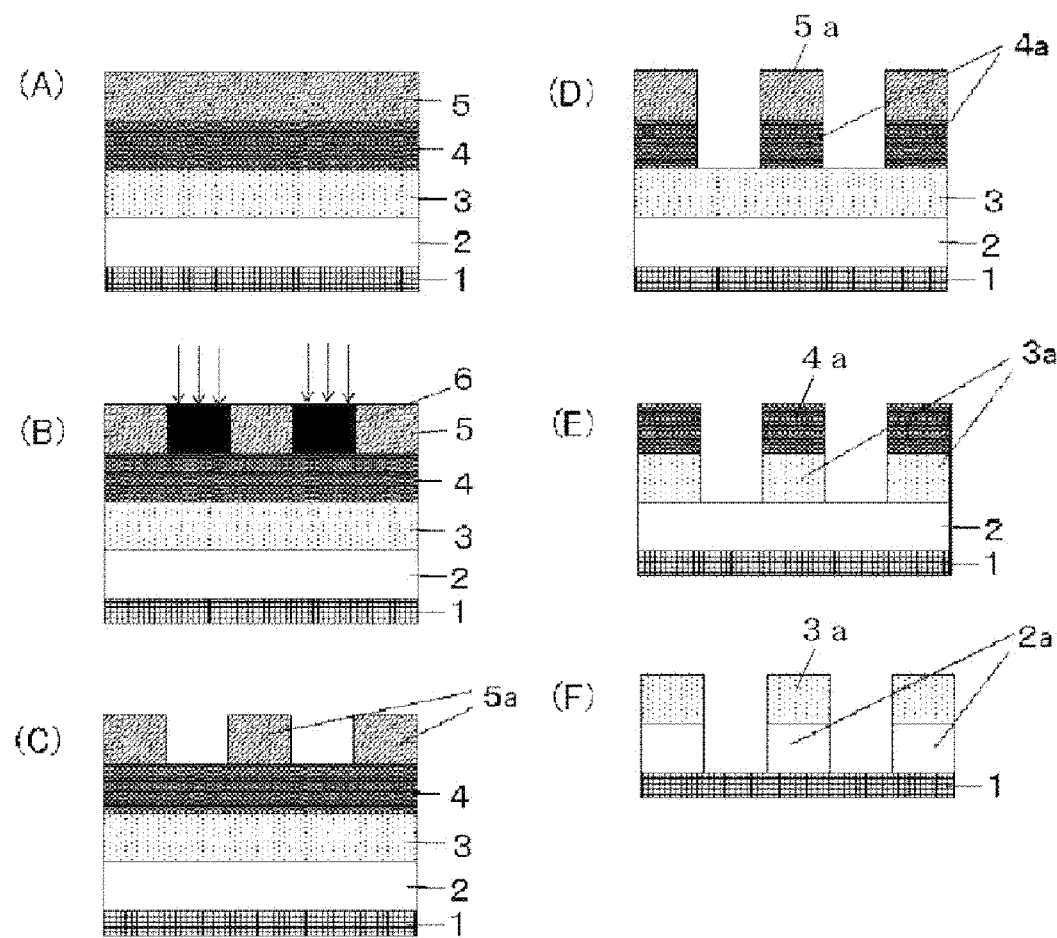

[FIG. 3]
(G)
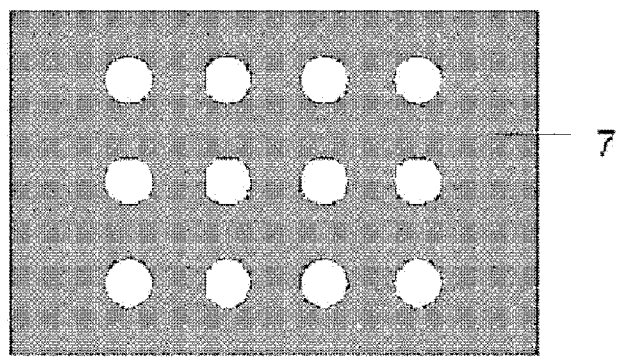
(H)
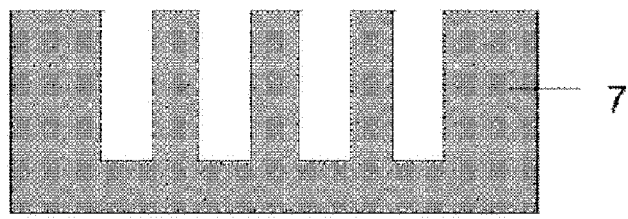
(I)
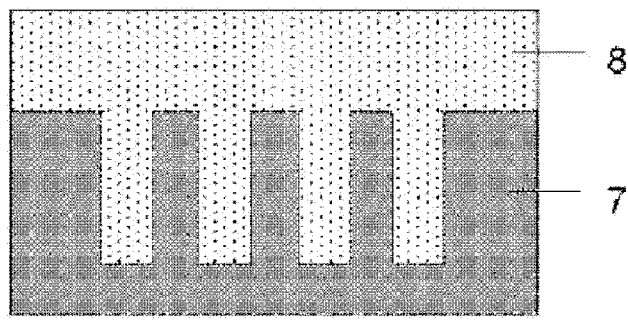

[FIG. 4]
(J)
(K)
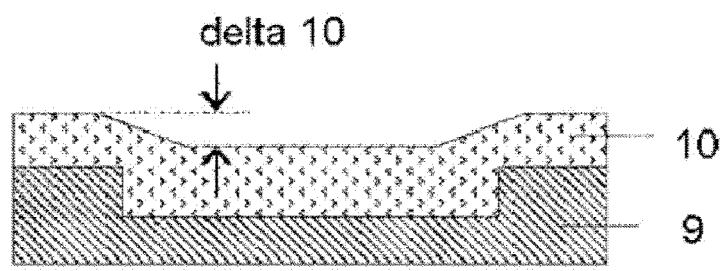

MATERIAL FOR FORMING ORGANIC FILM, SUBSTRATE FOR MANUFACTURING SEMICONDUCTOR DEVICE, METHOD FOR FORMING ORGANIC FILM, PATTERNING PROCESS, AND COMPOUND FOR FORMING ORGANIC FILM

TECHNICAL FIELD

The present invention relates to: a material for forming an organic film used in a semiconductor device manufacturing process; a substrate for manufacturing a semiconductor device using the material; a method for forming an organic film; a patterning process by a multilayer resist method; and a compound for forming an organic film suitably used in the material.

BACKGROUND ART

Conventionally, high integration and high processing speed of semiconductor devices have been achieved through the miniaturization of pattern size by shortening the wavelength of light sources in lithography technology using light exposure (photolithography), which is commonly employed technology. To form such a fine circuit pattern on a semiconductor device substrate (substrate to be processed), the following method is generally employed in which the substrate to be processed is processed by dry etching using a patterned photoresist film as an etching mask. In practice, however, there is no dry etching method capable of providing an absolute etching selectivity between the photoresist film and the substrate to be processed. Hence, recently, it has been common to process a substrate by a multilayer resist method. This method is as follows: first, a middle layer film having a different etching selectivity from a photoresist film (hereinafter, resist upper layer film) is placed between the resist upper layer film and a substrate to be processed; a pattern is formed in the resist upper layer film; then, the pattern is transferred to the middle layer film by dry etching using the resist upper layer film pattern as a dry etching mask; further, the pattern is transferred to the substrate to be processed by dry etching using the middle layer film as a dry etching mask.

One of the multilayer resist methods is a 3-layer resist method which can be performed with a typical resist composition used in a monolayer resist method. In this method, a substrate to be processed is coated with an organic underlayer film material composed of an organic resin-containing composition and then baked to form an organic underlayer film (hereinafter, organic film); the organic film is subsequently coated with a resist middle layer film material composed of a composition containing a silicon-containing resin, and baked to form a silicon-containing film (hereinafter, silicon middle layer film); thereafter, a typical organic photoresist film (hereinafter, resist upper layer film) is formed on the silicon middle layer film. The resist upper layer film is patterned and then subjected to dry etching with fluorine-based gas plasma, so that the organic resist upper layer film can exhibit a favorable etching selectivity ratio relative to the silicon middle layer film. Thus, the resist upper layer film pattern can be transferred to the silicon middle layer film. This method allows a pattern to be easily transferred to the silicon middle layer film even if a resist upper layer film does not have film thickness sufficient for directly processing the substrate to be processed or if a resist upper layer film does not have sufficient dry etching resistance for processing the substrate to be processed. This is because the silicon middle layer film generally has a film thickness equal to or smaller than the resist upper layer film. Subsequently, using the silicon middle layer film having the transferred pattern as a dry etching mask, the pattern is transferred to the organic underlayer film by dry etching with oxygen- or hydrogen-based gas plasma. Thereby, the pattern can be transferred to the organic underlayer film having dry etching resistance sufficient for substrate processing. This organic underlayer film pattern having the transferred pattern can be transferred to the substrate by dry etching with a fluorine-based gas, chlorine-based gas, or the like.

Meanwhile, the miniaturization in the semiconductor device manufacturing process is approaching the limit inherent in the wavelength of light sources for photolithography. Accordingly, recently, the high integration of semiconductor devices that does not rely on miniaturization has been examined. As one means for the high integration, semiconductor devices having complicated structures such as multigate structure have been examined, and some of these have been already put into practical use. In forming such structures by multilayer resist methods, it is possible to employ an organic film material which is capable of filling a fine pattern including hole, trench, and fin formed on a substrate to be processed with a film without space, and capable of filling a step- or pattern-dense region and a pattern-free region with a film and planarizing the regions. The use of such an organic film material to form an organic underlayer film having a flat surface on a stepped substrate reduces fluctuations in film thicknesses of a silicon middle layer film and a resist upper layer film formed thereon, and can suppress reductions in a focus margin in photolithography and a margin in a subsequent step of processing the substrate to be processed. This makes it possible to manufacture semiconductor devices with high yields. On the other hand, in the monolayer resist method, the upper resist film has to have a large film thickness to fill a stepped or patterned substrate to be processed. As a result, for example, pattern collapse occurs after exposure and development, and the pattern profile deteriorates due to reflection from the substrate at exposure. Consequently, the pattern formation margin at exposure is narrowed, making it difficult to manufacture semiconductor devices with high yields.

Further, as techniques for the high processing speed of next-generation semiconductor devices, for example, the applications of the following materials have also started to be examined: novel materials having high electron mobility using strained silicon, gallium arsenic, and so forth; and high-precision materials such as ultrathin polysilicon controlled in units of angstrom. However, in substrates to be processed to which such novel high-precision materials are applied, the materials may be corroded by oxygen in air under conditions during the flat film formation from an organic underlayer film material as described above, for example, film formation conditions of air and 300° C. or higher. Hence, such a performance as a high processing speed of a semiconductor device according to the material design cannot be exhibited, and industrially satisfactory yield may not be achieved. For this reason, an organic underlayer film material capable of forming a film in an inert gas has been desired so as to avoid a decrease in yield due to substrate corrosion by air under such high temperature conditions.

Conventionally, condensed resins using aromatic alcohols and carbonyl compounds such as ketones and aldehydes as condensing agents for a phenol compound or naphthol compound have been known as materials for forming an organic film for multilayer resist methods. Examples of such condensed resins include a fluorene bisphenol novolak resin described in Patent Document 1, a bisphenol compound and a novolak resin thereof described in Patent Document 2, a novolak resin of an adamantane phenol compound described in Patent Document 3, a bisnaphthol compound and a novolak resin thereof described in Patent Document 4, and the like. Crosslinking by a methylol compound as a crosslinking agent, or a curing action by a crosslinking reaction by oxidation at the α-position of an aromatic ring by the action of oxygen in air and the following condensation causes these materials to form films having solvent resistance in relation to a coating film material used in the subsequent step.

Further, a material in which triple bonds are employed as intermolecular linking groups in a curable resin is known. For example, Patent Documents 5 to 10 are known. In these materials, a cured film having solvent resistance is formed not only by the methylol-derived crosslinking, but also by crosslinking by polymerization with triple bonds. However, these materials for forming an organic film do not have sufficient filling property of a pattern formed on a substrate or sufficient planarizing property.

Moreover, as examples of compounds having an imide structure shown in the present invention, a resin having a polyimide structure described in Patent Document 11 and Patent Document 12 in which a compound having a bismaleimide structure is used are known. However, regarding these materials, there are no examples regarding a terminal substituent having a triple bond on a nitrogen atom, and cured film formation in an inert gas, fluctuation in film thickness due to thermal decomposition under high temperature conditions, filling property, planarizing property, and so forth have not been known.

CITATION LIST

Patent Literature

Patent Document 1: Japanese Patent Laid-Open Publication No. 2005-128509
Patent Document 2: Japanese Patent Laid-Open Publication No. 2006-293298
Patent Document 3: Japanese Patent Laid-Open Publication No. 2006-285095
Patent Document 4: Japanese Patent Laid-Open Publication No. 2010-122656
Patent Document 5: Japanese Patent Laid-Open Publication No. 2010-181605
Patent Document 6: International Publication No. WO2014-208324
Patent Document 7: Japanese Patent Laid-Open Publication No. 2012-215842
Patent Document 8: Japanese Patent Laid-Open Publication No. 2016-044272
Patent Document 9: Japanese Patent Laid-Open Publication No. 2016-060886
Patent Document 10: Japanese Patent Laid-Open Publication No. 2017-119671
Patent Document 11: Japanese Patent Laid-Open Publication No. 2013-137334
Patent Document 12: International Publication No. WO2018-212116

SUMMARY OF INVENTION

Technical Problem

The present invention has been made in view of the above circumstances. An object of the present invention is to provide: a compound containing an imide group which is not only cured under film formation conditions of inert gas as well as air and has excellent heat resistance and properties of filling and planarizing a pattern formed on a substrate, but can also form an organic underlayer film with favorable adhesion to a substrate, and a material for forming an organic film containing the compound. Further, the present invention also provides a substrate for manufacturing a semiconductor device using the material, a method for forming an organic film and a patterning process.

Solution to Problem

To achieve the above object, the present invention provides a material for forming an organic film, comprising:

(A) a compound for forming an organic film shown by the following general formula (1A); and (B) an organic solvent,

(1A)

wherein $W_1$ represents an organic group with a valency of n1, n1 represents an integer of 2 to 4, and $X_1$ represents any of groups shown by the following general formulae (1B) and (1C),

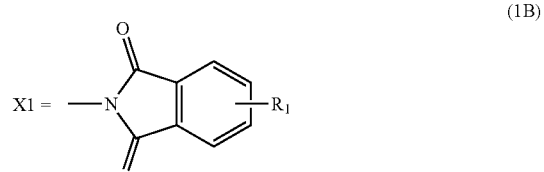

(1B)

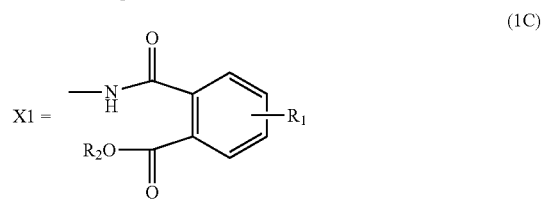

(1C)

wherein $R_1$ represents any of groups shown by the following formula (1D), and two or more kinds of $R_1$ may be used in combination; $R_2$ represents a hydrogen atom or a linear or branched, saturated or unsaturated hydrocarbon group having 1 to 20 carbon atoms, and a methylene group constituting $R_2$ may be substituted with an oxygen atom or a carbonyl group,

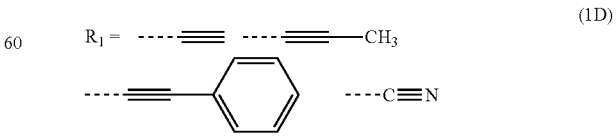

(1D)

noting that in the general formula (1B), when $W_1$ represents

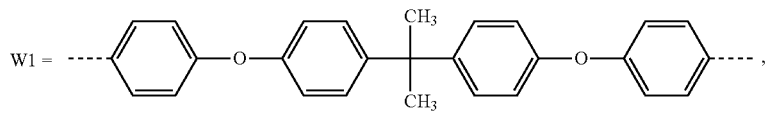

$R_1$ does not represent any of

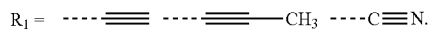

With such a material for forming an organic film, the material for forming an organic film can form an organic film which is cured under film formation conditions of inert gas as well as air, and has high heat resistance, favorable adhesion to a substrate, and high filling and planarizing properties.

Furthermore, the component (A) is preferably a compound shown by the following general formula (1E),

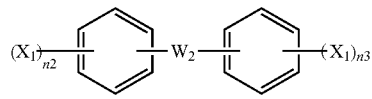

(1E)

wherein $W_2$ represents a single bond or a divalent organic group, n2 and n3 represent integers that satisfy $2 \leq n2+n3 \leq 4$, the benzene rings in the formula optionally have a substituent thereon, and an organic group in $W_2$ and a substituent on the benzene ring optionally bond to each other to form a cyclic organic group; $X_1$ represents any of groups shown by the general formulae (1B) and (1C).

It is preferable to have such an imide or an imide precursor structure in the compound for forming an organic film from the viewpoint of providing excellent heat resistance.

Furthermore, $W_2$ in the general formula (1E) preferably represents any of a single bond and groups shown by the following formula (1F),

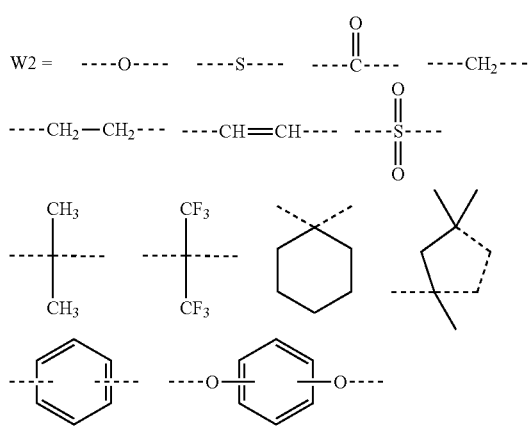

(1F)

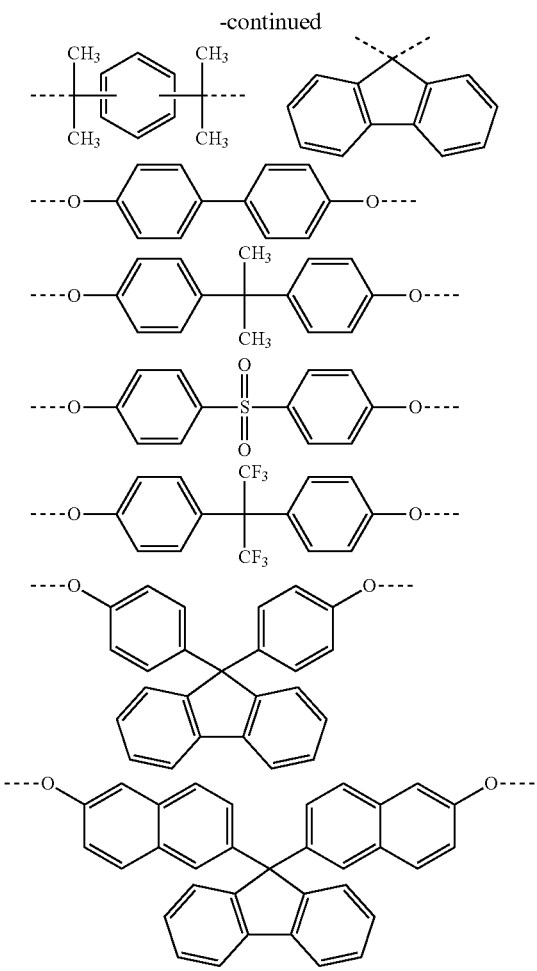

wherein an aromatic ring in the above formula may have a substituent thereon.

It is preferable to have such a structure in the compound for forming an organic film from the viewpoint of solubility in organic solvents.

Furthermore, preferably, n2 and n3 in the general formula (1E) satisfy the relation $1 \leq n2 \leq 2$, $1 \leq n3 \leq 2$, $2 \leq n2+n3 \leq 4$, and the $X_1$ is a group represented by the following general formula (1G),

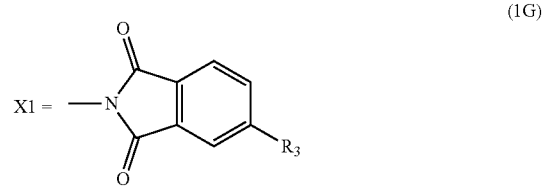

(1G)

wherein, $R_3$ represents any of groups shown by the following formula (1H), and two or more kinds of $R_3$ may be used in combination.

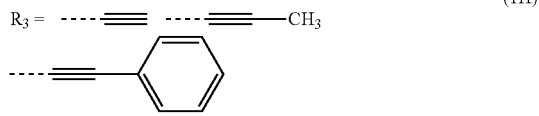

(1H)

Using such a compound, film shrinking in curing is suppressed, thus making it possible for the material for forming an organic film to form an organic film having excellent filling and planarizing properties.

Furthermore, the component (A) preferably satisfies $1.00 \leq Mw/Mn \leq 1.10$ where Mw is a weight average molecular weight and Mn is a number average molecular weight measured by gel permeation chromatography in terms of polystyrene.

Controlling Mw/Mn of the compound for forming an organic film within such a range, an organic film more excellent in filling property and planarizing property can be formed.

Furthermore, the component (B) is preferably a mixture of one or more kinds of organic solvent having a boiling point of lower than 180° C. and one or more kinds of organic solvent having a boiling point of 180° C. or higher.

With such a material for forming an organic film, the compound for forming an organic film is provided with thermal flowability by adding a high-boiling-point solvent, so that the material for forming an organic film has both high filling and planarizing properties.

Furthermore, the material for forming an organic film preferably further comprises at least one of (C) an acid generator, (D) a surfactant, (E) a crosslinking agent, and (F) a plasticizer.

A composition for forming an organic film in the present invention may include at least one of the above components depending on the purpose thereof.

Furthermore, the present invention provides a substrate for manufacturing a semiconductor device, comprising an organic film on the substrate, the organic film being formed by curing the material for forming an organic film.

The organic film of the present invention has both high filling and planarizing properties, and accordingly, the organic film does not have fine pores due to insufficient filling or asperity in the organic film surface due to insufficient planarizing property. A semiconductor device substrate planarized by the organic film of the present invention has an increased process margin at patterning, making it possible to manufacture semiconductor devices with high yields.

Furthermore, the present invention provides a method for forming an organic film employed in a semiconductor device manufacturing process, the method comprising:

spin-coating a substrate to be processed with the above material for forming an organic film; and heating the substrate to be processed coated with the material for forming an organic film under an inert gas atmosphere at a temperature of 50° C. or higher to 600° C. or lower within a range of 10 seconds to 7200 seconds to obtain a cured film.

Further, the present invention provides a method for forming an organic film employed in a semiconductor device manufacturing process, the method comprising:

spin-coating a substrate to be processed with the above material for forming an organic film;

heating the substrate to be processed coated with the material for forming an organic film in air at a temperature of 50° C. or higher to 250° C. or lower within a range of 5 seconds to 600 seconds to form a coating film; and then heating under an inert gas atmosphere at a temperature of 200° C. or higher to 600° C. or lower within a range of 10 seconds to 7200 seconds to obtain a cured film.

An organic film employed in a semiconductor device manufacturing process formed by the inventive method has high heat resistance and high filling and planarizing properties, and allows a favorable semiconductor device yield when used in a semiconductor device manufacturing process.

In this event, the inert gas preferably has an oxygen concentration of 1% or less.

The inventive material for forming an organic film is capable of forming an organic film which is sufficiently cured without generating a sublimation product even when the heating is performed under such an inert gas atmosphere, and which also has excellent adhesion to a substrate.

Furthermore, the substrate to be processed preferably has a structure or a step with a height of 30 nm or more.

The inventive method for forming an organic film is particularly useful when forming a flat organic film on such a substrate to be processed.

Furthermore, the present invention provides a patterning process comprising:

forming an organic film on a body to be processed from the above material for forming an organic film;

forming a silicon-containing resist middle layer film on the organic film from a silicon-containing resist middle layer film material;

forming a resist upper layer film on the silicon-containing resist middle layer film from a photoresist composition;

forming a circuit pattern in the resist upper layer film;

transferring the pattern to the silicon-containing resist middle layer film by etching using the resist upper layer film having the formed pattern as a mask;

transferring the pattern to the organic film by etching using the silicon-containing resist middle layer film having the transferred pattern as a mask; and further transferring the pattern to the body to be processed by etching using the organic film having the transferred pattern as a mask.

Furthermore, the present invention provides a patterning process comprising:

forming an organic film on a body to be processed from the above material for forming an organic film;

forming a silicon-containing resist middle layer film on the organic film from a silicon-containing resist middle layer film material;

forming an organic antireflective film on the silicon-containing resist middle layer film;

forming a resist upper layer film on the organic antireflective film from a photoresist composition, so that a 4-layered film structure is constructed;

forming a circuit pattern in the resist upper layer film;

transferring the pattern to the organic antireflective film and the silicon-containing resist middle layer film by etching using the resist upper layer film having the formed pattern as a mask;

transferring the pattern to the organic film by etching using the silicon-containing resist middle layer film having the transferred pattern as a mask; and further transferring the pattern to the body to be processed by etching using the organic film having the transferred pattern as a mask.

Furthermore, the present invention provides a patterning process comprising:

forming an organic film on a body to be processed from the above material for forming an organic film;

forming an inorganic hard mask selected from a silicon oxide film, a silicon nitride film, a silicon oxynitride film, a titanium oxide film, and a titanium nitride film on the organic film;

forming a resist upper layer film on the inorganic hard mask from a photoresist composition;

forming a circuit pattern in the resist upper layer film;

transferring the pattern to the inorganic hard mask by etching using the resist upper layer film having the formed pattern as a mask;

transferring the pattern to the organic film by etching using the inorganic hard mask having the transferred pattern as a mask; and further transferring the pattern to the body to be processed by etching using the organic film having the transferred pattern as a mask.

Furthermore, the present invention provides a patterning process comprising:

forming an organic film on a body to be processed from the above material for forming an organic film;

forming an inorganic hard mask selected from a silicon oxide film, a silicon nitride film, a silicon oxynitride film, a titanium oxide film, and a titanium nitride film on the organic film;

forming an organic antireflective film on the inorganic hard mask;

forming a resist upper layer film on the organic antireflective film from a photoresist composition, so that a 4-layered film structure is constructed;

forming a circuit pattern in the resist upper layer film;

transferring the pattern to the organic antireflective film and the inorganic hard mask by etching using the resist upper layer film having the formed pattern as a mask;

transferring the pattern to the organic film by etching using the inorganic hard mask having the transferred pattern as a mask; and further transferring the pattern to the body to be processed by etching using the organic film having the transferred pattern as a mask.

The inventive material for forming an organic film can be suitably used for various patterning processes such as a 3-layer resist process using a silicon-containing resist middle layer film or an inorganic hard mask, and a 4-layer resist process additionally using an organic antireflective film. In a semiconductor device manufacturing process, forming a circuit pattern by the inventive patterning process as described, a semiconductor device can be manufactured with a high yield.

In this event, the inorganic hard mask is preferably formed by a CVD method or an ALD method.

In the inventive patterning process, the inorganic hard mask can be formed by such a method, for example.

Furthermore, the circuit pattern is preferably formed by a lithography using light with a wavelength of 10 nm or more to 300 nm or less, a direct drawing by electron beam, a nanoimprinting, or a combination thereof.

Furthermore, when the circuit pattern is formed, the circuit pattern is preferably developed by alkaline development or development with an organic solvent.

In the inventive patterning process, such circuit pattern formation means and development means can be suitably used.

Furthermore, the body to be processed is preferably a semiconductor device substrate or the semiconductor device substrate coated with any of a metal film, a metal carbide film, a metal oxide film, a metal nitride film, a metal oxycarbide film, and a metal oxynitride film.

Furthermore, as the body to be processed, a body to be processed comprising silicon, titanium, tungsten, hafnium, zirconium, chromium, germanium, copper, silver, gold, aluminum, indium, gallium, arsenic, palladium, iron, tantalum, iridium, cobalt, manganese, molybdenum, or an alloy thereof is preferably used.

The inventive patterning process is capable of processing the body to be processed as described above to form a pattern.

Furthermore, the present invention provides a compound for forming an organic film shown by the following general formula (1A), $$W_1 \text{---} (X_1)_{n1} \tag{1A}$$

wherein $W_1$ represents an organic group with a valency of n1, n1 represents an integer of 2 to 4, and $X_1$ represents any of groups shown by the following general formulae (1B) and (1C), $$X1 = \text{---} \begin{array}{c} \text{(phthalimide structure with } R_1 \text{)} \end{array} \tag{1B}$$

$$X1 = \text{---} \begin{array}{c} \text{(amide-ester structure with } R_1, R_2O \text{)} \end{array} \tag{1C}$$

wherein $R_1$ represents any of groups shown by the following formula (1D), and two or more kinds of $R_1$ may be used in combination; $R_2$ represents a hydrogen atom or a linear or branched, saturated or unsaturated hydrocarbon group having 1 to 20 carbon atoms, and a methylene group constituting $R_2$ may be substituted with an oxygen atom or a carbonyl group, $$R_1 = \text{----}\equiv\text{----}\equiv\text{---}CH_3 \tag{1D}$$
$$\text{----}\equiv\text{---}\langle\text{phenyl}\rangle\text{----}C\equiv N$$

noting that in the general formula (1B), when $W_1$ represents

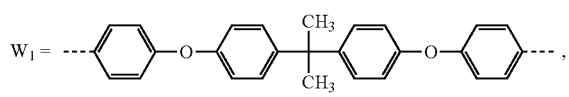

$R_1$ does not represent any of

With a compound having such an imide or imide precursor structure, the compound for forming an organic film can form an organic film which is cured under film formation conditions of inert gas as well as air, and has high heat resistance, favorable adhesion to a substrate, and high filling and planarizing properties.

Furthermore, the compound for forming an organic film is preferably shown by the following general formula (1E),

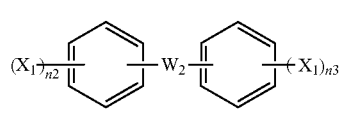

(1E)

wherein $W_2$ represents a single bond or a divalent organic group, n2 and n3 represent integers that satisfy $2 \leq n2+n3 \leq 4$, the benzene rings in the formula optionally have a substituent thereon, and an organic group in $W_2$ and a substituent on the benzene ring optionally bond to each other to form a cyclic organic group; $X_1$ represents any of groups shown by the general formulae (1B) and (1C).

Such a compound has curability under film formation conditions of inert gas as well as air, and can also exhibit excellent heat resistance under either film formation condition.

In this event, $W_2$ in the general formula (1E) preferably represents any of a single bond or groups shown by the following formula (1F),

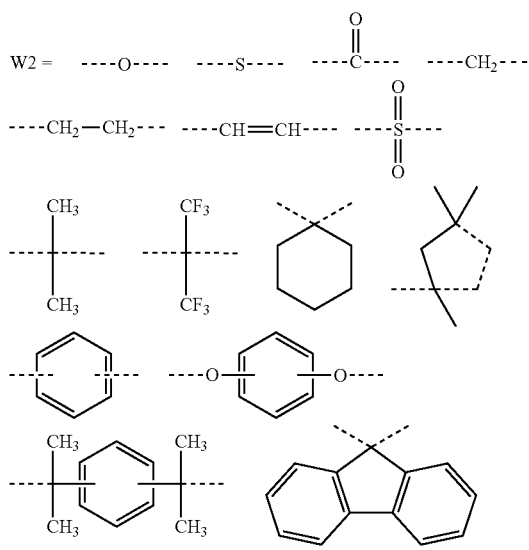

(1F)

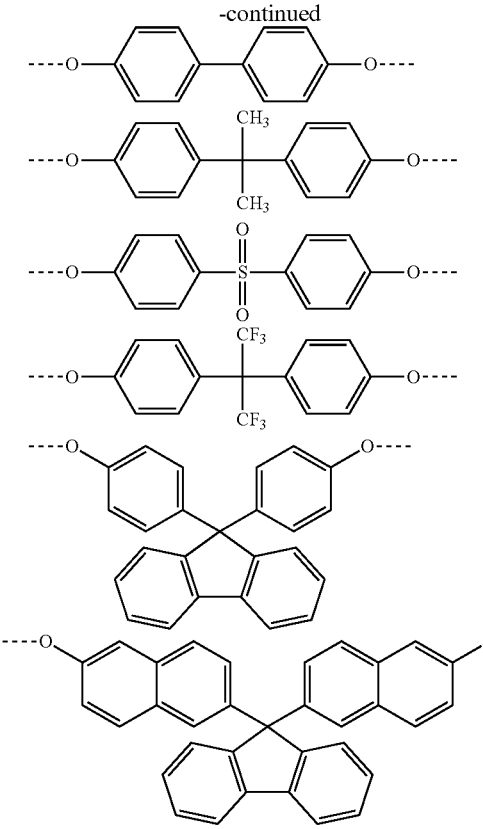

wherein an aromatic ring in the above formula may have a substituent thereon.

Such a compound has curability under film formation conditions of inert gas as well as air, and can also exhibit excellent heat resistance under either film formation condition.

Furthermore, preferably, n2 and n3 in the general formula (1E) satisfy the relation $1 \leq n2 \leq 2$, $1 \leq n3 \leq 2$, $2 \leq n2+n3 \leq 4$, and the $X_1$ is a group represented by the following general formula (1G),

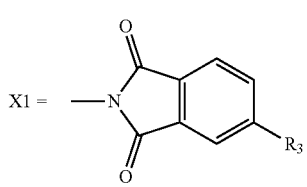

(1G)

wherein, $R_3$ represents any of groups shown by the following formula (1H), and two or more kinds of $R_3$ may be used in combination.

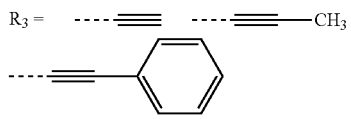

(1H)

With such a compound, film shrinking in curing is suppressed, thus making it possible for the compound for forming an organic film to have excellent filling and planarizing properties.

Advantageous Effects of Invention

As described above, the inventive compound is a compound useful for forming an organic underlayer film which is cured without generating a by-product even in film formation in an inert gas for preventing substrate corrosion, and also has high filling and planarizing properties. Moreover, a material for forming an organic film containing this compound is a material which forms an organic film having excellent filling and planarizing properties, and also having characteristics such as heat resistance and etching resistance. Accordingly, the material is extremely useful as, for example, an organic film material in a multilayer resist method such as a 2-layer resist method, a 3-layer resist method using a silicon-containing middle layer film, and a 4-layer resist method using a silicon-containing middle layer film and an organic antireflective film, or as a planarizing material for manufacturing a semiconductor device. Moreover, an organic film formed from the inventive material for forming an organic film has excellent heat resistance, and therefore, is suitable for patterning since there is no fluctuation in film thickness due to thermal decomposition even when a CVD hard mask is formed on the organic underlayer film.

BRIEF DESCRIPTION OF DRAWINGS

FIG. 1 is an explanatory diagram of the planarizing property in the present invention;

FIG. 2 is an explanatory diagram of an example of an inventive patterning process according to a 3-layer resist method;

FIG. 3 is an explanatory diagram of a method for evaluating the filling property in Examples; and FIG. 4 is an explanatory diagram of a method for evaluating the planarizing property in Examples.

DESCRIPTION OF EMBODIMENTS

As described above, it has been desired to develop a material for forming an organic film, which generates no by-product under such a film formation condition in an inert gas as to prevent substrate corrosion, for example, even at 300° C. or higher, and which is capable of forming an organic underlayer film not only excellent in properties of filling and planarizing a pattern formed on a substrate but also favorable for dry etching resistance during substrate processing. Moreover, it has been desired to develop: a material for forming an organic film, which causes no fluctuation in film thickness of the organic underlayer film due to thermal decomposition even when a CVD hard mask is formed on the organic underlayer film; and a compound for forming an organic film useful in a patterning process using the material.

Generally, when an organic underlayer film is formed, a composition is formed by dissolving a compound for forming an organic film in an organic solvent. Then, a substrate on which a structure of a semiconductor device, wiring, and so forth have been formed is coated with this composition and baked to form the organic underlayer film. Immediately after the application of the composition, a coating film is formed in a shape according to a step structure on the substrate. Nevertheless, when the coating film is baked, most of the organic solvent is evaporated before curing, so that an organic film is formed from the compound for forming an organic film remaining on the substrate. The present inventors have considered that if the compound for forming an organic film remaining on the substrate has sufficient thermal flowability, the step profile immediately after the application is planarized by thermal flow, and a flat film can be formed.

The present inventors further earnestly studied and consequently found that with a compound for forming an organic film having an imide structure or an imide ring precursor structure shown by the following general formula (1B) or (1C), a substituent shown by $R_1$ having a triple bond provides thermosetting property equivalent to that of a conventional underlayer film material not only in air but also in inert gas. In addition, the material for forming an organic film generates no by-product during the curing reaction by the triple bond shown by $R_1$, which is a linking group, and the thermal flowability is favorable. Accordingly, the present inventors have found that the material for forming an organic film has all of high filling and planarizing properties, favorable dry etching resistance, and such heat resistance that the material causes no fluctuation in coating film thickness due to thermal decomposition even when a CVD hard mask is formed, and have completed the present invention.

That is, the present invention is a material for forming an organic film, including:

(A) a compound for forming an organic film shown by the following general formula (1A); and (B) an organic solvent.

Furthermore, the present invention is a compound for forming an organic film shown by the following general formula (1A).

Hereinafter, the present invention will be described in detail. However, the present invention is not limited thereto.

<Compound for Forming Organic Film>

The inventive compound for forming an organic film is a compound having the imide or imide precursor structure shown by the following general formula (1A).

(1A)

(where $W_1$ represents an organic group with a valency of n1, n1 represents an integer of 2 to 4, and $X_1$ represents any of groups shown by the following general formulae (1B) and (1C).

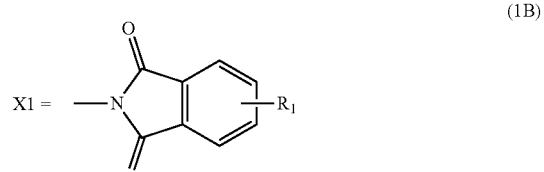

(1B)

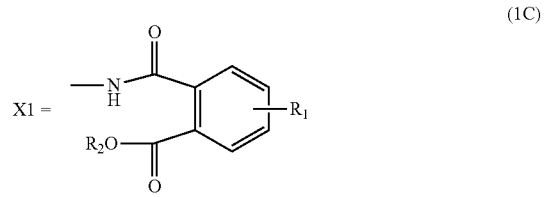

(1C)

(where $R_1$ represents any of groups shown by the following formula (1D), and two or more kinds of $R_1$ may be used in combination; $R_2$ represents a hydrogen atom or a linear or branched, saturated or unsaturated hydrocarbon group having 1 to 20 carbon atoms, and a methylene group constituting $R_2$ may be substituted with an oxygen atom or a carbonyl group.)

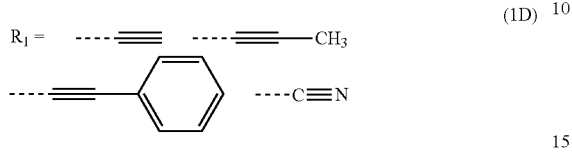

(1D)

Note that in the general formula (1B), when $W_1$ represents

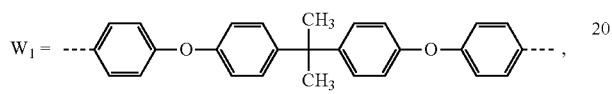

$R_1$ does not represent any of

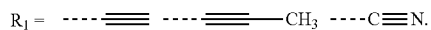

$R_1$ shown by the above (1D) functions as a thermal linking group. In view of curability, heat resistance and availability of raw material, $R_1$ preferably represents an ethynyl group or an ethynylphenyl group.

In order to provide flowability and solvent solubility, $R_2$ in the formula (1C) may have a long chain or a branched structure of hydrocarbon introduced or the methylene group may be substituted with an oxygen atom or a carbonyl group. Moreover, by employing an imide structure which is already ring-closed like (1B), an elimination reaction such as a dehydration which occurs when an imide compound precursor such as amic acid undergoes thermal ring closure is eliminated. Thus, film shrinking is suppressed and the planarizing property of the organic film is not lost. Furthermore, by obtaining a stable imide compound beforehand, decomposition and the like of an imide compound precursor such as an amic acid due to an equilibrium reaction can be suppressed, allowing superiority in storage stability as well. In view of the above points, the structure in (1B) is more preferable.

Examples of $W_1$ in the above general formula include the following structural formula, and these aromatic rings may have a substituent thereon. Furthermore, examples of the substituent include a hydroxyl group, a trifluoromethyl group, an alkyl group having 1 to 10 carbon atoms, an alkynyl group and an alkenyl group having 3 to 10 carbon atoms, an alkyloxy group having 1 to 10 carbon atoms, an alkynyloxy group and an alkenyloxy group having 3 to 10 carbon atoms, an aryl group having 6 to 10 carbon atoms, a thiol group, a nitro group, a halogen group, a nitrile group, a sulfonic acid group, an alkoxycarbonyl group having 1 to 10 carbon atoms, and an alkanoyloxy group having 1 to 10 carbon atoms.

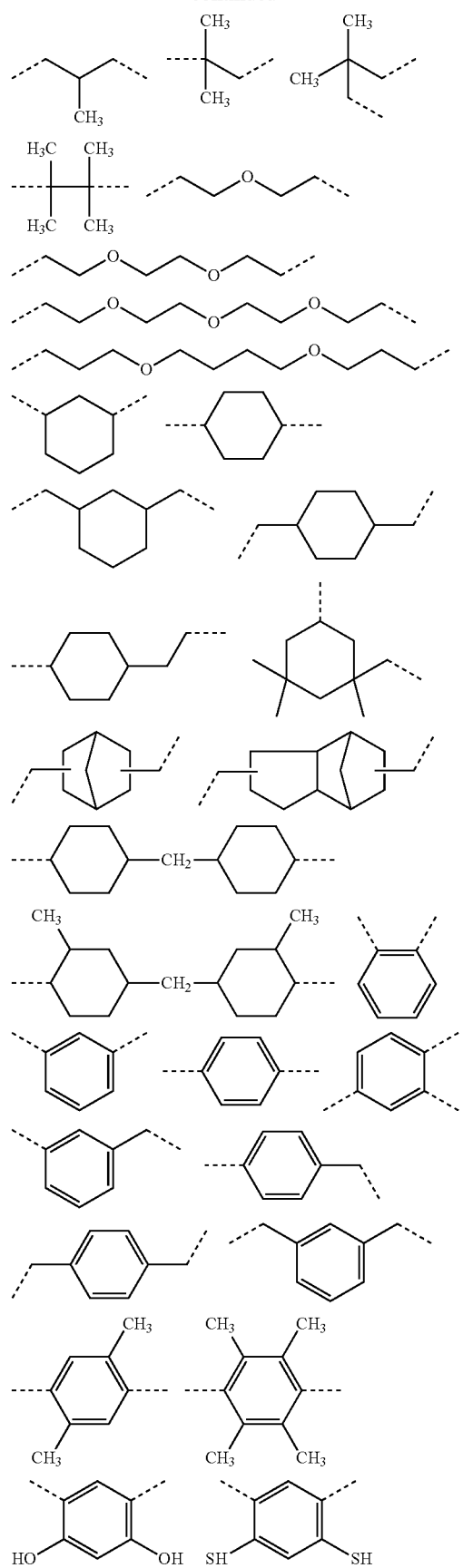

-continued
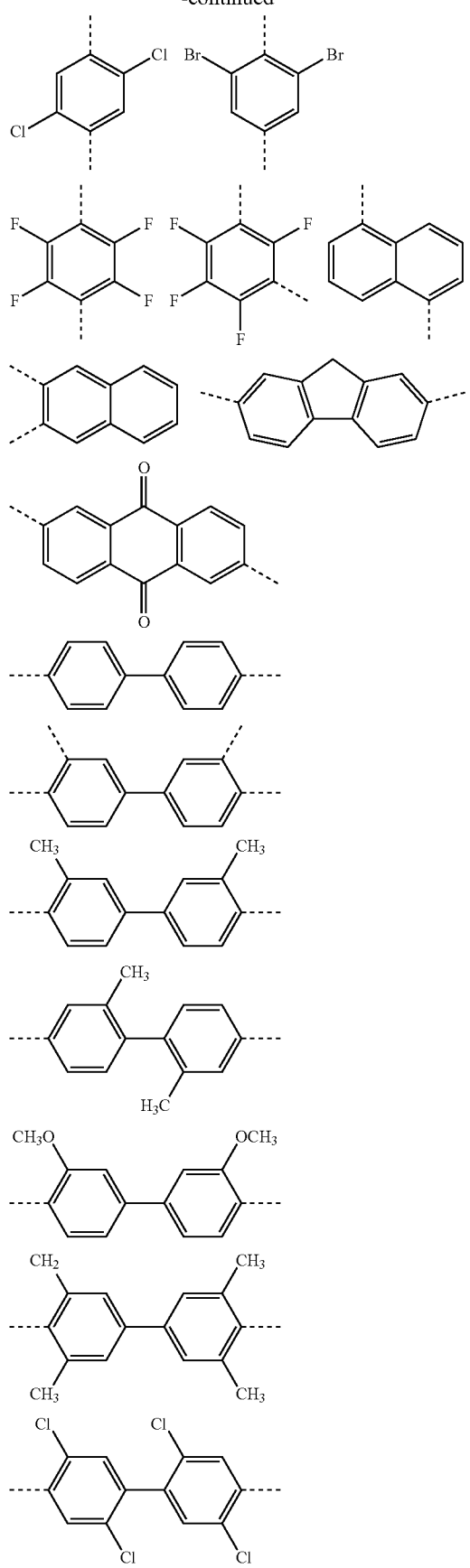
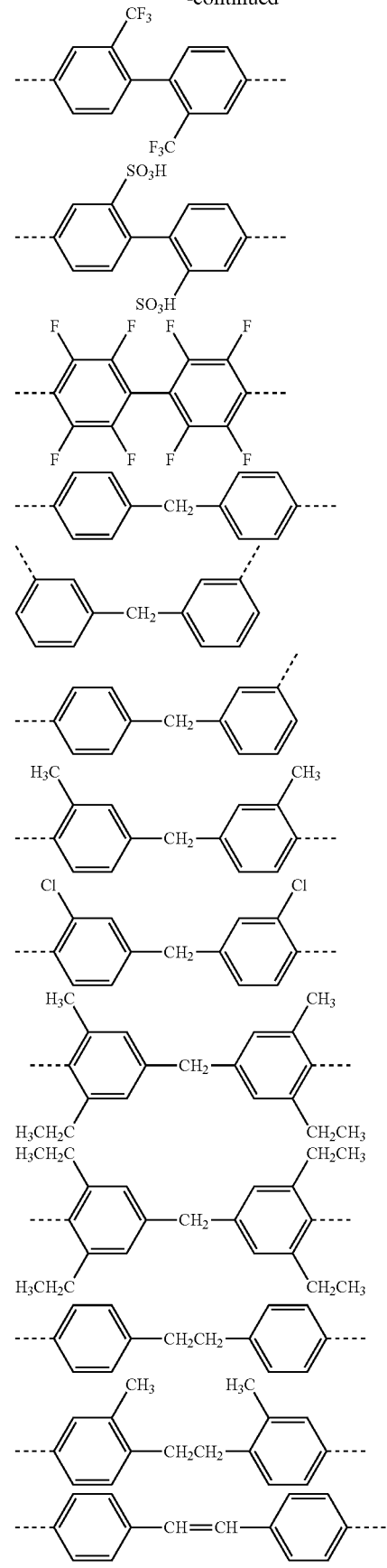

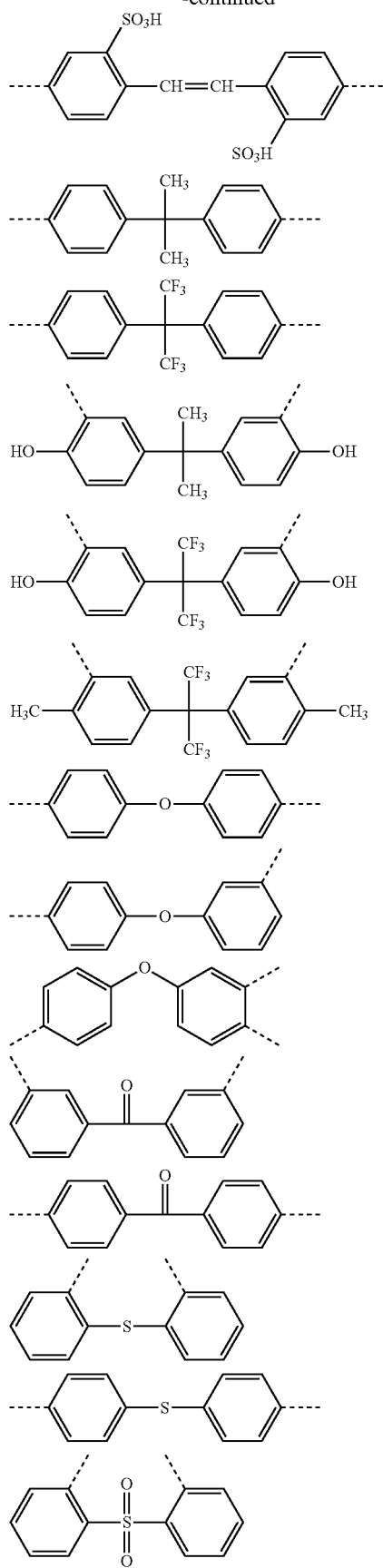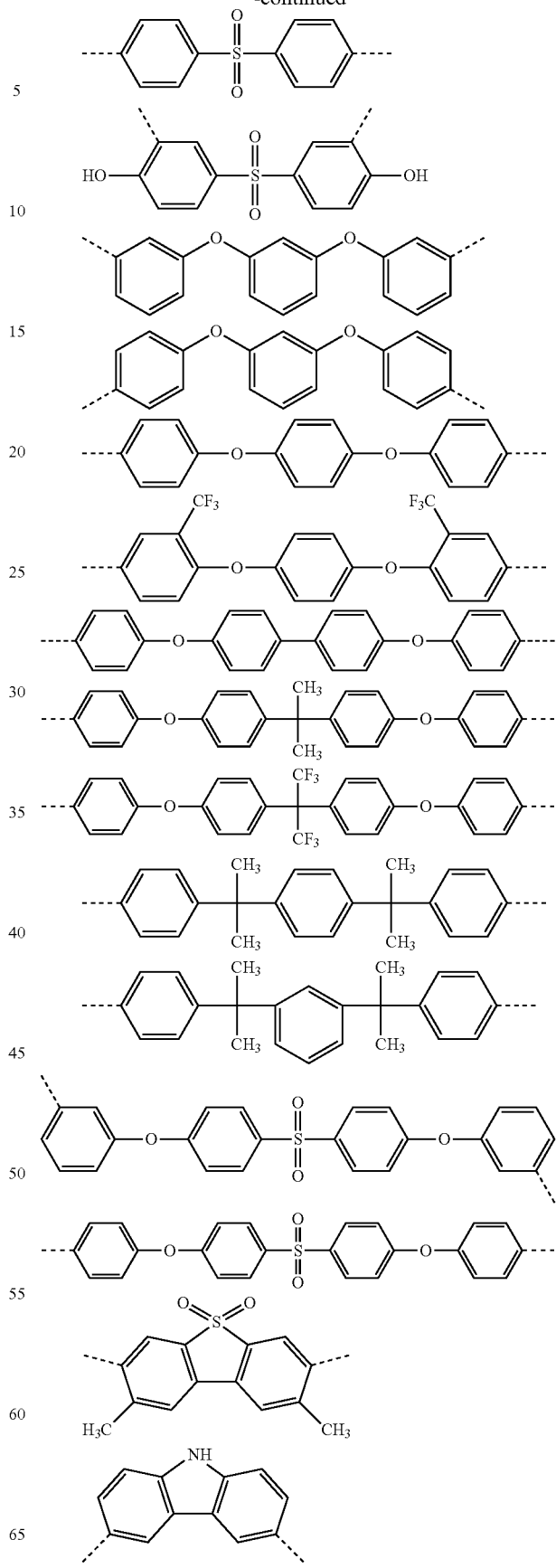

-continued
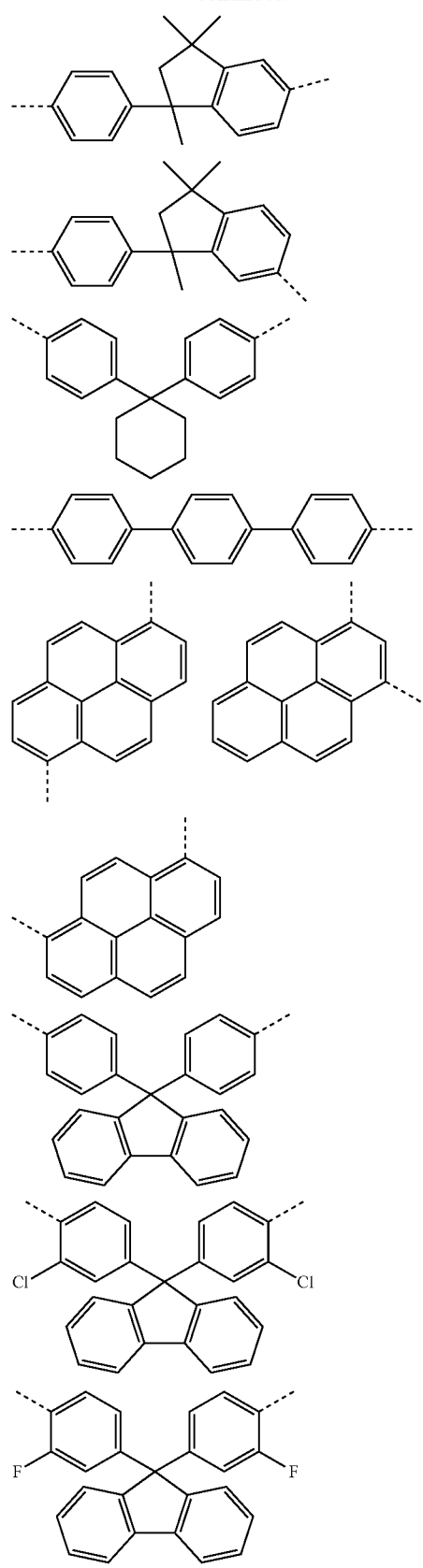
-continued
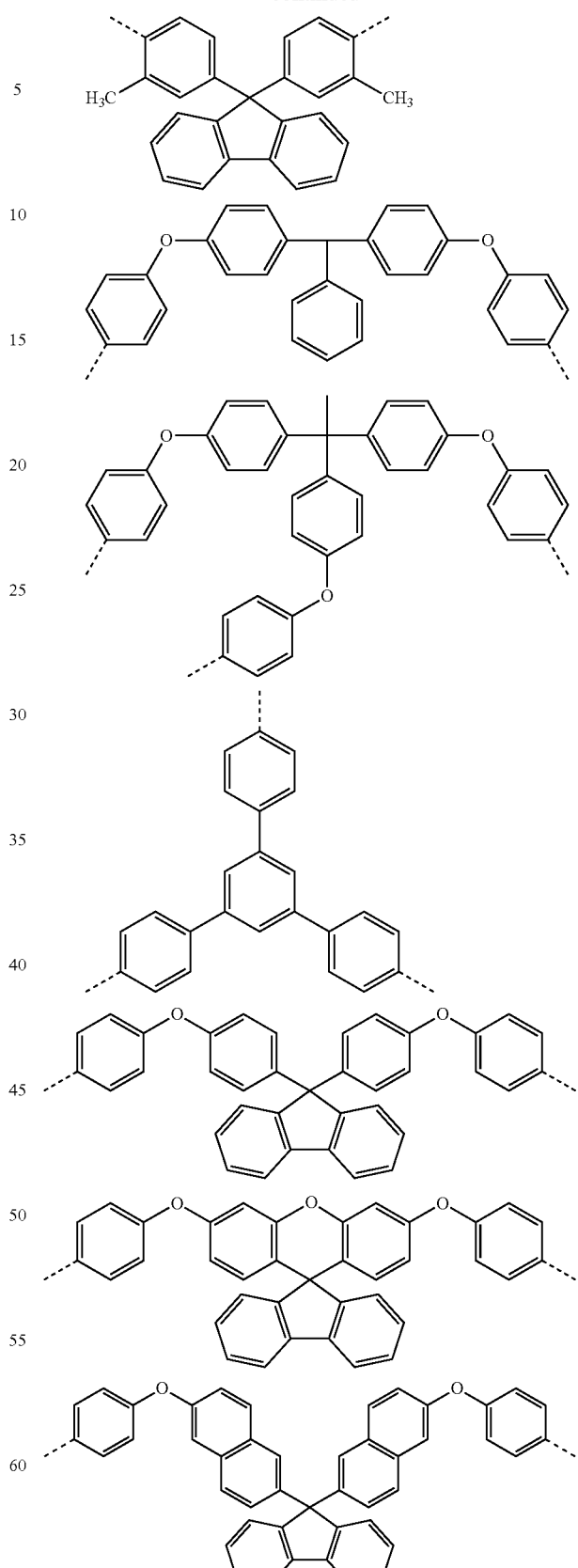

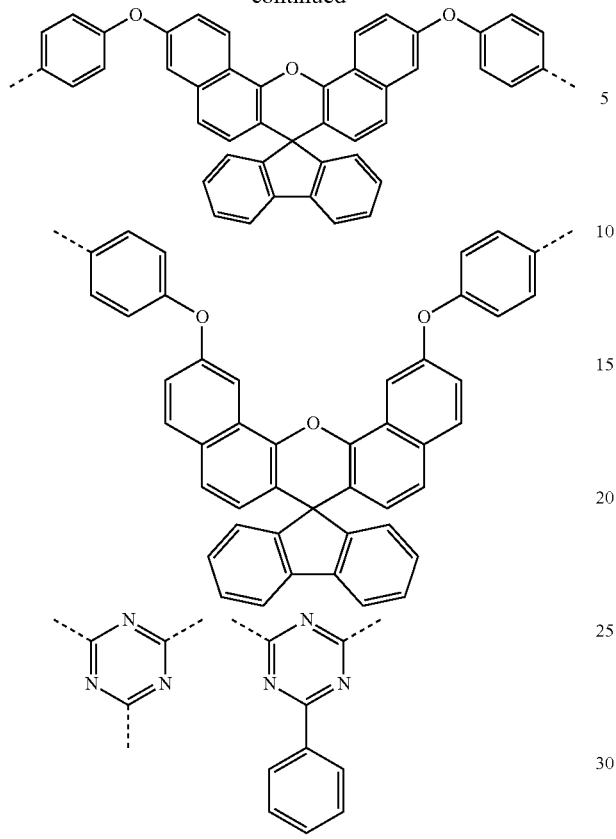

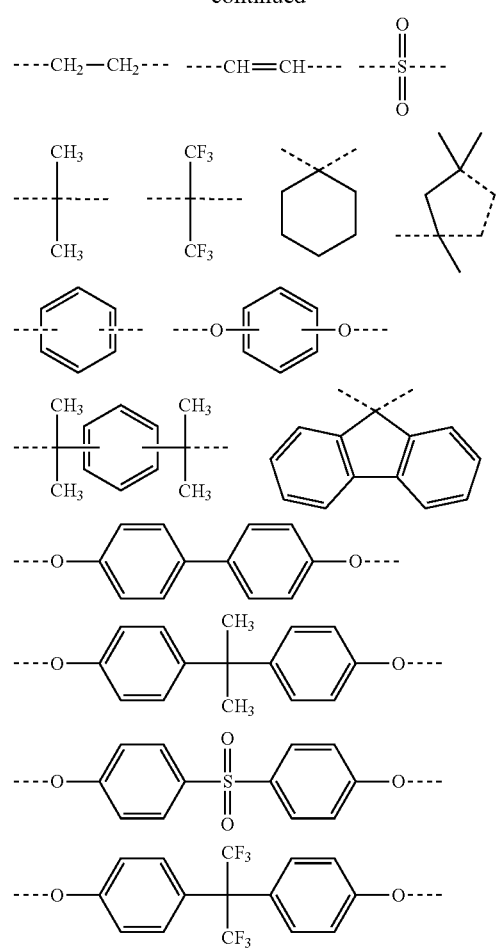

In the present invention, the compound for forming an organic film is preferably a compound shown by the following general formula (1E).

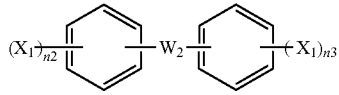
(1E)

(where $W_2$ represents a single bond or a divalent organic group, n2 and n3 represent integers that satisfy $2 \leq n2+n3 \leq 4$, the benzene rings in the formula optionally have a substituent thereon, and an organic group in $W_2$ and a substituent on the benzene ring optionally bond to each other to form a cyclic organic group; $X_1$ represents any of groups shown by the general formulae (1B) and (1C).

Further, in the inventive compound for forming an organic film, $W_2$ in the formula shown by the general formula (1E) preferably represents a single bond or the following (1F). Among these, from the viewpoints of providing solvent solubility and flowability, a single bond, or those having an ether bond, an isopropylidene structure, a hexafluoroisopropylidene structure, or a fluorene structure, and those which form an indane structure with an aromatic ring that bonds with an imide ring are preferable.

(1F)

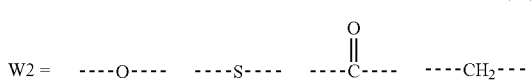

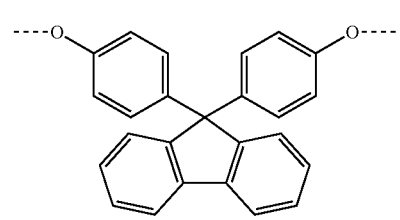

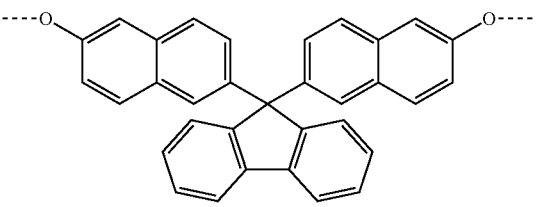

(where an aromatic ring in the above formula may have a substituent thereon.)

Furthermore, in the present invention, preferably, n2 and n3 in the general formula (1E) satisfy the relation $1 \leq n2 \leq 2$, $1 \leq n3 \leq 2$, $2 \leq n2+n3 \leq 4$, and the $X_1$ is a group represented by the following general formula (1G).

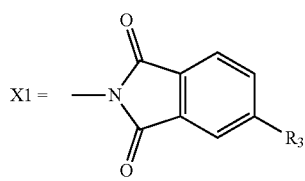

(1G)

(where $R_3$ represents any of groups shown by the following formula (1H), and two or more kinds of $R_3$ may be used in combination.)

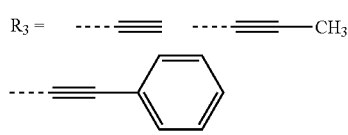

(1H)

When such relations of n2 and n3 are satisfied, the compound for forming an organic film does not lose thermosetting property and heat resistance, and has both filling and planarizing properties. In particular, compounds that satisfy $1 \leq n2 \leq 2$, $1 \leq n3 \leq 2$ and $3 \leq n2+n3 \leq 4$ are more preferable from the viewpoint of heat resistance.

The inventive compound for forming an organic film preferably satisfies $1.00 \leq Mw/Mn \leq 1.10$ where Mw is a weight average molecular weight and Mn is a number average molecular weight measured by gel permeation chromatography in terms of polystyrene. Controlling Mw/Mn of the compound for forming an organic film within such a range, an organic film excellent in filling property and planarization can be formed.

Even with a mixture of a monomolecular compounds including multiple terminal structures and main skeleton structures, when Mw/Mn is within the above range, thermal flowability of the compound for forming an organic film becomes even more favorable. Therefore, when blended in a composition, the compound can not only favorably fill a fine structure formed on a substrate but also form an organic film having the entire substrate planarized.

[Method for Manufacturing Compound for Forming Organic Film]

As a method for obtaining the inventive compound for forming an organic film, it is possible to synthesize the compound by obtaining an amic acid compound through the reaction of an amine compound and a phthalic anhydride derivative shown bellow (STEP 1), followed by thermal or chemical imidization (STEP 2-1). In this event, it is also possible to not perform the imidization and use the amic acid compound as it is as the compound for forming an organic film. The amine compound or the phthalic anhydride derivative used in the amic acid compound synthesis may be used alone or two or more kinds thereof may be used. These can be appropriately selected and combined according to required properties. $W_1$, $R_1$ and n1 in the following formulae have the same meanings as defined above.

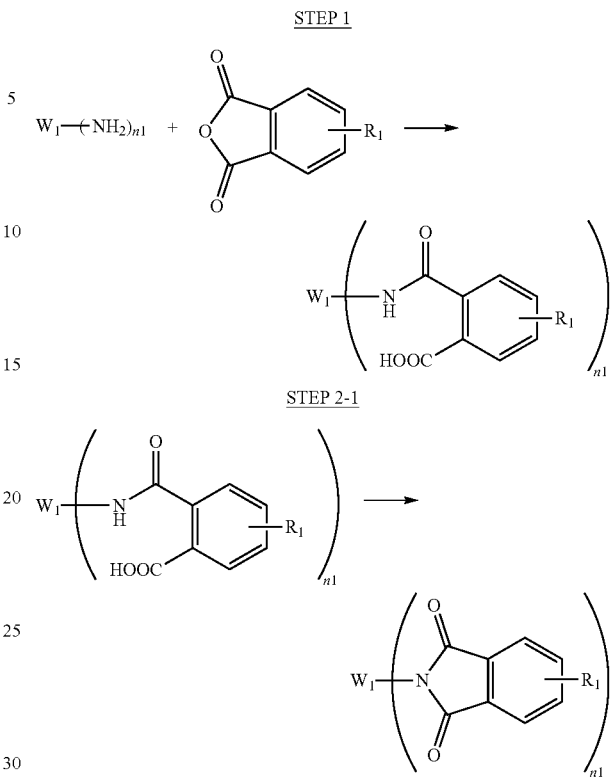

Synthesis of the amic acid compound shown by STEP 1 can generally be performed in an organic solvent at room temperature or under cooling or heating as necessary. Examples of the solvent used include alcohols such as methanol, ethanol, isopropyl alcohol, butanol, ethylene glycol, propylene glycol, diethylene glycol, glycerol, ethylene glycol monomethyl ether, propylene glycol monomethyl ether, and propylene glycol monoethyl ether; ethers such as diethyl ether, dibutyl ether, diethylene glycol diethyl ether, diethylene glycol dimethyl ether, tetrahydrofuran, and 1,4-dioxane; chlorinated solvents such as methylene chloride, chloroform, dichloroethane, and trichloroethylene; hydrocarbons such as hexane, heptane, benzene, toluene, xylene, and cumene; nitriles such as acetonitrile; ketones such as acetone, ethyl methyl ketone, isobutyl methyl ketone, and cyclohexanone; esters such as methyl acetate, ethyl acetate, n-butyl acetate, propylene glycol methyl ether acetate, and γ-butyrolactone; non-protic polar solvents such as N-methyl-2-pyrrolidone, N,N-dimethylacetamide, dimethylsulfoxide, N,N-dimethylformamide, and hexamethylphosphoric triamide; and the like. These can be used alone or in mixture of two or more thereof. These solvents can be used within a range of 0 to 2,000 parts by mass relative to 100 parts by mass of the reaction raw materials. The reaction temperature is preferably −50° C. to approximately the boiling point of the solvent, and room temperature to 150° C. is even more preferable. Reaction time is appropriately selected from 0.1 to 100 hours.

For these syntheses, a base catalyst can be used as necessary, and examples of the base catalyst include inorganic base compounds such as sodium hydrogen carbonate, sodium carbonate, potassium carbonate, calcium carbonate, cesium carbonate, sodium hydroxide, potassium hydroxide, sodium hydride, and potassium phosphate; organic bases such as triethyl amine, diisopropyl ethyl amine, N,N-dimethylaniline, pyridine, and 4-dimethylaminopyridine; and the like. These can be used alone or in combination of two or more thereof. The amount used is within the range of 0.01 to 20 moles relative to the number of moles of raw material phthalic anhydride derivative, preferably 0.05 to 10 moles.

The reaction method includes: a method in which the amine compound and the phthalic anhydride derivative are charged into the solvent at once; a method of charging a dispersed or dissolved amine compound and phthalic anhydride derivative separately or mixed by adding dropwise; a method in which either the amine compound or the phthalic anhydride derivative is dispersed or dissolved in the solvent, then the other dispersed or dissolved in the solvent is added dropwise to charge; and the like. Furthermore, when multiple amine compounds and phthalic anhydride derivatives are each charged, they can be mixed for reaction beforehand, or they can be made to react individually in succession. When a catalyst is used, methods include: a method in which the amine compound or the phthalic anhydride derivative is charged at once; a method in which the catalyst is dispersed or dissolved beforehand, then dropwise addition is performed; and the like. The obtained amic acid solution may proceed successively to the reaction of STEP 2-1 or STEP 2-2 described later. Furthermore, the obtained amic acid solution may be used directly as a compound for forming an organic film, and the resultant may be diluted with an organic solvent, then subjected to liquid separation and washing to remove unreacted raw materials, the catalyst, and so on present in the system, and thus collected.

The organic solvent used in the liquid separation and washing is not particularly limited, as long as the organic solvent is capable of dissolving the compounds and is separated into two layers when mixed with water. The organic solvent includes hydrocarbons such as hexane, heptane, benzene, toluene, and xylene; esters such as ethyl acetate, n-butyl acetate, and propylene glycol methyl ether acetate; ketones such as methyl ethyl ketone, methyl amyl ketone, cyclohexanone, and methyl isobutyl ketone; ethers such as diethyl ether, diisopropyl ether, methyl-tert-butyl ether, and ethylcyclopentylmethyl ether; chlorinated solvents such as methylene chloride, chloroform, dichloroethane, and trichloroethylene; mixtures thereof; and the like. As washing water used in this event, generally, what is called deionized water or ultrapure water may be used. The washing may be performed once or more, preferably approximately once to five times because washing ten times or more does not always produce the full washing effects thereof.

In the liquid separation and washing, the washing may be performed with a basic aqueous solution to remove the unreacted raw materials or acidic components in the system. The base specifically includes hydroxides of alkaline metals, carbonates of alkaline metals, hydroxides of alkali earth metals, carbonates of alkali earth metals, ammonia, organic ammonium, and the like.

Further, in the liquid separation and washing, the washing may be performed with an acidic aqueous solution to remove the unreacted raw materials, metal impurities, or basic components in the system. The acid specifically includes inorganic acids such as hydrochloric acid, hydrobromic acid, sulfuric acid, nitric acid, phosphoric acid, and heteropoly acid; organic acids such as oxalic acid, fumaric acid, maleic acid, trifluoroacetic acid, methanesulfonic acid, benzenesulfonic acid, p-toluenesulfonic acid, and trifluoromethanesulfonic acid; and the like.

The liquid separation and washing may be performed with any one of the basic aqueous solution and the acidic aqueous solution, or can be performed with a combination of the two. The liquid separation and washing is preferably performed with the basic aqueous solution and the acidic aqueous solution in this order from the viewpoint of removing the metal impurities.

After the liquid separation and washing with the basic aqueous solution and the acidic aqueous solution, washing with neutral water may be successively performed. The washing may be performed once or more, preferably approximately once to five times. As the neutral water, deionized water, ultrapure water, or the like as mentioned above may be used. The washing may be performed once or more, but if the washing is not performed sufficiently, the basic components and acidic components cannot be removed in some cases. The washing is preferably performed approximately once to five times because washing ten times or more does not always produce the full washing effects thereof.

Further, the reaction product after the liquid separation can also be collected as a powder by concentrating and drying the solvent or crystallizing the reaction product under reduced pressure or normal pressure. Alternatively, the reaction product can also be retained in the state of solution with an appropriate concentration to improve the workability in preparing the inventive material for forming an organic film. The concentration in this event is preferably 0.1 to 50 mass %, more preferably 0.5 to 30 mass %. With such a concentration, the viscosity is hardly increased, making it possible to prevent deterioration of the workability; in addition, since the amount of the solvent is not excessive, the solution can be prepared economically.

The solvent in this event is not particularly limited, as long as the solvent is capable of dissolving the compound. Specific examples of the solvent include ketones such as cyclohexanone and methyl-2-amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; and esters such as propylene glycol monomethyl ether acetate, propylene glycol monoethyl ether acetate, ethyl lactate, ethyl pyruvate, butyl acetate, methyl 3-methoxypropionate, ethyl 3-ethoxy propionate, tert-butyl acetate, tert-butyl propionate, and propylene glycol mono-tert-butyl ether acetate. These can be used alone or in mixture of two or more thereof.

The imide compound shown by STEP 2-1 can be synthesized by thermal or chemical imidization. These methods can be suitably selected according to the thermal stability of the linking group in the desired imide compound and the reactivity of the introduced substituent and the reagent used in the chemical imidization.

When a thermal imidization is performed, a solvent capable of forming an azeotrope with water is added to a reaction solution of the amic acid compound obtained in STEP 1 (dissolved in soluble solvent beforehand, if collected as a powder) and heated to 100° C. to 250° C., and a dehydrative cyclization reaction takes place while generated water is being removed to perform imidization.

As the solvent capable of forming an azeotrope with water, esters such as γ-butyrolactone; polar solvents such as N-methyl-2-pyrrolidone, N,N-dimethylacetamide, dimethylsulfoxide, and N,N-dimethylformamide; non-polar solvents such as benzene, toluene, xylene, and mesitylene; and the like can be used. It is preferable to heat these solvents individually or mixed, and perform dehydration while distilling the water generated by ring-closure out of the system.

These solvents can be used within a range of 0 to 2,000 parts by mass relative to 100 parts by mass of the reaction raw materials.

When a chemical imidization is performed, a base catalyst and an acid anhydride and the like as a dehydrating agent are added to a reaction solution of the amic acid compound obtained in STEP 1 (dissolved in soluble solvent beforehand, if collected as a powder) and heated to 0° C. to 120° C. to perform imidization.

Base catalysts used in the chemical imidization include pyridine, triethyl amine, trimethylamine, tributylamine, trioctylamine, and the like. Among these, pyridine is preferable, having suitable basicity for promoting the reaction. Dehydrating agents include acetic anhydride, trimellitic anhydride, pyromellitic anhydride, trifluoroacetic anhydride, polyphosphoric acid, phosphorus pentoxide, phosphorus pentachloride, and thionyl chloride. Acetic anhydride is preferable from the viewpoint of purification after the reaction. The amount of these catalysts used is within the range of 0.1 to 20 moles relative to the number of moles of raw material acid anhydride, preferably 0.2 to 10 moles. Furthermore, the base catalyst and the dehydrating agent may be used alone or in mixture of two or more thereof, and the imidization ratio thereof can be controlled appropriately according to the required performance of the target compound by adjusting the amount of the catalyst, the amount of the dehydrating agent, the reaction temperature, and the reaction time.

The solvent used in this event is not particularly limited, as long as the solvent is inactive in the above reaction. Examples of the solvent include ethers such as diethylene glycol diethyl ether, diethylene glycol dimethyl ether, tetrahydrofuran, and 1,4-dioxane; chlorinated solvents such as methylene chloride, chloroform, dichloroethane, and trichloroethylene; hydrocarbons such as hexane, heptane, benzene, toluene, xylene, and cumene; nitriles such as acetonitrile; ketones such as acetone, ethyl methyl ketone, isobutyl methyl ketone, and cyclohexanone; esters such as methyl acetate, ethyl acetate, n-butyl acetate, propylene glycol methyl ether acetate, and γ-butyrolactone; non-protic polar solvents such as N-methyl-2-pyrrolidone, N,N-dimethylacetamide, dimethylsulfoxide, N,N-dimethylformamide, and hexamethylphosphoric triamide; and the like. These can be used alone or in mixture. These solvents can be used within a range of 0 to 2,000 parts by mass relative to 100 parts by mass of the reaction raw materials.

As to the reaction method and the collection method for the compounds, the method explained in the description of the amic acid compound can be used.

For the synthesis of the amic acid or the imide compound, amine compound and phthalic anhydride derivative can be combined according to a required performance. Specifically, a substituent that contributes to improvement of solvent solubility, adhesion, and filling and planarizing properties, a substituent that contributes to etching resistance and film formation, and the like can be introduced according to the required performance that is desired. A material for forming an organic film using these compounds can achieve both higher filling and planarizing properties as well as higher heat resistance.

Furthermore, as shown below, the amic acid compound obtained in the above STEP 1 can be protected with an $R_2$ group according to the required performance such as provision of solvent solubility or flowability (STEP 2-2). The protected $R_2$ group undergoes dealcoholization accompanied by a ring closure reaction due to the heat treatment after film formation, and an imide ring is formed (STEP 3). $W_1$, $R_1$, $R_2$, and $n1$ in the following formulae have the same meanings as defined above, and $X_1$ represents a halogen, a tosyl group, or a mesyl group.

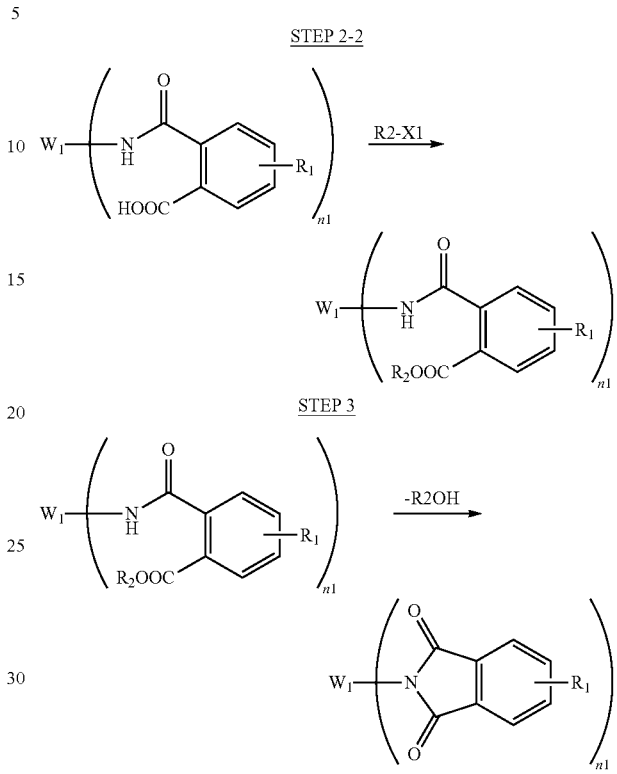

STEP 2-2 is not particularly limited, as long as the reaction enables introduction of $R_2$. Examples of the reaction include esterification reaction using a base catalyst with a halide, tosylate, or mesylate having $R_2$ as a partial structure.

The base catalyst used above includes inorganic base compounds such as sodium hydrogen carbonate, sodium carbonate, potassium carbonate, calcium carbonate, cesium carbonate, sodium hydroxide, potassium hydroxide, sodium hydride, and potassium phosphate; organic amine compounds such as triethyl amine, pyridine, and N-methylmorpholine; and the like. These can be used alone or in combination of two or more thereof. The amount of catalyst used is within the range of 0.1 to 20 moles relative to the number of moles of raw material amic acid, preferably, 0.2 to 10 moles.

The solvent used in this event is not particularly limited, as long as the solvent is inactive in the above reaction. Examples of the solvent include ether-based solvents such as diethyl ether, tetrahydrofuran, and dioxane; aromatic solvents such as benzene, toluene, and xylene; acetonitrile, dimethylsulfoxide, N,N-dimethylformamide, N-methylpyrrolidone, water, and the like. These can be used alone or in mixture. These solvents can be used within a range of 0 to 2,000 parts by mass relative to 100 parts by mass of the reaction raw materials. The reaction temperature is preferably −50° C. to approximately the boiling point of the solvent, and room temperature to 150° C. is even more preferable. Reaction time is appropriately selected from 0.1 to 100 hours.

As to the reaction method and the collection method for the compounds, the method explained in the description of the amic acid compound can be used.

In the above reaction, two or more kinds of R2-X1, or other halide, tosylate, and mesylate than R2-X1 can be combined according to a required performance. A side chain structure and the like for improving filling and planarizing properties and solvent solubility can be combined at a certain ratio.

As described above, the inventive compound for forming an organic film provides a material for forming an organic film having heat resistance to 400° C. or higher and high filling and planarizing properties.

Note that, in the present invention, the term planarizing property refers to a performance of planarizing the surface of a substrate. For example, as shown in FIG. 1, the material for forming an organic film containing the inventive compound for forming an organic film can reduce a 100-nm step of a substrate 1 to 30 nm or less by coating the substrate 1 with a material 3' for forming an organic film and heating the resultant to form an organic film 3. Note that the step profile shown in FIG. 1 represents a typical example of the step profile in a substrate for manufacturing a semiconductor device. It is a matter of course that the step profile of a substrate which can be planarized by the material for forming an organic film containing the inventive compound for forming an organic film is not limited thereto.

<Material for Forming Organic Film>

Further, the present invention provides a material for forming an organic film which is a composition for forming an organic film, containing: (A) the above-described inventive compound for forming an organic film and (B) an organic solvent. Note that in the inventive material for forming an organic film, the above-described inventive compound for forming an organic film can be used alone or in combination of two or more thereof.

The organic solvent that can be used in the inventive material for forming an organic film is not particularly limited as long as the solvent can dissolve the components contained in materials such as the above base polymer, an acid generator, a crosslinking agent, other additives, and the like. Specifically solvents with a boiling point of lower than 180° C. such as those disclosed in paragraphs (0091) to (0092) of Japanese Patent Laid-Open Publication No. 2007-199653 can be used. Above all, propylene glycol monomethyl ether acetate, propylene glycol monomethyl ether, 2-heptanone, cyclopentanone, cyclohexanone, and a mixture of two or more thereof are preferably used.

Such a material for forming an organic film can be applied by spin-coating, and has heat resistance to 400° C. or higher and high filling and planarizing properties because the inventive compound for forming an organic film as described above is incorporated.

Further, the inventive material for forming an organic film may use the organic solvent in which a high-boiling-point solvent having a boiling point of 180° C. or higher is added to the aforementioned solvent having a boiling point of lower than 180° C. (a mixture of the solvent having a boiling point of lower than 180° C. with the solvent having a boiling point of 180° C. or higher). The high-boiling-point organic solvent is not particularly limited to hydrocarbons, alcohols, ketones, esters, ethers, chlorinated solvents, and so forth, as long as the high-boiling-point organic solvent is capable of dissolving the compound for forming an organic film. Specific examples of the high-boiling-point organic solvent include 1-octanol, 2-ethylhexanol, 1-nonanol, 1-decanol, 1-undecanol, ethylene glycol, 1,2-propylene glycol, 1,3-butylene glycol, 2,4-pentanediol, 2-methyl-2,4-pentanediol, 2,5-hexanediol, 2,4-heptanediol, 2-ethyl-1,3-hexanediol, diethylene glycol, dipropylene glycol, triethylene glycol, tripropylene glycol, glycerin, n-nonyl acetate, ethylene glycol monohexyl ether, ethylene glycol mono-2-ethylhexyl ether, ethylene glycol monophenyl ether, ethylene glycol monobenzyl ether, diethylene glycol monoethyl ether, diethylene glycol monoisopropyl ether, diethylene glycol mono-n-butyl ether, diethylene glycol monoisobutyl ether, diethylene glycol monohexyl ether, diethylene glycol monophenyl ether, diethylene glycol monobenzyl ether, diethylene glycol diethyl ether, diethylene glycol dibutyl ether, diethylene glycol butylmethyl ether, triethylene glycol dimethyl ether, triethylene glycol monomethyl ether, triethylene glycol-n-butyl ether, triethylene glycol butylmethyl ether, triethylene glycol diacetate, tetraethylene glycol dimethyl ether, dipropylene glycol monomethyl ether, dipropylene glycol mono-n-propyl ether, dipropylene glycol mono-n-butyl ether, tripropylene glycol dimethyl ether, tripropylene glycol monomethyl ether, tripropylene glycol mono-n-propyl ether, tripropylene glycol mono-n-butyl ether, ethylene glycol monoethyl ether acetate, ethylene glycol monobutyl ether acetate, diethylene glycol monomethyl ether acetate, diethylene glycol monoethyl ether acetate, diethylene glycol monobutyl ether acetate, triacetin, propylene glycol diacetate, dipropylene glycol monomethyl ether acetate, dipropylene glycol methyl-n-propyl ether acetate, dipropylene glycol methyl ether acetate, 1,4-butanediol diacetate, 1,3-butylene glycol diacetate, 1,6-hexanediol diacetate, triethylene glycol diacetate, γ-butyrolactone, dihexyl malonate, diethyl succinate, dipropyl succinate, succinate dibutyl, succinate dihexyl, dimethyl adipate, diethyl adipate, dibutyl adipate, and the like. These may be used alone or in mixture thereof.

The boiling point of the high-boiling-point solvent may be appropriately selected according to the temperature at which the material for forming an organic film is heated. The boiling point of the high-boiling-point solvent to be added is preferably 180° C. to 300° C., more preferably 200° C. to 300° C. Such a boiling point prevents the evaporation rate at baking (heating) from becoming excessive, which would otherwise occur if the boiling point is too low. Thus, the boiling point of 180° C. or higher can provide sufficient thermal flowability. Meanwhile, with such a boiling point, the boiling point is not too high, so that the high-boiling-point solvent evaporates after baking and does not remain in the film; thus, the boiling point of 300° C. or lower does not adversely affect the film physical properties such as etching resistance.

When the high-boiling-point solvent is used, the formulation amount of the high-boiling-point solvent is preferably 1 to 30 parts by mass based on 100 parts by mass of the solvent having a boiling point of lower than 180° C. The formulation amount in this range prevents a failure in providing sufficient thermal flowability during baking, which would otherwise occur if the formulation amount is too small. In addition, deterioration of the film physical properties such as etching resistance is prevented, which would otherwise occur if the formulation amount is so large that the solvent remains in the film.

With such a material for forming an organic film, the above-described compound for forming an organic film is provided with thermal flowability by adding the high-boiling-point solvent, so that the material for forming an organic film also has high filling and planarizing properties.

In the inventive material for forming an organic film, (C) an acid generator can be added so as to further promote the curing reaction. The acid generator includes a material that generates an acid by thermal decomposition, and a material that generates an acid by light irradiation. Any acid generator can be added. Specifically, materials disclosed in paragraphs (0061) to (0085) of Japanese Patent Laid-Open Publication No. 2007-199653 can be added, but the present invention is not limited thereto.

The acid generators can be used alone or in combination of two or more thereof. When the acid generator is added, the added amount is preferably 0.05 to 50 parts, more preferably 0.1 to 10 parts, based on 100 parts of the compound for forming an organic film.

To the inventive material for forming an organic film, (D) a surfactant can be added so as to enhance the coating property in spin coating. Examples of the surfactant include those disclosed in (0142) to (0147) of Japanese Patent Laid-Open Publication No. 2009-269953 can be used.

Moreover, to the inventive material for forming an organic film, (E) a crosslinking agent can also be added so as to increase the curability and to further suppress intermixing with an upper layer film. The crosslinking agent is not particularly limited, and known various types of crosslinking agents can be widely used. Examples thereof include melamine-based crosslinking agents, glycoluril-based crosslinking agents, benzoguanamine-based crosslinking agents, urea-based crosslinking agents, β-hydroxyalkylamide-based crosslinking agents, isocyanurate-based crosslinking agents, aziridine-based crosslinking agents, oxazoline-based crosslinking agents, and epoxy-based crosslinking agents.

Specific examples of the melamine-based crosslinking agents include hexamethoxymethylated melamine, hexabutoxymethylated melamine, alkoxy- and/or hydroxy-substituted derivatives thereof, and partial self-condensates thereof. Specific examples of the glycoluril-based crosslinking agents include tetramethoxymethylated glycoluril, tetrabutoxymethylated glycoluril, alkoxy- and/or hydroxy-substituted derivatives thereof, and partial self-condensates thereof. Specific examples of the benzoguanamine-based crosslinking agents include tetramethoxymethylated benzoguanamine, tetrabutoxymethylated benzoguanamine, alkoxy- and/or hydroxy-substituted derivatives thereof, and partial self-condensates thereof. Specific examples of the urea-based crosslinking agents include dimethoxymethylated dimethoxyethyleneurea, alkoxy- and/or hydroxy-substituted derivatives thereof, and partial self-condensates thereof. A specific example of the β-hydroxyalkylamide-based crosslinking agents includes N,N,N',N'-tetra(2-hydroxyethyl)adipic acid amide. Specific examples of the isocyanurate-based crosslinking agents include triglycidyl isocyanurate and triallyl isocyanurate. Specific examples of the aziridine-based crosslinking agents include 4,4'-bis(ethyleneiminocarbonylamino)diphenylmethane and 2,2-bishydroxymethylbutanol-tris[3-(1-aziridinyl)propionate]. Specific examples of the oxazoline-based crosslinking agents include 2,2'-isopropylidene bis(4-benzyl-2-oxazoline), 2,2'-isopropylidene bis(4-phenyl-2-oxazoline), 2,2'-methylenebis4,5-diphenyl-2-oxazoline, 2,2'-methylenebis-4-phenyl-2-oxazoline, 2,2'-methylenebis-4-tert-butyl-2-oxazoline, 2,2'-bis(2-oxazoline), 1,3-phenylenebis(2-oxazoline), 1,4-phenylenebis(2-oxazoline), and a 2-isopropenyloxazoline copolymer. Specific examples of the epoxy-based crosslinking agents include diglycidyl ether, ethylene glycol diglycidyl ether, 1,4-butanediol diglycidyl ether, 1,4-cyclohexanedimethanol diglycidyl ether, poly(glycidyl methacrylate), trimethylolethane triglycidyl ether, trimethylolpropane triglycidyl ether, and pentaerythritol tetraglycidyl ether.

Further, to the inventive material for forming an organic film, (F) a plasticizer can be added so as to further enhance the planarizing and filling properties. The plasticizer is not particularly limited, and known various types of plasticizers can be widely used. Examples thereof include low-molecular-weight compounds such as phthalic acid esters, adipic acid esters, phosphoric acid esters, trimellitic acid esters, and citric acid esters; and polymers such as polyethers, polyesters, and polyacetal-based polymers disclosed in Japanese Patent Laid-Open Publication No. 2013-253227.

Particularly, like the plasticizer, as an additive for providing the inventive material for forming an organic film with filling and planarizing properties, it is preferable to use, for example, liquid additives having polyethylene glycol and polypropylene glycol structures, or thermo-decomposable polymers having a weight loss ratio between 30° C. and 250° C. of 40 mass % or more and a weight average molecular weight of 300 to 200,000. The thermo-decomposable polymers preferably contain a repeating unit having an acetal structure shown by the following general formula (DP1) or (DP1a).

(DP1)

(where $R_6$ represents a hydrogen atom or a saturated or unsaturated monovalent organic group having 1 to 30 carbon atoms which may be substituted. $Y_1$ represents a saturated or unsaturated divalent organic group having 2 to 30 carbon atoms.)

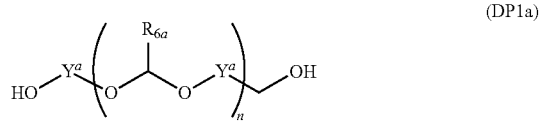
(DP1a)

(where $R_{6a}$ represents an alkyl group having 1 to 4 carbon atoms. $Y^a$ represents a saturated or unsaturated divalent hydrocarbon group having 4 to 10 carbon atoms which may have an ether bond. n represents an average repeating unit number of 3 to 500.)

As described above, the inventive material for forming an organic film is a material for forming an organic film having heat resistance to 400° C. or higher and high filling and planarizing properties. Thus, the inventive material for forming an organic film is extremely useful as an organic film material in multilayer resist methods such as a 2-layer resist method, a 3-layer resist method using a silicon-containing resist middle layer film or a silicon-containing inorganic hard mask, and a 4-layer resist method using a silicon-containing resist middle layer film or a silicon-containing inorganic hard mask and an organic antireflective film. Moreover, the inventive material for forming an organic film generates no by-product even during film formation in an inert gas, and has excellent filling and planarizing properties. Accordingly, the inventive material for forming an organic film can also be suitably used as a planarizing material in a semiconductor device manufacturing process, besides the multilayer resist methods.

Additionally, the present invention provides a substrate for manufacturing a semiconductor device, including an organic film on the substrate, the organic film being formed by curing the above-described material for forming an organic film.

The organic film of the present invention has both high filling and planarizing properties, and accordingly, the organic film does not have fine pores due to insufficient filling or asperity in the organic film surface due to insufficient planarizing property. A semiconductor device substrate planarized by the organic film of the present invention has an increased process margin at patterning, making it possible to manufacture semiconductor devices with high yields.

<Method for Forming Organic Film>

The film formation step by heating to form an organic underlayer film can employ 1-stage baking, 2-stage baking, or multi-stage baking of three or more stages. Nevertheless, the 1-stage baking or the 2-stage baking is economically preferable. The film formation by the 1-stage baking is, for example, performed at a temperature of 100° C. or higher to 600° C. or lower within a range of 5 to 3600 seconds, and preferably at a temperature of 150° C. or higher to 500° C. or lower within a range of 10 to 7200 seconds. Heating under such conditions can promote the planarization attributable to thermal flow and the crosslinking reaction. In a multilayer resist method, a coating-type silicon middle layer film or a CVD hard mask is sometimes formed on a film obtained as described above. In the case where a coating-type silicon middle layer film is employed, the film formation is performed preferably at a temperature higher than a temperature at which the silicon middle layer film is formed. Generally, a silicon middle layer film is formed at 100° C. or higher to 400° C. or lower, preferably 150° C. or higher to 350° C. or lower. Forming the organic underlayer film at a temperature higher than these temperatures makes it possible to prevent a composition for forming the silicon middle layer film from dissolving the organic underlayer film, and to form an organic film not mixed with the composition.

In the case where a CVD hard mask is employed, the organic underlayer film is formed preferably at a temperature higher than a temperature at which the CVD hard mask is formed. Examples of the temperature at which the CVD hard mask is formed include temperatures at 150° C. or higher to 500° C. or lower.

On the other hand, in the film formation by the 2-stage baking, the first baking is performed in air with a temperature having an upper limit of, for example, 300° C. or lower, preferably 250° C. or lower, within a range of 10 to 600 seconds, considering the influence of oxygen in air on the substrate corrosion. The second baking temperature is higher than the first baking temperature, and the second baking is performed at a temperature of 600° C. or lower, preferably 500° C. or lower, within a range of preferably 10 to 7200 seconds. In a multilayer resist method, a coating-type silicon middle layer film or a CVD hard mask is sometimes formed on a film obtained as described above. In the case where a coating-type silicon middle layer film is employed, the film formation is performed preferably at a temperature higher than a temperature at which the silicon middle layer film is formed. Generally, a silicon middle layer film is formed at 100° C. or higher to 400° C. or lower, preferably 150° C. or higher to 350° C. or lower. Forming the organic underlayer film at a temperature higher than these temperatures makes it possible to prevent a composition for forming the silicon middle layer film from dissolving the organic underlayer film, and to form an organic film not mixed with the composition.

In the case where a CVD hard mask is employed in the 2-stage baking, the organic underlayer film is formed preferably at a temperature higher than a temperature at which the CVD hard mask is formed. Examples of the temperature at which the CVD hard mask is formed include temperatures at 150° C. or higher to 500° C. or lower.

Furthermore, the present invention provides a method for forming an organic film that functions as an organic underlayer film used in a semiconductor device manufacturing process. In order to prevent corrosion of a substrate to be processed, the method includes heating the substrate to be processed under an atmosphere with an oxygen concentration of 1% or less thereby forming a cured film.

In this method for forming an organic film, for example, first of all, a substrate to be processed is spin-coated with the above-described inventive material for forming an organic film. After the spin coating, in the 2-stage baking, first, baking is performed in air at 300° C. or lower. Then, the second baking is performed under an atmosphere with an oxygen concentration of 1% or less. In the 1-stage baking, the first baking in air can be skipped. Note that examples of the atmosphere during the baking include such inert gases as nitrogen, argon, and helium. The inventive material for forming an organic film is capable of forming a sufficiently cured organic film without generating a sublimation product, even when the baking is performed under such an inert gas atmosphere.

Meanwhile, the inventive methods for forming an organic film make it possible to use a substrate to be processed having a structure or a step with a height of 30 nm or more. As described above, since the inventive material for forming an organic film is excellent in filling and planarizing properties, even when the substrate to be processed has a structure or a step (asperity) with a height of 30 nm or more, a flat cured film can be formed. Specifically, the inventive method for forming an organic film is particularly useful when a flat organic film is formed on such a substrate to be processed.

Note that the thickness of the organic film to be formed is appropriately selected, but is preferably 30 to 20,000 nm, particularly preferably 50 to 15,000 nm.

Additionally, the above-described methods for forming an organic film are applicable, using the inventive material for forming an organic film, to both cases where an organic film for an organic underlayer film is formed, and where an organic film for a flat film is formed.

The present invention provides a method for forming an organic film employed in a semiconductor device manufacturing process, the method including:

spin-coating a substrate to be processed with the above material for forming an organic film; and heating the substrate to be processed coated with the material for forming an organic film under an inert gas atmosphere at a temperature of 50° C. or higher to 600° C. or lower within a range of 10 seconds to 7200 seconds to obtain a cured film.

Further, the present invention provides a method for forming an organic film employed in a semiconductor device manufacturing process, the method including:

spin-coating a substrate to be processed with the above material for forming an organic film;

heating the substrate to be processed coated with the material for forming an organic film in air at a temperature of 50° C. or higher to 250° C. or lower within a range of 5 seconds to 600 seconds, preferably 10 to 600 seconds to form a coating film; and then heating under an inert gas atmosphere at a temperature of 200° C. or higher to 600° C. or lower, preferably 250° C. or higher within a range of 10 seconds to 7200 seconds to obtain a cured film.

An organic film employed in a semiconductor device manufacturing process formed by the inventive method has high heat resistance and high filling and planarizing properties, and allows a favorable semiconductor device yield when used in a semiconductor device manufacturing process.

In these methods for forming an organic film, first, a substrate to be processed is spin-coated with the above-described inventive material for forming an organic film. By employing the spin coating method, favorable filling property can be obtained. After the spin coating, baking (heating) is performed to promote the planarization attributable to thermal flow and the crosslinking reaction. Note that since this baking allows the solvent in the material for forming an organic film to evaporate, even when a resist upper layer film or a silicon-containing resist middle layer film is formed on the organic film, the mixing can be prevented.

<Patterning Processes>

[3-Layer Resist Method Using Silicon-Containing Resist Middle Layer Film]

The present invention provides a patterning process including:

forming an organic film on a body to be processed from the above material for forming an organic film;

forming a silicon-containing resist middle layer film on the organic film from a silicon-containing resist middle layer film material;

forming a resist upper layer film on the silicon-containing resist middle layer film from a photoresist composition;

forming a circuit pattern in the resist upper layer film;

transferring the pattern to the silicon-containing resist middle layer film by etching using the resist upper layer film having the formed pattern as a mask;

transferring the pattern to the organic film by etching using the silicon-containing resist middle layer film having the transferred pattern as a mask; and further transferring the pattern to the body to be processed by etching using the organic film having the transferred pattern as a mask.

As the body to be processed, it is preferable to use a semiconductor device substrate or the semiconductor device substrate coated with any of a metal film, a metal carbide film, a metal oxide film, a metal nitride film, a metal oxycarbide film, and a metal oxynitride film. More specifically, examples of the body which may be used include, but are not particularly limited to: substrates made of Si, α-Si, p-Si, $SiO_2$, SiN, SiON, W, TiN, Al, or the like; and these substrates coated with the above-described metal film or the like as a layer to be processed.

As the layer to be processed, used are various Low-k films made of Si, $SiO_2$, SiON, SiN, p-Si, α-Si, W, W—Si, Al, Cu, Al—Si, or the like, and stopper films thereof. The layer can be formed to have a thickness of generally 50 to 10,000 nm, particularly 100 to 5,000 nm. Note that when the layer to be processed is formed, the substrate and the layer to be processed are formed from different materials.

Note that the metal of the body to be processed is preferably silicon, titanium, tungsten, hafnium, zirconium, chromium, germanium, copper, silver, gold, aluminum, indium, gallium, arsenic, palladium, iron, tantalum, iridium, cobalt, manganese, molybdenum, or an alloy thereof.

Further, as the body to be processed, a substrate to be processed having a structure or a step with a height of 30 nm or more is preferably used.

When the organic film is formed on the body to be processed from the inventive material for forming an organic film, the above-described inventive methods for forming an organic film can be employed.

Next, using a resist middle layer film material containing silicon atoms, a resist middle layer film (silicon-containing resist middle layer film) is formed on the organic film. The silicon-containing resist middle layer film material is preferably a polysiloxane-based middle layer film material. The silicon-containing resist middle layer film having antireflective effect can suppress the reflection. Particularly, for 193-nm light exposure, a material containing many aromatic groups and having a high etching selectivity relative to the substrate is used as a material for forming an organic film, so that the k-value and thus the substrate reflection are increased; in contrast, the reflection can be suppressed by imparting absorption to the silicon-containing resist middle layer film so as to have an appropriate k-value, and the substrate reflection can be reduced to 0.5% or less. As the silicon-containing resist middle layer film having antireflective effect, a polysiloxane is preferably used which has anthracene for 248-nm and 157-nm light exposure, or a phenyl group or a light-absorbing group having a silicon-silicon bond for 193-nm light exposure in a pendant structure or a polysiloxane structure, and which is crosslinked by an acid or heat.

Next, using a resist upper layer film material composed of a photoresist composition, a resist upper layer film is formed on the silicon-containing resist middle layer film. The resist upper layer film material may be a positive type or a negative type, and any generally-used photoresist composition can be used. After the spin coating of the resist upper layer film material, pre-baking is preferably performed within ranges of 60 to 180° C. and 10 to 300 seconds. Then, light exposure, post-exposure bake (PEB), and development are performed according to conventional methods to obtain a resist upper layer film pattern. Note that the thickness of the resist upper layer film is not particularly limited, but is preferably 30 to 500 nm, particularly preferably 50 to 400 nm.

Next, a circuit pattern (the resist upper layer film pattern) is formed in the resist upper layer film. The circuit pattern is preferably formed by a lithography using light with a wavelength ranging from 10 nm or more to 300 nm or less, a direct drawing by electron beam, a nanoimprinting, or a combination thereof.

Note that the exposure light includes high energy beam with a wavelength of 300 nm or less; specifically, deep ultraviolet ray, KrF excimer laser beam (248 nm), ArF excimer laser beam (193 nm), $F_2$ laser beam (157 nm), $Kr_2$ laser beam (146 nm), $Ar_2$ laser beam (126 nm), soft X-ray (EUV) with a wavelength of 3 to 20 nm, electron beam (EB), ion beam, X-ray, and the like.

Additionally, in forming the circuit pattern, the circuit pattern is preferably developed by alkaline development or development with an organic solvent.

Next, using the resist upper layer film having the formed circuit pattern as a mask, the pattern is transferred to the silicon-containing resist middle layer film by etching. The etching of the silicon-containing resist middle layer film using the resist upper layer film pattern as a mask is preferably performed with a fluorocarbon-based gas. Thereby, a silicon-containing resist middle layer film pattern is formed.

Next, using the silicon-containing resist middle layer film having the transferred pattern as a mask, the pattern is transferred to the organic film by etching. Since the silicon-containing resist middle layer film exhibits higher etching resistance to an oxygen gas or a hydrogen gas than an organic compound, the etching of the organic film using the silicon-containing resist middle layer film pattern as a mask is preferably performed with an etching gas mainly containing an oxygen gas or a hydrogen gas. Thereby, an organic film pattern can be formed.

Next, using the organic film having the transferred pattern as a mask, the pattern is transferred to the body to be processed by etching. The subsequent etching of the body to be processed (layer to be processed) can be performed according to a conventional method. For example, the body to be processed made of $SiO_2$, SiN, or silica low-dielectric insulating film is etched mainly with a fluorocarbon-based gas. The body to be processed made of p-Si, Al, or W is etched mainly with a chlorine- or bromine-based gas. When the substrate is processed by etching with a fluorocarbon-based gas, the silicon-containing resist middle layer film pattern is removed together with the substrate processing. Meanwhile, when the substrate is processed by etching with a chlorine- or bromine-based gas, the silicon-containing resist middle layer film pattern needs to be removed by additional dry etching with a fluorocarbon-based gas after the substrate processing.

The organic film obtained from the inventive material for forming an organic film can exhibit excellent etching resistance when the body to be processed is etched as described above.

[4-Layer Resist Method Using Silicon-Containing Resist Middle Layer Film and Organic Antireflective Film]

Furthermore, the present invention provides a patterning process including:

forming an organic film on a body to be processed from the above material for forming an organic film;

forming a silicon-containing resist middle layer film on the organic film from a silicon-containing resist middle layer film material;

forming an organic antireflective film on the silicon-containing resist middle layer film;

forming a resist upper layer film on the organic antireflective film from a photoresist composition, so that a 4-layered film structure is constructed;

forming a circuit pattern in the resist upper layer film;

transferring the pattern to the organic antireflective film and the silicon-containing resist middle layer film by etching using the resist upper layer film having the formed pattern as a mask;

transferring the pattern to the organic film by etching using the silicon-containing resist middle layer film having the transferred pattern as a mask; and further transferring the pattern to the body to be processed by etching using the organic film having the transferred pattern as a mask.

Note that this method can be performed in the same manner as the above-described 3-layer resist method using the silicon-containing resist middle layer film, except that the organic antireflective film (BARC) is formed between the silicon-containing resist middle layer film and the resist upper layer film.

The organic antireflective film can be formed by spin coating from a known organic antireflective film material.

[3-Layer Resist Method Using Inorganic Hard Mask]

Furthermore, the present invention provides a patterning process including:

forming an organic film on a body to be processed from the above material for forming an organic film;

forming an inorganic hard mask selected from a silicon oxide film, a silicon nitride film, a silicon oxynitride film, a titanium oxide film, and a titanium nitride film on the organic film;

forming a resist upper layer film on the inorganic hard mask from a photoresist composition;

forming a circuit pattern in the resist upper layer film;

transferring the pattern to the inorganic hard mask by etching using the resist upper layer film having the formed pattern as a mask;

transferring the pattern to the organic film by etching using the inorganic hard mask having the transferred pattern as a mask; and further transferring the pattern to the body to be processed by etching using the organic film having the transferred pattern as a mask.

Note that this method can be performed in the same manner as the above-described 3-layer resist method using the silicon-containing resist middle layer film, except that the inorganic hard mask is formed in place of the silicon-containing resist middle layer film on the organic film.

The inorganic hard mask selected from a silicon oxide film, a silicon nitride film, and a silicon oxynitride film (SiON film) can be formed by a CVD method, an ALD method, or the like. The method for forming the silicon nitride film is disclosed in, for example, Japanese Patent Laid-Open Publication No. 2002-334869, International Publication No. 2004/066377, and so forth. The film thickness of the inorganic hard mask is preferably 5 to 200 nm, more preferably 10 to 100 nm. As the inorganic hard mask, a SiON film is most preferably used which is effective as an antireflective film. When the SiON film is formed, the substrate temperature reaches 300 to 500° C. Hence, the underlayer film needs to withstand the temperature of 300 to 500° C. Since the organic film formed from the inventive material for forming an organic film has high heat resistance and can withstand high temperatures of 300° C. to 500° C., this enables the combination of the inorganic hard mask formed by a CVD method or an ALD method with the organic film formed by a spin coating method.

[4-Layer Resist Method Using Inorganic Hard Mask and Organic Antireflective Film]

Furthermore, the present invention provides a patterning process including:

forming an organic film on a body to be processed from the above material for forming an organic film;

forming an inorganic hard mask selected from a silicon oxide film, a silicon nitride film, a silicon oxynitride film, a titanium oxide film, and a titanium nitride film on the organic film;

forming an organic antireflective film on the inorganic hard mask;

forming a resist upper layer film on the organic antireflective film from a photoresist composition, so that a 4-layered film structure is constructed;

forming a circuit pattern in the resist upper layer film;

transferring the pattern to the organic antireflective film and the inorganic hard mask by etching using the resist upper layer film having the formed pattern as a mask;

transferring the pattern to the organic film by etching using the inorganic hard mask having the transferred pattern as a mask; and further transferring the pattern to the body to be processed by etching using the organic film having the transferred pattern as a mask.

Note that this method can be performed in the same manner as the above-described 3-layer resist method using the inorganic hard mask, except that the organic antireflective film (BARC) is formed between the inorganic hard mask and the resist upper layer film.

Particularly, when the SiON film is used as the inorganic hard mask, two antireflective films including the SiON film and the BARC make it possible to suppress the reflection even in liquid immersion exposure at a high NA exceeding 1.0. Another merit of the BARC formation is having an effect of reducing footing of the resist upper layer film pattern immediately above the SiON film.

Herein, FIG. 2 (A) to (F) show an example of the inventive patterning process according to the 3-layer resist method. In the 3-layer resist method as shown in FIG. 2 (A), using the inventive material for forming an organic film, an organic film 3 is formed on a layer 2 to be processed formed on a substrate 1. Then, a silicon-containing resist middle layer film 4 is formed on the organic film 3, and a resist upper layer film 5 is formed on the silicon-containing resist middle layer film 4. Subsequently, as shown in FIG. 2 (B), an exposed portion 6 of the resist upper layer film 5 is exposed to light, followed by PEB (post-exposure bake). Thereafter, as shown in FIG. 2 (C), a resist upper layer film pattern 5a is formed by development. After that, as shown in FIG. 2 (D), using the resist upper layer film pattern 5a as a mask, the silicon-containing resist middle layer film 4 is processed by dry etching with a fluorocarbon-based gas. Thereby, a silicon-containing resist middle layer film pattern 4a is formed. Then, as shown in FIG. 2 (E), after the resist upper layer film pattern 5a is removed, the organic film 3 is etched with oxygen plasma using the silicon-containing resist middle layer film pattern 4a as a mask. Thereby, an organic film pattern 3a is formed. Further, as shown in FIG. 2 (F), after the silicon-containing resist middle layer film pattern 4a is removed, the layer to be processed 2 is processed by etching using the organic film pattern 3a as a mask. Thus, a pattern 2a is formed.

In the case where an inorganic hard mask is formed, the silicon-containing resist middle layer film 4 may be replaced with the inorganic hard mask. In the case where a BARC is formed, the BARC may be formed between the silicon-containing resist middle layer film 4 and the resist upper layer film 5. The BARC may be etched continuously and before the etching of the silicon-containing resist middle layer film 4. Alternatively, after the BARC is etched alone, the silicon-containing resist middle layer film 4 may be etched, for example, after an etching apparatus is changed.

As described above, the inventive patterning processes make it possible to precisely form a fine pattern in a body to be processed by the multilayer resist methods.

EXAMPLE

Hereinafter, the present invention will be more specifically described by referring to Synthesis Examples, Comparative Synthesis Examples, Examples, and Comparative Examples. However, the present invention is not limited thereto. Note that, with respect to molecular weight and dispersity, weight average molecular weight (Mw) and number average molecular weight (Mn) were measured by gel permeation chromatography (GPC) using tetrahydrofuran as an eluent in terms of polystyrene, and dispersity (Mw/Mn) was calculated therefrom.

Synthesis Examples: Synthesis of Compounds Used in Organic Film Material

Compounds (A1) to (A24) used in an organic film material were synthesized using amine compounds: (B1) to (B15) and phthalic anhydride derivatives: (C1) to (C3) shown below. For (B10), a 60:40 isomeric mixture was used.
Amine Compounds:

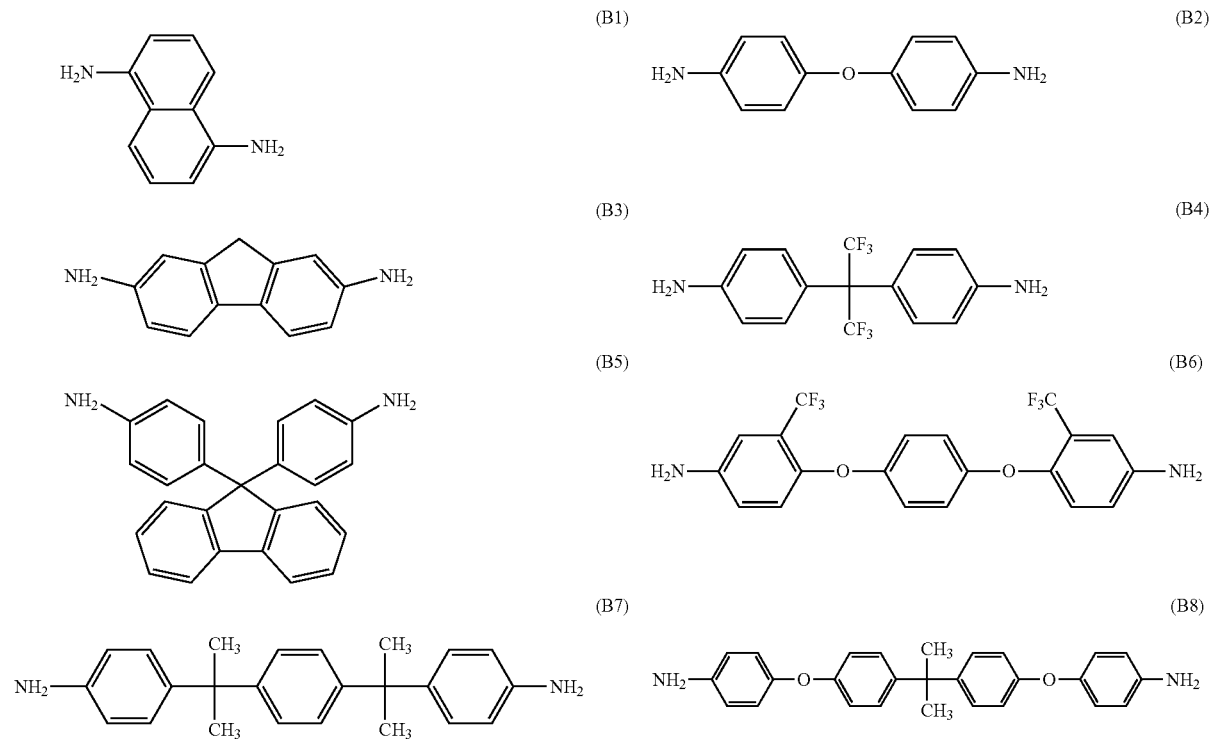

-continued

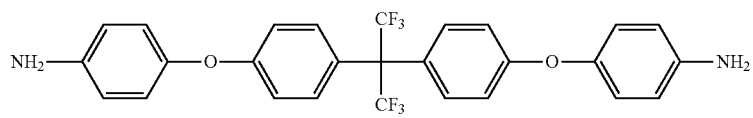
(B9)

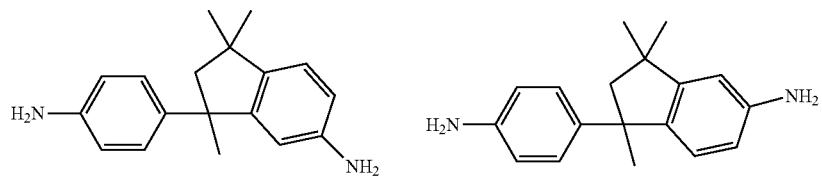
(B10)

60:40

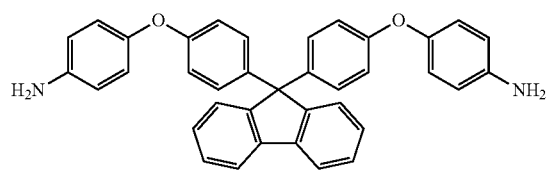
(B11)

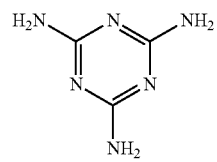
(B12)

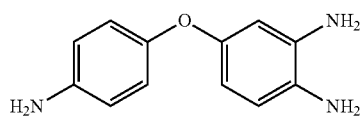
(B13)

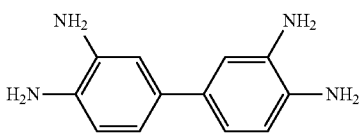
(B14)

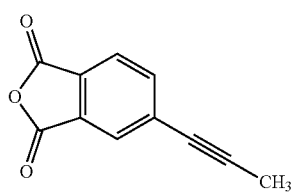
(B15)

Phthalic Anhydride Derivatives:

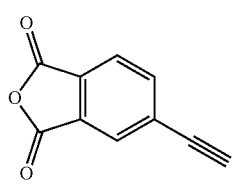
(C1)

-continued

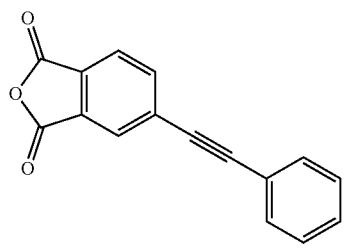
(C3)

(C2)

For example, in the case where an amine compound (B1) and a phthalic anhydride derivative (C1) are used to manufacture an amic acid compound, the following three types of isomeric structure in chemical formulae (1) to (3) are possible. Therefore, for amic acid compounds in the present Example and amic acid ester compounds derived from an amic acid having a similar isomeric structure, one kind of isomeric structure has been expressed as a representative structure.

(1)

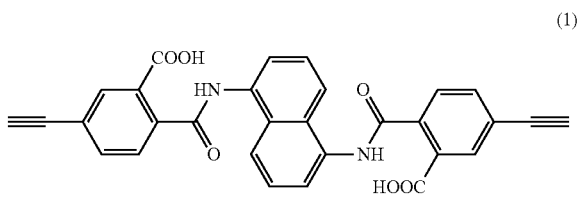

(2)

(3)

[Synthesis Example 1] Synthesis of Compound (A1)

120 g of NMP (N-methyl-2-pyrrolidone) was added to 7.91 g of amine compound (B1) and 17.21 g of phthalic anhydride derivative (C1), and under a nitrogen atmosphere, the reaction was allowed to proceed at an inner temperature of 40° C. for 3 hours to obtain an amic acid solution. 3.96 g of pyridine was added to the obtained amic acid solution, and 12.26 g of acetic anhydride was further added dropwise slowly. Then, the reaction was allowed to proceed at an inner temperature of 60° C. for 4 hours for imidization. After completion of the reaction, the solution was cooled to room temperature, 300 g of methyl isobutyl ketone was added, and the organic layer was washed with 100 g of 3% nitric acid aqueous solution. Then, the organic layer was further washed five times with 100 g of pure water and was evaporated under reduced pressure to dryness. To the residue, 100 g of THF (tetrahydrofuran) was added, and a homogeneous solution was formed. Thereafter, a crystal was precipitated with 300 g of methanol. The precipitated crystal was separated by filtration, washed twice with 200 g of methanol, and collected. The collected crystal was vacuum dried at 70° C. Thus, (A1) was obtained.

When the weight average molecular weight (Mw) and dispersity (Mw/Mn) were measured by GPC, the following results were obtained.

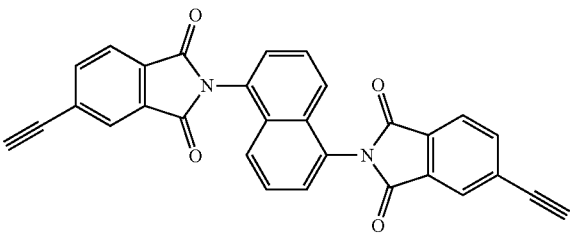

(A1) : Mw = 450, Mw/Mn = 1.01

[Synthesis Examples 2 to 13] Synthesis of Compounds (A2) to (A13)

Compounds (A2) to (A13) as shown in Table 1 were obtained as products under the same reaction conditions as those in Synthesis Example 1, except that the amine compounds and the phthalic anhydride derivative shown in Table 1 were used.

TABLE 1

| Synthesis Example | Amine compound | Phthalic anhydride derivative | Product |
|---|---|---|---|
| 1 | B1: 7.91 g | C1: 17.21 g | A1 |
| 2 | B2: 10.01 g | C2: 18.62 g | A2 |
| 3 | B3: 7.85 g | C3: 19.86 g | A3 |
| 4 | B4: 13.37 g | C1: 6.89 g | A4 |
|   |   | C3: 9.93 g |   |
| 5 | B5: 13.94 g | C1: 13.77 g | A5 |
| 6 | B6: 17.13 g | C2: 14.89 g | A6 |
| 7 | B7: 13.78 g | C1: 13.77 g | A7 |
| 8 | B8: 12.32 g | C3: 14.89 g | A8 |
| 9 | B9: 15.55 g | C1: 10.33 g | A9 |
| 10 | B10: 13.32 g | C1: 17.21 g | A10 |
| 11 | B10: 10.66 g | C3: 19.86 g | A11 |
| 12 | B11: 15.98 g | C1: 10.33 g | A12 |
| 13 | B11: 15.98 g | C3: 14.89 g | A13 |

[Synthesis Example 14] Synthesis of Compound (A14)

120 g of NMP was added to 15.98 g of amine compound (B11) and 10.33 g of phthalic anhydride derivative (C1), and under a nitrogen atmosphere, the reaction was allowed to proceed at an inner temperature of 40° C. for 3 hours to obtain an amic acid solution. After completion of the reaction, the solution was cooled to room temperature, 300 g of methyl isobutyl ketone was added, and the organic layer was washed with 100 g of 3% nitric acid aqueous solution. Then, the organic layer was further washed five times with 100 g of pure water and was evaporated under reduced pressure to dryness. To the residue, 100 g of THF was added, and a homogenous solution was formed. Thereafter, a crystal was precipitated in 300 g of hexane. The precipitated crystal was separated by filtration, washed twice with 200 g of hexane, and collected. The collected crystal was vacuum dried at 70° C. Thus, (A14) was obtained.

When the weight average molecular weight (Mw) and dispersity (Mw/Mn) were measured by GPC, the following results were obtained.

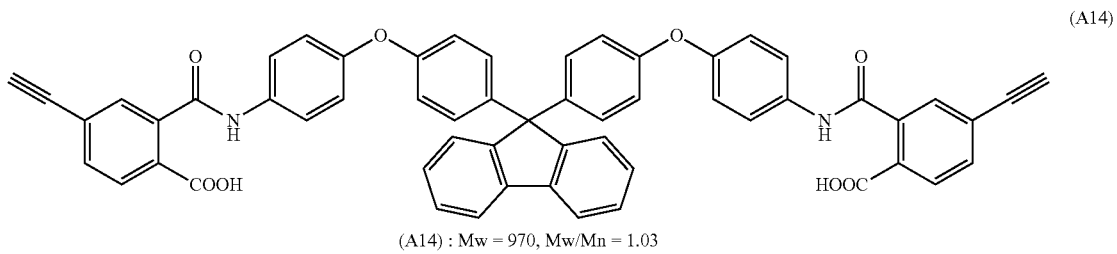 [SMILES: C#Cc1ccc(C(=O)O)c(C(=O)Nc2ccc(Oc3ccc(C4(c5ccc(Oc6ccc(NC(=O)c7cc(C#C)ccc7C(=O)O)cc6)cc5)c5ccccc5-c5ccccc54)cc3)cc2)c1]

(A14) : Mw = 970, Mw/Mn = 1.03

[Synthesis Example 15] Synthesis of Compound (A15)

A homogeneous dispersion was formed from 10.00 g of the compound (A14), 4.16 g of potassium carbonate, and 50 g of NMP under a nitrogen atmosphere at an inner temperature of 50° C. 3.75 g of n-butyl bromide was slowly added dropwise, and the reaction was allowed to proceed at an inner temperature of 50° C. for 16 hours. After cooling to room temperature, 100 g of methyl isobutyl ketone and 50 g of pure water were added for homogenization, then, the aqueous layer was removed. Further, the organic layer was washed twice with 30 g of a 3.0% nitric acid aqueous solution and five times with 30 g of pure water. The organic layer was evaporated under reduced pressure to dryness. To the residue, 30 g of THF was added, and a crystal was precipitated with 100 g of methanol. The precipitated crystal was separated by filtration, washed twice with 60 g of methanol, and collected. The collected crystal was vacuum dried at 70° C. Thus, (A15) was obtained.

When the weight average molecular weight (Mw) and dispersity (Mw/Mn) were measured by GPC, the following results were obtained.

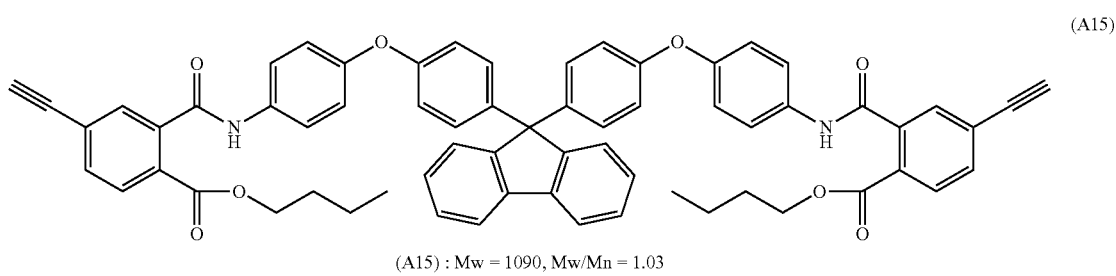 [SMILES: C#Cc1ccc(C(=O)OCCCC)c(C(=O)Nc2ccc(Oc3ccc(C4(c5ccc(Oc6ccc(NC(=O)c7cc(C#C)ccc7C(=O)OCCCC)cc6)cc5)c5ccccc5-c5ccccc54)cc3)cc2)c1]

(A15) : Mw = 1090, Mw/Mn = 1.03

[Synthesis Example 16] Synthesis of Compound (A16)

With 3.00 g of amine compound (B12), 17.71 g of phthalic anhydride derivative (C3), 8.30 g of triethyl amine, and 100 g of NMP, reaction was allowed to proceed under a nitrogen atmosphere at an inner temperature of 40° C. for 3 hours to obtain an amic acid solution. 12.03 g of acetic anhydride was added slowly to the obtained amic acid solution dropwise. Then, the reaction was allowed to proceed at an inner temperature of 60° C. for 4 hours for imidization. After completion of the reaction, the solution was cooled to room temperature, and the reaction solution was added to 500 g of methanol to precipitate a crystal. The precipitated crystal was separated by filtration, washed twice with 300 g of methanol, and collected. The collected crystal was vacuum dried at 70° C. Thus, (A16) was obtained.

When the weight average molecular weight (Mw) and dispersity (Mw/Mn) were measured by GPC, the following results were obtained.

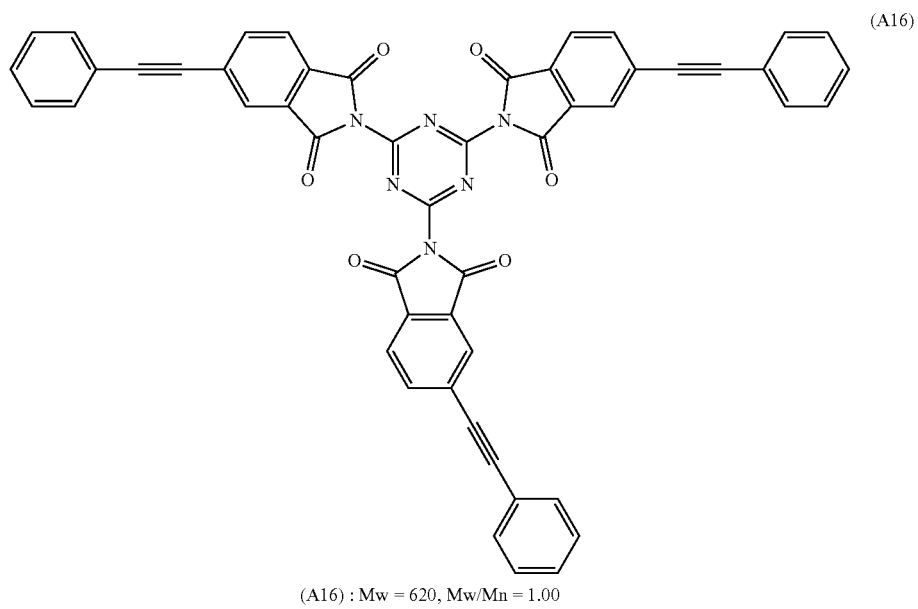 [SMILES: O=C1c2ccc(C#Cc3ccccc3)cc2C(=O)N1c1nc(N2C(=O)c3ccc(C#Cc4ccccc4)cc3C2=O)nc(N2C(=O)c3ccc(C#Cc4ccccc4)cc3C2=O)n1]

(A16)

(A16) : Mw = 620, Mw/Mn = 1.00

[Synthesis Example 17] Synthesis of Compound (A17)

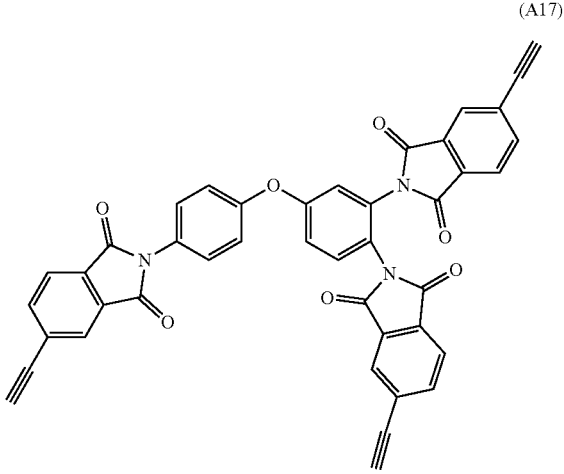

(A17)

(A17) : Mw = 790, Mw/Mn = 1.01

120 g of NMP was added to 8.61 g of amine compound (B13) and 20.66 g of phthalic anhydride derivative (C1), and under a nitrogen atmosphere, the reaction was allowed to proceed at an inner temperature of 40° C. for 3 hours to obtain an amic acid solution. 4.75 g of pyridine was added to the obtained amic acid solution, and 14.72 g of acetic anhydride was further added dropwise slowly. Then, the reaction was allowed to proceed at an inner temperature of 60° C. for 4 hours for imidization. After completion of the reaction, the solution was cooled to room temperature, 300 g of methyl isobutyl ketone was added, and the organic layer was washed with 100 g of 3% nitric acid aqueous solution. Then, the organic layer was further washed five times with 100 g of pure water and was evaporated under reduced pressure to dryness. To the residue, 100 g of THF was added, and a homogeneous solution was formed. Thereafter, a crystal was precipitated with 300 g of hexane. The precipitated crystal was separated by filtration, washed twice with 200 g of hexane, and collected. The collected crystal was vacuum dried at 70° C. Thus, (A17) was obtained.

When the weight average molecular weight (Mw) and dispersity (Mw/Mn) were measured by GPC, the following results were obtained.

[Synthesis Example 18] Synthesis of Compound (A18)

120 g of NMP was added to 4.54 g of amine compound (B14) and 20.66 g of phthalic anhydride derivative (C1), and under a nitrogen atmosphere, the reaction was allowed to proceed at an inner temperature of 40° C. for 3 hours to obtain an amic acid solution. 4.75 g of pyridine was added to the obtained amic acid solution, and 14.72 g of acetic anhydride was further added dropwise slowly. Then, the reaction was allowed to proceed at an inner temperature of 60° C. for 4 hours for imidization. After completion of the reaction the solution was cooled to room temperature, 300 g of methyl isobutyl ketone was added, and the organic layer was washed with 100 g of 3% nitric acid aqueous solution. Then, the organic layer was further washed five times with 100 g of pure water and was evaporated under reduced pressure to dryness. To the residue, 100 g of THF was added, and a homogeneous solution was formed. Thereafter, a crystal was precipitated with 300 g of hexane. The precipitated crystal was separated by filtration, washed twice with 200 g of hexane, and collected. The collected crystal was vacuum dried at 70° C. Thus, (A18) was obtained.

When the weight average molecular weight (Mw) and dispersity (Mw/Mn) were measured by GPC, the following results were obtained.

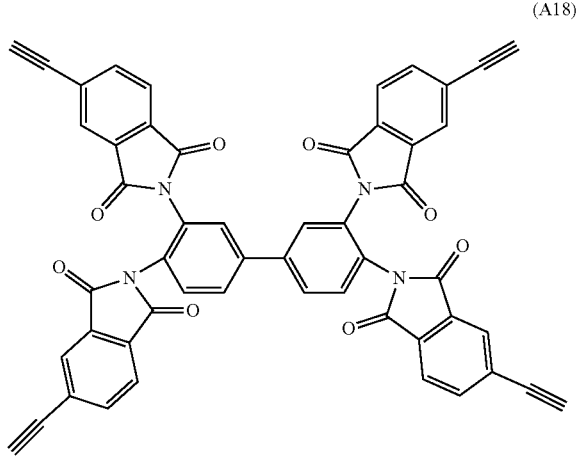

(A18) : Mw = 940, Mw/Mn = 1.00

[Synthesis Example 19] Synthesis of Compound (A19)

120 g of NMP was added to 3.78 g of amine compound (B14) and 24.82 g of phthalic anhydride derivative (C3), and under a nitrogen atmosphere, the reaction was allowed to proceed at an inner temperature of 40° C. for 3 hours to obtain an amic acid solution. 3.96 g of pyridine was added to the obtained amic acid solution, and 12.26 g of acetic anhydride was further added dropwise slowly. Then, the reaction was allowed to proceed at an inner temperature of 60° C. for 4 hours for imidization. After completion of the reaction, the solution was cooled to room temperature, 300 g of methyl isobutyl ketone was added, and the organic layer was washed with 100 g of 3% nitric acid aqueous solution. Then, the organic layer was further washed six times with 100 g of pure water and was evaporated under reduced pressure to dryness. After a homogeneous solution was formed by adding 100 g of THF to the residue, a crystal was precipitated with 300 g of diisopropyl ether. The precipitated crystal was separated by filtration, washed twice with 200 g of diisopropyl ether, and collected. The collected crystal was vacuum dried at 70° C. Thus, (A19) was obtained.

When the weight average molecular weight (Mw) and dispersity (Mw/Mn) were measured by GPC, the following results were obtained.

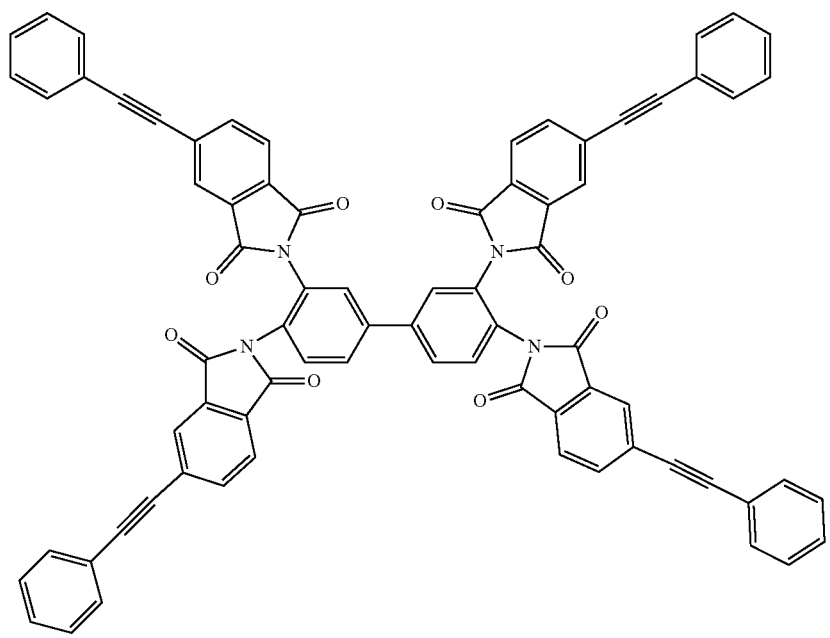

(A19) : Mw = 1200, Mw/Mn = 1.01

[Synthesis Example 20] Synthesis of Compound (A20)

120 g of NMP was added to 11.41 g of amine compound (B15) and 14.89 g of phthalic anhydride derivative (C3), and under a nitrogen atmosphere, the reaction was allowed to proceed at an inner temperature of 40° C. for 3 hours to obtain an amic acid solution. 130 g of o-xylene was added to the obtained amic acid solution, and while removing the generated water from the system under an inner temperature of 180° C., the reaction was allowed to proceed for 9 hours for imidization. After completion of the reaction, the solution was cooled to room temperature and a crystal was precipitated in 600 g of diisopropyl ether. The precipitated crystal was separated by filtration, washed twice with 200 g of diisopropyl ether, and collected. The collected crystal was vacuum dried at 70° C. Thus, (A20) was obtained.

When the weight average molecular weight (Mw) and dispersity (Mw/Mn) were measured by GPC, the following results were obtained.

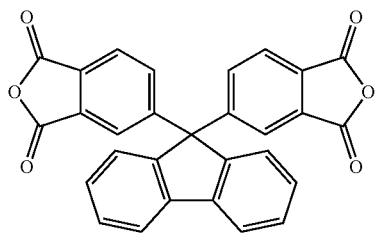

(D4)

[Synthesis Example 21] Synthesis of Compound (A21)

A homogeneous dispersion was formed from 10.00 g of the compound (D1), 4.76 g of potassium carbonate, and 50 g of N-methyl-2-pyrrolidone under a nitrogen atmosphere at an inner temperature of 50° C. 3.72 g of propargyl bromide

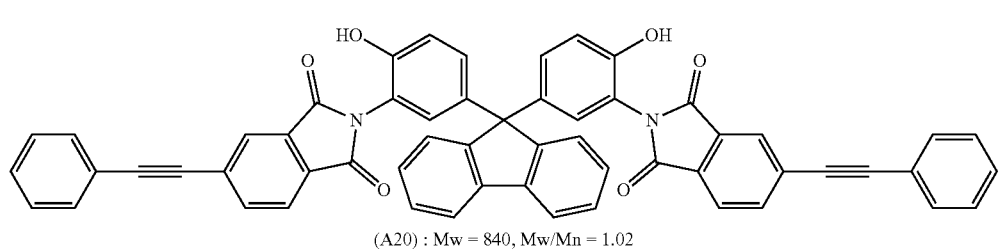

(A20) : Mw = 840, Mw/Mn = 1.02

Compounds (A21) to (A24) used in an organic film material were synthesized using the compounds (D1) to (D4) shown below and the above-described (B5) and (B11).

was slowly added dropwise, and the reaction was allowed to proceed at an inner temperature of 50° C. for 16 hours. After cooling to room temperature, a homogeneous solution was formed by adding 100 g of methyl isobutyl ketone and 50 g of pure water, then, the aqueous layer was removed. Further, the organic layer was washed twice with 30 g of a 3.0% nitric acid aqueous solution and five times with 30 g of pure water. The organic layer was evaporated under reduced pressure to dryness. To the residue, 30 g of THF was added, and a crystal was precipitated with 100 g of methanol. The precipitated crystal was separated by filtration, washed twice with 60 g of methanol, and collected. The collected crystal was vacuum dried at 70° C. Thus, (A21) was obtained.

When the weight average molecular weight (Mw) and dispersity (Mw/Mn) were measured by GPC, the following results were obtained.

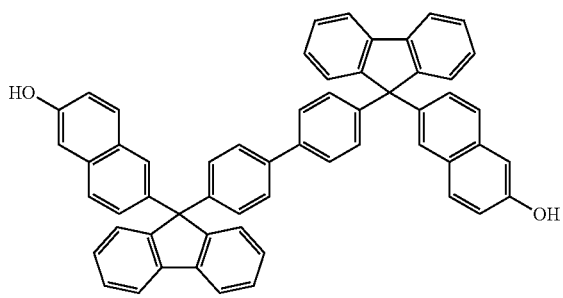

(D1)

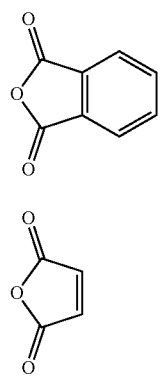

(D2)

(D3)

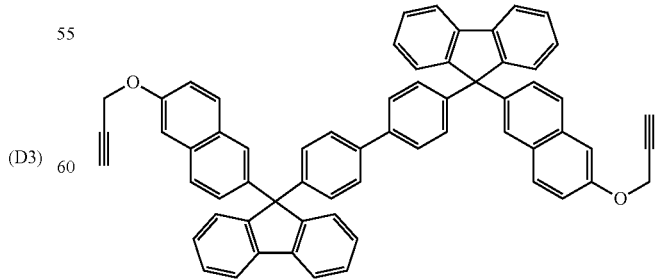

(A21) : Mw = 960, Mw/Mn = 1.07

[Synthesis Example 22] Synthesis of Compound (A22)

120 g of NMP was added to 15.98 g of amine compound (B11) and 8.89 g of the compound (D2), and under a nitrogen atmosphere, the reaction was allowed to proceed at an inner temperature of 40° C. for 3 hours to obtain an amic acid solution. 130 g of o-xylene was added to the obtained amic acid solution, and while removing the generated water from the system under an inner temperature of 180° C., the reaction was allowed to proceed for 9 hours for imidization. After cooling to room temperature, 200 g of methyl isobutyl ketone and 100 g of pure water were added for homogenization, then, the aqueous layer was removed. Further, the organic layer was washed five times with 100 g of 3.0% nitric acid aqueous solution and 100 g of pure water, and was evaporated under reduced pressure to dryness. To the residue, 100 g of THF was added, and a crystal was precipitated with 300 g of methanol. The precipitated crystal was separated by filtration, washed twice with 200 g of methanol, and collected. The collected crystal was vacuum dried at 70° C. Thus, (A22) was obtained.

When the weight average molecular weight (Mw) and dispersity (Mw/Mn) were measured by GPC, the following results were obtained.

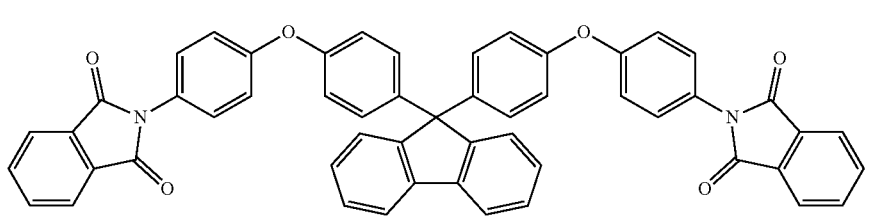

(A22) : Mw = 780, Mw/Mn = 1.01

[Synthesis Example 23] Synthesis of Compound (A23)

100 g of acetone was added to 15.98 g of amine compound (B11) and 5.88 g of the compound (D3), and reaction was allowed to proceed under a nitrogen atmosphere at an inner temperature of 40° C. for 3 hours. 2.46 g of sodium acetate and 15.33 g of acetic anhydride were slowly added dropwise to the obtained reaction solution, then, the reaction was allowed to proceed at an inner temperature of 50° C. for 4 hours. After completion of the reaction, the solution was cooled to room temperature, 300 g of methyl isobutyl ketone was added, and the organic layer was washed with 100 g of a 3% nitric acid aqueous solution. Then, the organic layer was further washed six times with 100 g of pure water and was evaporated under reduced pressure to dryness. To the residue, 100 g of the THF was added, and a homogeneous solution was formed. Thereafter a crystal was precipitated with 300 g of diisopropyl ether. The precipitated crystal was separated by filtration, washed twice with 200 g of diisopropyl ether, and collected. The collected crystal was vacuum dried at 70° C. Thus, (A23) was obtained.

When the weight average molecular weight (Mw) and dispersity (Mw/Mn) were measured by GPC, the following results were obtained.

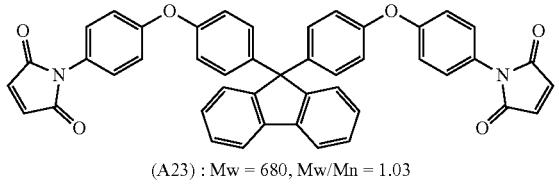

(A23) : Mw = 680, Mw/Mn = 1.03

[Synthesis Example 24] Synthesis of Compound (A24)

Under a nitrogen atmosphere, after dissolving 13.98 g of an amine compound (B5) in 192 g of NMP, 11.46 g of the compound (D4) was added, and reaction was allowed to proceed at an inner temperature of 40° C. for 2 hours. Further, 4.44 g of the compound (D2) was added and the reaction was allowed to proceed for a further 2 hours. 3.16 g of pyridine was added to the obtained amic acid solution, and 10.22 g of acetic anhydride was further added dropwise slowly. Then, the reaction was allowed to proceed at an inner temperature of 60° C. for 4 hours for imidization. The solution was cooled to room temperature and a crystal was precipitated in 600 g of methanol. The precipitated crystal was separated by filtration, washed twice with 200 g of methanol, and collected. The collected crystal was vacuum dried at 70° C. Thus, (A24) was obtained.

When the weight average molecular weight (Mw) and dispersity (Mw/Mn) were measured by GPC, the following results were obtained.

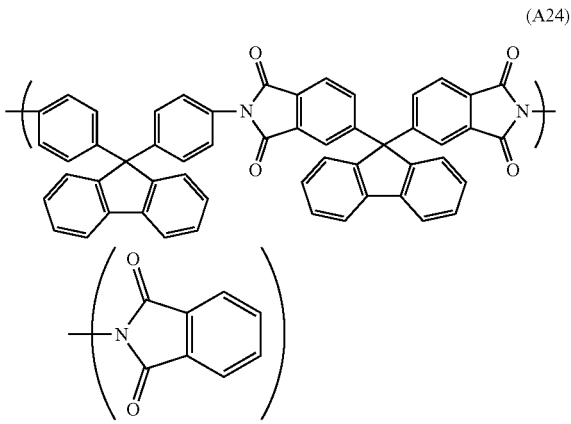

(A24) : Mw = 4500, Mw/Mn = 1.28

The structural formula, weight average molecular weight (Mw), and dispersity (Mw/Mn) of the compounds obtained above are listed in Tables 2-1 to 2-4. Additionally Mw and Mw/Mn of the compound (D1) used in Comparative Examples are also shown in Table 2-4.

TABLE 2-1
| Synthesis Example | Compound | | Mw | Mw/Mn |
|---|---|---|---|---|
| 1 | (A1) | 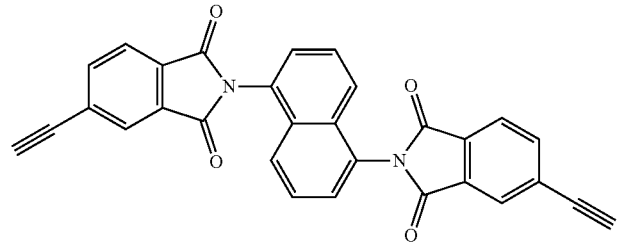 [SMILES: C#Cc1ccc2c(c1)C(=O)N(c1cccc3c(N4C(=O)c5ccc(C#C)cc5C4=O)cccc13)C2=O] | 450 | 1.01 |
| 2 | (A2) | 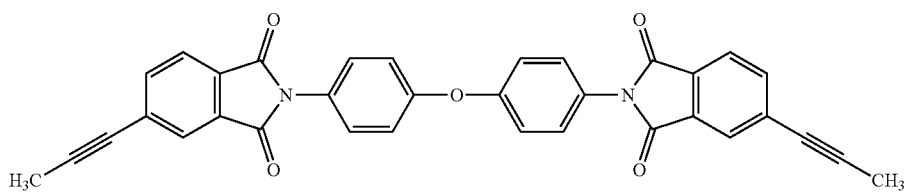 [SMILES: CC#Cc1ccc2c(c1)C(=O)N(c1ccc(Oc3ccc(N4C(=O)c5ccc(C#CC)cc5C4=O)cc3)cc1)C2=O] | 540 | 1.01 |
| 3 | (A3) | 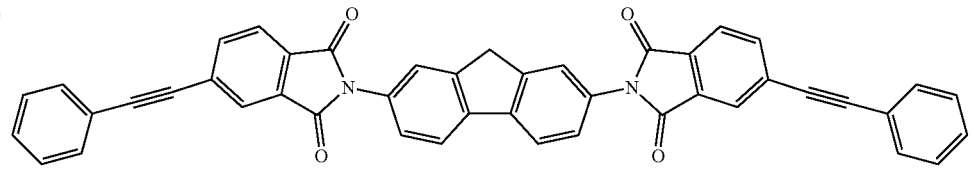 [SMILES: O=C1c2ccc(C#Cc3ccccc3)cc2C(=O)N1c1ccc2c(c1)Cc1cc(N3C(=O)c4ccc(C#Cc5ccccc5)cc4C3=O)ccc1-2] | 740 | 1.01 |
| 4 | (A4) | 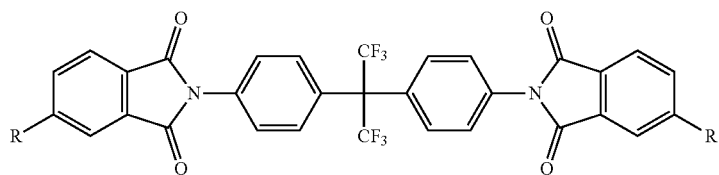<br>R = 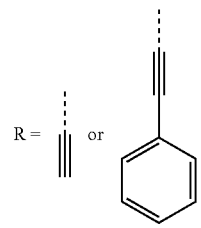<br>50:50 | 790 | 1.05 |
| 5 | (A5) | 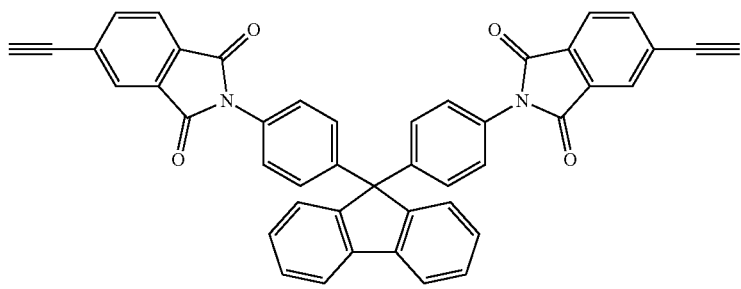 [SMILES: C#Cc1ccc2c(c1)C(=O)N(c1ccc(C3(c4ccc(N5C(=O)c6ccc(C#C)cc6C5=O)cc4)c4ccccc4-c4ccccc43)cc1)C2=O] | 690 | 1.03 |

TABLE 2-1-continued
| Synthesis Example | Compound | Mw | Mw/Mn |
|---|---|---|---|
| 6 | (A6) 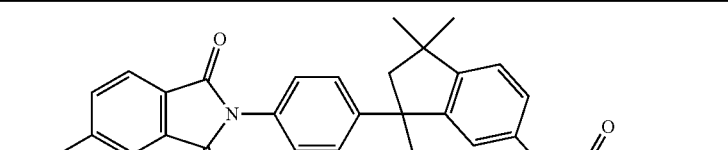 | 740 | 1.02 |
| 7 | (A7) | 640 | 1.01 |
| 8 | (A8) | 940 | 1.01 |
| 9 | (A9) | 800 | 1.01 |
TABLE 2-2
| Synthesis Example | Compound | Mw | Mw/Mn |
|---|---|---|---|
| 10 | (A10) 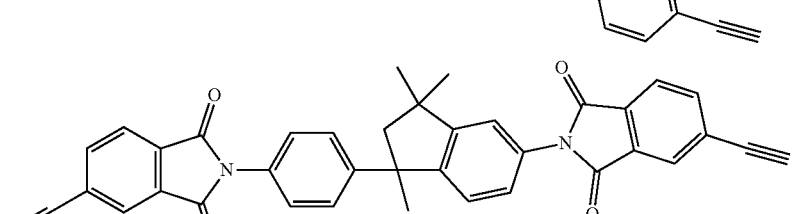 60:40 | 570 | 1.03 |

TABLE 2-2-continued
| Synthesis Example | Compound | Mw | Mw/Mn |
|---|---|---|---|
| 11 (A11) | 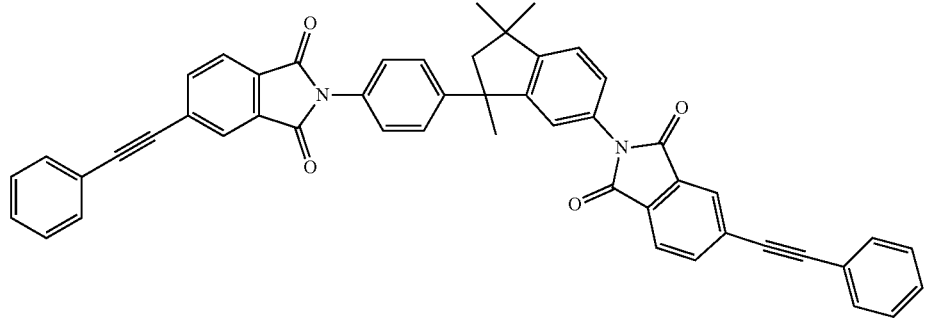 [SMILES: CC1(C)CC(C)(c2ccc(N3C(=O)c4ccc(C#Cc5ccccc5)cc4C3=O)cc2)c2cc(N3C(=O)c4ccc(C#Cc5ccccc5)cc4C3=O)ccc21] 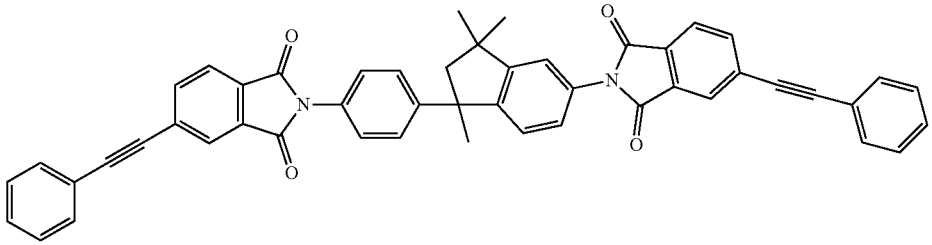 60:40 | 710 | 1.01 |
| 12 (A12) | 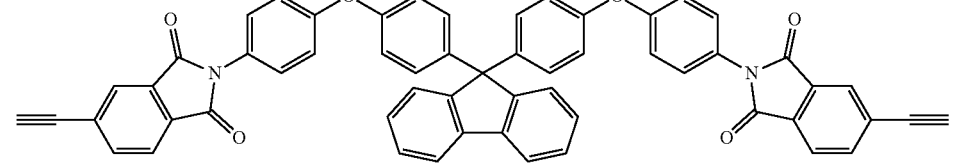 | 820 | 1.00 |
| 13 (A13) | 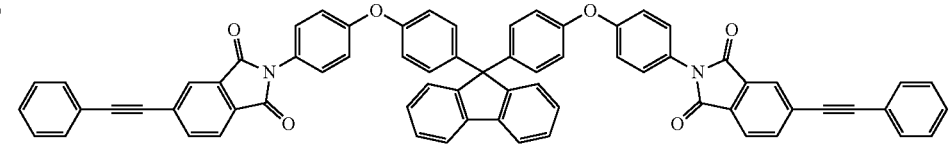 | 1100 | 1.01 |
| 14 (A14) | 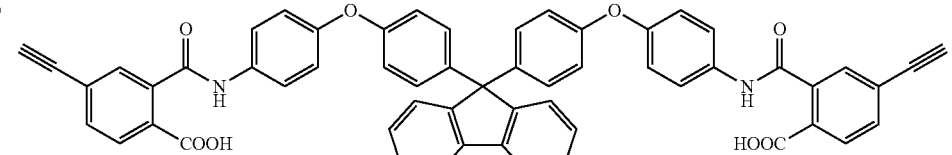 | 970 | 1.03 |
| 15 (A15) | 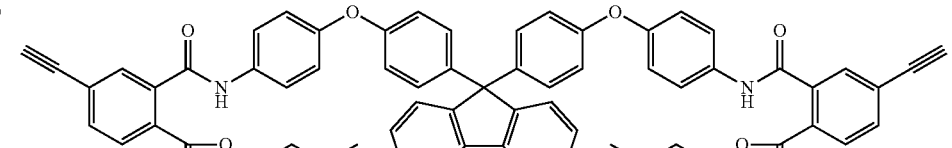 | 1090 | 1.03 |

TABLE 2-2-continued
| Synthesis Example | Compound | Mw | Mw/Mn |
|---|---|---|---|
| 16 (A16) | | 620 | 1.00 |
TABLE 2-3
| Synthesis Example | Compound | Mw | Mw/Mn |
|---|---|---|---|
| 17 (A17) | | 790 | 1.01 |
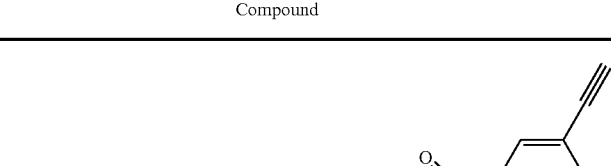

TABLE 2-3-continued

| Synthesis Example | Compound | Mw | Mw/Mn |
|---|---|---|---|
| 18 (A18) | | 940 | 1.00 |
| 19 (A19) | (A19) | 1200 | 1.01 |
| 20 (A20) | | 840 | 1.02 |

TABLE 2-4

| Synthesis Example | Compound | Mw | Mw/Mn |
|---|---|---|---|
| 21 (A21) | 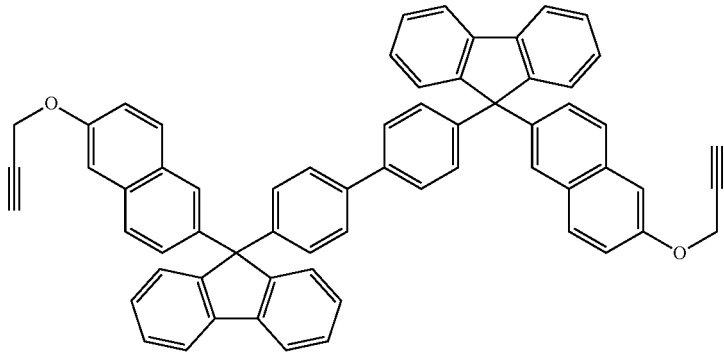 [SMILES: C#CCOc1ccc2cc(C3(c4ccc(-c5ccc(C6(c7ccc8cc(OCC#C)ccc8c7)c7ccccc7-c7ccccc76)cc5)cc4)c4ccccc4-c4ccccc43)ccc2c1] | 960 | 1.07 |
| 22 (A22) | 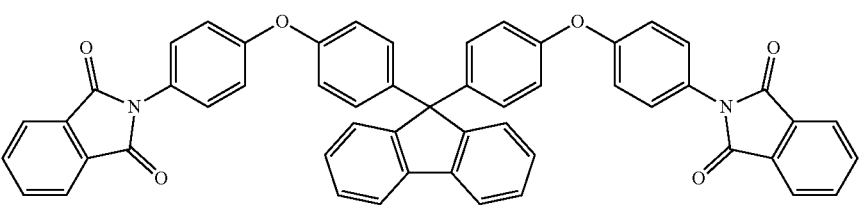 [SMILES: O=C1c2ccccc2C(=O)N1c1ccc(Oc2ccc(C3(c4ccc(Oc5ccc(N6C(=O)c7ccccc7C6=O)cc5)cc4)c4ccccc4-c4ccccc43)cc2)cc1] | 780 | 1.01 |
| 23 (A23) | 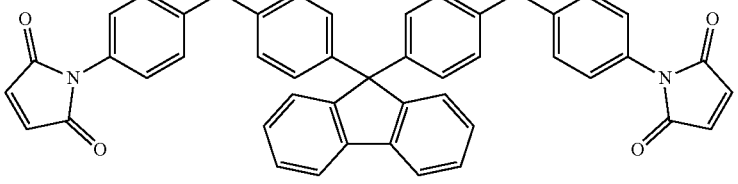 | 680 | 1.03 |
| 24 (A24) | 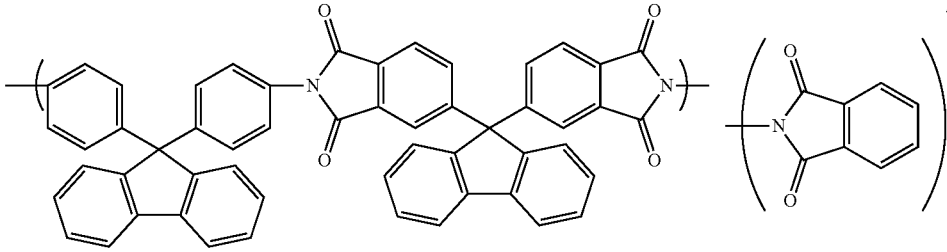 | 4500 | 1.28 |
| (D1) | 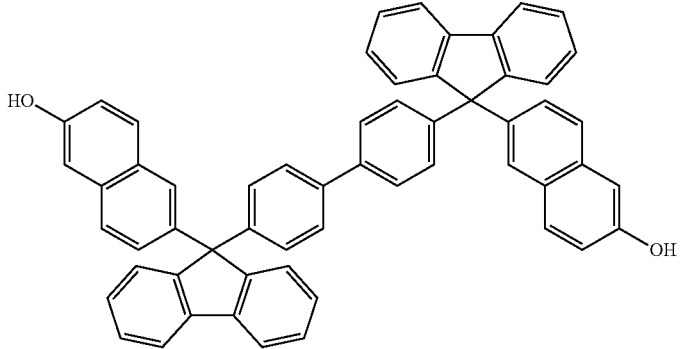 [SMILES: Oc1ccc2cc(C3(c4ccc(-c5ccc(C6(c7ccc8cc(O)ccc8c7)c7ccccc7-c7ccccc76)cc5)cc4)c4ccccc4-c4ccccc43)ccc2c1] | 860 | 1.03 |

Preparation of Organic Film Materials (UDL-1 to -25, Comparative Examples UDL-1 to -5)

The compounds (A1) to (A24) and (D1), and (S1) 1,6-diacetoxyhexane having a boiling point of 260° C., (S2) γ-butyrolactone having a boiling point of 204° C., and (S3) tripropylene glycol monomethyl ether having a boiling point of 242° C. as a high-boiling-point solvent were dissolved in a solvent containing propylene glycol monomethyl ether acetate (PGMEA) or cyclohexanone (CyHO), and 0.1 mass % FC-4430 (manufactured by Sumitomo 3M Ltd.) in proportions shown in Table 3. The solution was filtered through a 0.1-μm filter made of a fluorinated resin to prepare compositions (UDL-1 to -25, Comparative Examples UDL-1 to -5) for forming an organic film.

TABLE 3

| Composition for forming organic film | Compound (1) (part by mass) | Compound (2) (part by mass) | High-boiling-point solvent (part by mass) | CYHO (part by mass) | PGMEA (part by mass) |
|---|---|---|---|---|---|
| UDL-1 | A1 (10) | — | — | 90 | — |
| UDL-2 | A2 (10) | — | — | 90 | — |
| UDL-3 | A3 (10) | — | — | 90 | — |
| UDL-4 | A4 (10) | — | — | — | 90 |
| UDL-5 | A5 (10) | — | — | 90 | — |
| UDL-6 | A6 (10) | — | — | — | 90 |
| UDL-7 | A7 (10) | — | — | 90 | — |
| UDL-8 | A8 (10) | — | — | — | 90 |
| UDL-9 | A9 (10) | — | — | — | 90 |
| UDL-10 | A10 (10) | — | — | — | 90 |
| UDL-11 | A11 (10) | — | — | — | 90 |
| UDL-12 | A12 (10) | — | — | — | 90 |
| UDL-13 | A13 (10) | — | — | — | 90 |
| UDL-14 | A14 (10) | — | — | 90 | — |
| UDL-15 | A15 (10) | — | — | — | 90 |
| UDL-16 | A16 (10) | — | — | 90 | — |
| UDL-17 | A17 (10) | — | — | — | 90 |
| UDL-18 | A18 (10) | — | — | — | 90 |
| UDL-19 | A19 (10) | — | — | — | 90 |
| UDL-20 | A20 (10) | — | — | — | 90 |
| UDL-21 | A12 (5) | A18 (5) | — | — | 90 |
| UDL-22 | A10 (10) | — | S1 (10) | — | 80 |
| UDL-23 | A11 (10) | — | S2 (10) | — | 80 |
| UDL-24 | A12 (10) | — | S3 (10) | — | 80 |
| UDL-25 | A19 (10) | — | S2 (5) S3 (5) | — | 80 |
| Comparative Example UDL-1 | A21 (10) | — | — | — | 90 |
| Comparative Example UDL-2 | A22 (10) | — | — | — | 90 |
| Comparative Example UDL-3 | A23 (10) | — | — | — | 90 |
| Comparative Example UDL-4 | A24 (10) | — | — | 90 | — |
| Comparative Example UDL-5 | D1 (10) | — | — | — | 90 |

Example 1: Solvent Resistance Measurement (Examples 1-1 to 1-25, Comparative Examples 1-1 to 1-5)

The compositions (UDL-1 to -25, comparative UDL-1 to -5) for forming an organic film prepared above were applied onto a silicon substrate and baked at 450° C. for 60 seconds under such a nitrogen stream that the oxygen concentration was controlled to 0.2% or less. Then, the film thickness was measured. A PGMEA solvent was dispensed on the film and allowed to stand for 30 seconds. The resultant was spin dried and baked at 100° C. for 60 seconds to evaporate the PGMEA. The film thickness was measured to find a difference in the film thicknesses before and after the PGMEA treatment.

TABLE 4

| | Composition for forming organic film | Film thickness after film formation: a (Å) | Film thickness after PGMEA treatment: b (Å) | b/a × 100 (%) |
|---|---|---|---|---|
| Example 1-1 | UDL-1 | 1997 | 1992 | 99.7 |
| Example 1-2 | UDL-2 | 1987 | 1981 | 99.7 |
| Example 1-3 | UDL-3 | 1995 | 1990 | 99.7 |
| Example 1-4 | UDL-4 | 1990 | 1986 | 99.8 |
| Example 1-5 | UDL-5 | 1998 | 1987 | 99.4 |
| Example 1-6 | UDL-6 | 1997 | 1990 | 99.6 |
| Example 1-7 | UDL-7 | 2005 | 1999 | 99.7 |
| Example 1-8 | UDL-8 | 1999 | 1992 | 99.6 |
| Example 1-9 | UDL-9 | 1985 | 1980 | 99.7 |
| Example 1-10 | UDL-10 | 2009 | 2000 | 99.6 |
| Example 1-11 | UDL-11 | 1996 | 1988 | 99.6 |
| Example 1-12 | UDL-12 | 1990 | 1980 | 99.5 |
| Example 1-13 | UDL-13 | 1994 | 1990 | 99.8 |
| Example 1-14 | UDL-14 | 2011 | 2003 | 99.6 |
| Example 1-15 | UDL-15 | 1993 | 1982 | 99.4 |
| Example 1-16 | UDL-16 | 1999 | 1996 | 99.8 |
| Example 1-17 | UDL-17 | 2003 | 2000 | 99.9 |
| Example 1-18 | UDL-18 | 1994 | 1994 | 100.0 |
| Example 1-19 | UDL-19 | 2011 | 2010 | 100.0 |
| Example 1-20 | UDL-20 | 1985 | 1979 | 99.7 |
| Example 1-21 | UDL-21 | 2004 | 2002 | 99.9 |
| Example 1-22 | UDL-22 | 1994 | 1987 | 99.6 |
| Example 1-23 | UDL-23 | 1994 | 1984 | 99.5 |
| Example 1-24 | UDL-24 | 1994 | 1986 | 99.6 |
| Example 1-25 | UDL-25 | 1999 | 1999 | 100.0 |
| Comparative Example 1-1 | comparative UDL-1 | 2000 | 1981 | 99.1 |
| Comparative Example 1-2 | comparative UDL-2 | 2001 | 441 | 22.0 |
| Comparative Example 1-3 | comparative UDL-3 | 1998 | 1983 | 99.2 |
| Comparative Example 1-4 | comparative UDL-4 | 1998 | 1415 | 70.8 |
| Comparative Example 1-5 | comparative UDL-5 | 1998 | 610 | 30.5 |

As shown in Table 4, in the materials for forming an organic film of the present invention (Examples 1-1 to 1-25), the film remaining percentages after the PGMEA treatment were 99% or more. This indicates that the crosslinking reaction took place even under the nitrogen atmosphere, and sufficient solvent resistance was exhibited. In contrast, in Comparative Examples 1-2 in which an imide compound with no linking groups was used, the film remaining percentages after the PGMEA treatment were less than 50%, and sufficient solvent resistance was not exhibited. The polyimide-type Comparative Example 1-4 had a similar result. These results indicate that $R_1$, introduced as a substituent is functioning effectively as a thermal linking group.

Example 2: Heat Resistance Evaluation (Examples 2-1 to 2-25, Comparative Examples 2-1 to 2-5)

The materials (UDL-1 to -25, comparative UDL-1 to -5) for forming an organic film were each applied onto a silicon substrate and baked in the atmosphere at 180° C. for 60 seconds to form a coating film of 200 nm. The film thickness was measured. This substrate was further baked at 450° C. for further 10 minutes under such a nitrogen stream that the oxygen concentration was controlled to 0.2% or less. Then, the film thickness was measured. Table 5 shows these results.

TABLE 5

| | Composition for forming organic film | Film thickness at 180° C.: A (Å) | Film thickness at 450° C.: B(Å) | Film remaining rate % (B/A) |
|---|---|---|---|---|
| Example 2-1 | UDL-1 | 2011 | 1997 | 99.3 |
| Example 2-2 | UDL-2 | 1993 | 1981 | 99.4 |
| Example 2-3 | UDL-3 | 1995 | 1987 | 99.6 |
| Example 2-4 | UDL-4 | 1998 | 1986 | 99.4 |
| Example 2-5 | UDL-5 | 2008 | 1996 | 99.4 |
| Example 2-6 | UDL-6 | 2013 | 2001 | 99.4 |
| Example 2-7 | UDL-7 | 2013 | 2003 | 99.5 |
| Example 2-8 | UDL-8 | 1992 | 1978 | 99.3 |
| Example 2-9 | UDL-9 | 1993 | 1981 | 99.4 |
| Example 2-10 | UDL-10 | 2008 | 1992 | 99.2 |
| Example 2-11 | UDL-11 | 2006 | 1992 | 99.3 |
| Example 2-12 | UDL-12 | 2003 | 1995 | 99.6 |
| Example 2-13 | UDL-13 | 2002 | 1998 | 99.8 |
| Example 2-14 | UDL-14 | 1998 | 1970 | 98.6 |
| Example 2-15 | UDL-15 | 2002 | 1972 | 98.5 |
| Example 2-16 | UDL-16 | 1992 | 1984 | 99.6 |
| Example 2-17 | UDL-17 | 1996 | 1992 | 99.8 |
| Example 2-18 | UDL-18 | 2004 | 2002 | 99.9 |
| Example 2-19 | UDL-19 | 1995 | 1994 | 99.9 |
| Example 2-20 | UDL-20 | 1991 | 1975 | 99.2 |
| Example 2-21 | UDL-21 | 1990 | 1987 | 99.8 |
| Example 2-22 | UDL-22 | 1994 | 1984 | 99.5 |
| Example 2-23 | UDL-23 | 2003 | 1991 | 99.4 |
| Example 2-24 | UDL-24 | 1999 | 1993 | 99.7 |
| Example 2-25 | UDL-25 | 1996 | 1995 | 100.0 |
| Comparative Example 2-1 | comparative UDL-1 | 1984 | 1738 | 87.6 |
| Comparative Example 2-2 | comparative UDL-2 | 2001 | 964 | 48.2 |
| Comparative Example 2-3 | comparative UDL-3 | 1998 | 1406 | 70.3 |
| Comparative Example 2-4 | comparative UDL-4 | 1979 | 1629 | 82.3 |
| Comparative Example 2-5 | comparative UDL-5 | 1979 | 1373 | 69.4 |

As shown in Table 5, in the compositions for forming an organic film of the present invention (Examples 2-1 to 2-25), the film thicknesses were decreased by less than 2% even after the baking at 450° C. The compositions for forming an organic film of the present invention kept the film thicknesses from before the high-temperature baking even after the baking at 450° C. This indicates that the compositions for forming an organic film of the present invention have high heat resistance. In Examples 2-14 and 2-15, imide precursor compounds were used, and consequently, the film thickness decrease was slightly larger compared to compositions for forming an organic film using compounds imidized beforehand by the effect of an elimination reaction due to imidization. However, since the heat resistance after completion of the imidization is high, the film thickness decrease is suppressed to less than 2%. Compositions for forming an organic film using compounds imidized beforehand maintained a film thickness of 99% or more, indicating more excellent heat resistance. In particular, in Examples 2-16 to 2-19 in which the number of linking groups is large, film thicknesses of 99.5% or more was maintained, which indicates particularly excellent heat resistance. In contrast, compared to Comparative Example 2-2, which uses an imide compound with no linking groups, Comparative Example 2-3, which uses a bismaleimide compound, and Comparative Example 2-4, which uses a polyimide, the composition for forming an organic film of the present invention has fine films formed by the effective function of thermal linking using a terminal linking group $R_1$, indicating that a film having excellent heat resistance has been formed.

Example 3: Filling Property Evaluation (Examples 3-1 to 3-25, Comparative Examples 3-1 to 3-5)

As shown in FIG. 3, the compositions (UDL-1 to -25, comparative UDL-1 to -5) for forming an organic film were each applied onto a $SiO_2$ wafer substrate having a dense hole pattern (hole diameter: 0.16 μm, hole depth: 0.50 μm, distance between the centers of adjacent two holes: 0.32 μm) and baked with a hot plate at 450° C. for 60 seconds under such a nitrogen stream that the oxygen concentration was controlled to 0.2% or less. Thereby, an organic film 8 was formed. The substrate used was a base substrate 7 ($SiO_2$ wafer substrate) having a dense hole pattern as shown in FIG. 3 (G) (top view) and (H) (sectional view). The sectional shapes of the resulting wafer substrates were observed with a scanning electron microscope (SEM) to check whether or not the holes were filled with the organic film without voids (space). Table 6 shows the result. If an organic film material having poor filling property is used, voids occur inside the holes in this evaluation. If an organic film material having good filling property is used, the holes are filled with the organic film without voids in this evaluation as shown in FIG. 3 (I).

TABLE 6

| | Composition for forming organic film | Presence/ absence of voids |
|---|---|---|
| Example 3-1 | UDL-1 | absent |
| Example 3-2 | UDL-2 | absent |
| Example 3-3 | UDL-3 | absent |
| Example 3-4 | UDL-4 | absent |
| Example 3-5 | UDL-5 | absent |
| Example 3-6 | UDL-6 | absent |
| Example 3-7 | UDL-7 | absent |
| Example 3-8 | UDL-8 | absent |
| Example 3-9 | UDL-9 | absent |
| Example 3-10 | UDL-10 | absent |
| Example 3-11 | UDL-11 | absent |
| Example 3-12 | UDL-12 | absent |
| Example 3-13 | UDL-13 | absent |
| Example 3-14 | UDL-14 | absent |
| Example 3-15 | UDL-15 | absent |
| Example 3-16 | UDL-16 | absent |
| Example 3-17 | UDL-17 | absent |
| Example 3-18 | UDL-18 | absent |
| Example 3-19 | UDL-19 | absent |
| Example 3-20 | UDL-20 | absent |
| Example 3-21 | UDL-21 | absent |
| Example 3-22 | UDL-22 | absent |
| Example 3-23 | UDL-23 | absent |
| Example 3-24 | UDL-24 | absent |
| Example 3-25 | UDL-25 | absent |
| Comparative Example 3-1 | Comparative Example UDL-1 | present |
| Comparative Example 3-2 | Comparative Example UDL-2 | present |
| Comparative Example 3-3 | Comparative Example UDL-3 | present |
| Comparative Example 3-4 | Comparative Example UDL-4 | present |
| Comparative Example 3-5 | Comparative Example UDL-5 | present |

As shown in Table 6, the compositions for forming an organic film of the present invention (Examples 3-1 to 3-25) enabled the hole patterns to be filled without voids, confirming that the filling property was favorable. Meanwhile, in Comparative Examples 3-1 to 3-5, voids occurred, confirming that the filling property was poor. This result indicates that the composition for forming an organic film of the present invention has heat resistance ensured by thermosetting reaction and the filling property is improved. Meanwhile, in Comparative Examples 3-1 to 3-5, heat resistance was insufficient under a nitrogen atmosphere, and therefore, voids occurred, and favorable filling property was not obtained.

Example 4: Planarizing Property Evaluation
(Examples 4-1 to 4-25, Comparative Examples 4-1 to 4-3)

The compositions (UDL-1-25, comparative UDL-1, -3, and -4) for forming an organic film prepared above were each applied onto a base substrate 9 (SiO$_2$ wafer substrate) having a giant isolated trench pattern (FIG. 4 (J), trench width: 10 μm, trench depth: 0.10 μm), and baked at 450° C. for 60 seconds under such a nitrogen stream that the oxygen concentration was controlled to 0.2% or less. Then, a step (delta 10 in FIG. 4 (K)) between the trench portion and the non-trench portion of an organic film 10 was observed with an atomic force microscope (AFM) NX10 manufactured by Park systems Corp. Table 7 shows the result. In this evaluation, the smaller the step, the better the planarizing property. Note that, in this evaluation, a trench pattern having a depth of 0.10 μm was generally planarized using an organic film material having a film thickness of approximately 0.2 μm. This is a severe evaluation condition to evaluate the planarizing property. Note that in Comparative Examples UDL-2 and UDL-5, it was not possible to evaluate the planarizing property, since the film thickness decrease after baking was large.

TABLE 7

|   | Composition for forming organic film | Step (nm) |
|---|---|---|
| Example 4-1 | UDL-1 | 50 |
| Example 4-2 | UDL-2 | 45 |
| Example 4-3 | UDL-3 | 50 |
| Example 4-4 | UDL-4 | 50 |
| Example 4-5 | UDL-5 | 55 |
| Example 4-6 | UDL-6 | 45 |
| Example 4-7 | UDL-7 | 45 |
| Example 4-8 | UDL-8 | 40 |
| Example 4-9 | UDL-9 | 40 |
| Example 4-10 | UDL-10 | 30 |
| Example 4-11 | UDL-11 | 20 |
| Example 4-12 | UDL-12 | 20 |
| Example 4-13 | UDL-13 | 25 |
| Example 4-14 | UDL-14 | 45 |
| Example 4-15 | UDL-15 | 35 |
| Example 4-16 | UDL-16 | 35 |
| Example 4-17 | UDL-17 | 25 |
| Example 4-18 | UDL-18 | 15 |
| Example 4-19 | UDL-19 | 20 |
| Example 4-20 | UDL-20 | 45 |
| Example 4-21 | UDL-21 | 20 |
| Example 4-22 | UDL-22 | 25 |
| Example 4-23 | UDL-23 | 15 |
| Example 4-24 | UDL-24 | 15 |
| Example 4-25 | UDL-25 | 15 |
| Comparative Example 4-1 | comparative UDL-1 | 90 |
| Comparative Example 4-2 | comparative UDL-3 | 80 |
| Comparative Example 4-3 | comparative UDL-4 | 95 |

As shown in Table 7, in the composition for forming an organic film of the present invention (Examples 4-1 to 4-25), the organic films had smaller steps between the trench portion and the non-trench portion than those in Comparative Example 4-1 and Comparative Example 4-2, confirming that the planarizing property is excellent. In Comparative Example 4-2, film loss that occurs due to high-temperature baking is large due to poor heat resistance. Hence, the difference in the film thicknesses of the upper part of the step and the lower part of the step was emphasized. Accordingly, the planarizing property was degraded so that the result was as described above. In Comparative Example 4-3, since polyimide was used, in addition to the film loss, thermal flowability was lost due to increase in Mw, which resulted in poor planarizing property. Furthermore, comparing Examples 4-22 to 4-25 in which the high-boiling-point solvent was added with Examples 4-10 to 4-12 and 4-19 in which the high-boiling-point solvent was not added respectively, it is revealed that adding the high-boiling-point solvent further improves planarizing property.

Example 5: Patterning Test (Examples 5-1 to 5-25, Comparative Examples 5-1 to 5-3)

The compositions (UDL-1 to -25, comparative UDL-1, -3, and -4) for forming an organic film were each applied onto a silicon wafer substrate on which a SiO$_2$ film of 300 nm had been formed. Then, the resulting substrate was baked at 450° C. for 60 seconds under such a nitrogen stream that the oxygen concentration was controlled to 0.2% or less. Thereby, an organic film (resist underlayer film) was formed. A CVD-SiON hard mask was formed thereon, and further an organic antireflective film material (ARC-29A: manufactured by Nissan Chemical Industries, Ltd.) was applied and baked at 210° C. for 60 seconds to form an organic antireflective film having a film thickness of 80 nm. A monolayer resist for ArF was applied thereon as a resist upper layer film material and baked at 105° C. for 60 seconds to form a photoresist film having a film thickness of 100 nm. A liquid immersion top coat material (TC-1) was applied on the photoresist film and baked at 90° C. for 60 seconds to form a top coat having a film thickness of 50 nm. Note that in Comparative Examples UDL-2 and UDL-5, it was not possible to ensure solvent resistance, and therefore, it was not possible to proceed to the subsequent patterning test.

The resist upper layer film material (monolayer resist for ArF) was prepared by: dissolving a polymer (RP1), an acid generator (PAG1), and a basic compound (Amine1) into a solvent containing 0.1 mass % FC-430 (manufactured by Sumitomo 3M Ltd.) in proportions shown in Table 8; and filtering the solution through a 0.1-μm filter made of a fluorinated resin.

TABLE 8

|   | Polymer (part by mass) | Acid generator (part by mass) | Basic compound (part by mass) | Solvent (part by mass) |
|---|---|---|---|---|
| Mono layer resist for ArF | RP1 (100) | PAG1 (6.6) | Amine1 (0.8) | PGMEA (2500) |

The polymer (RP1), acid generator (PAG1), and basic compound (Amine1) used are shown below.

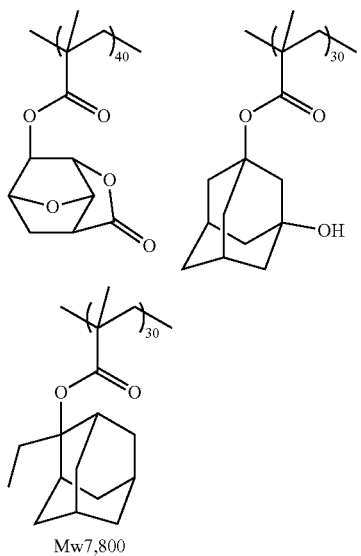

RP1

Mw7,800

PAG1

Amine1

The liquid immersion top coat material (TC-1) was prepared by: dissolving a top coat polymer (PP1) into organic solvents in proportions shown in Table 9; and filtering the solution through a 0.1-μm filter made of a fluorinated resin.

TABLE 9

| | Polymer (part by mass) | Organic solvent (part by mass) |
|---|---|---|
| TC-1 | PP1 (100) | diisoamyl ether (2700) 2-methyl-1-butanol (270) |

The polymer (PP1) used is shown below.

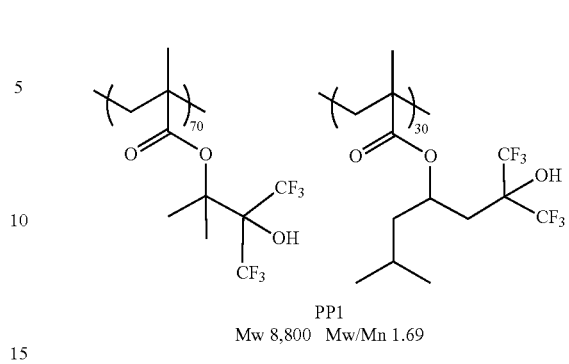

PP1
Mw 8,800  Mw/Mn 1.69

Next, the resulting substrate was exposed to light with an ArF liquid immersion exposure apparatus (NSR-S610C manufactured by Nikon Corporation, NA: 1.30, σ: 0.98/0.65, 35° s-polarized dipole illumination, 6% halftone phase shift mask), baked at 100° C. for 60 seconds (PEB), and developed with a 2.38 mass % tetramethylammonium hydroxide (TMAH) aqueous solution for 30 seconds. Thus, a 55 nm 1:1 positive line and space pattern was obtained.

Next, the organic antireflective film and the CVD-SiON hard mask were processed by dry etching using the resist pattern as a mask with an etching apparatus Telius manufactured by Tokyo Electron Limited to form a hard mask pattern. The organic film was etched using the obtained hard mask pattern as a mask to form an organic film pattern. The $SiO_2$ film was processed by etching using the obtained organic film pattern as a mask. The etching conditions were as described below.

Conditions for transferring the resist pattern to the SiON hard mask.

| | |
|---|---|
| Chamber pressure: | 10.0 Pa |
| RF power: | 1,500 W |
| $CF_4$ gas flow rate: | 75 sccm |
| $O_2$ gas flow rate: | 15 sccm |
| Time: | 15 sec |

Conditions for transferring the hard mask pattern to the organic film.

| | |
|---|---|
| Chamber pressure: | 2.0 Pa |
| RF power: | 500 W |
| Ar gas flow rate: | 75 sccm |
| $O_2$ gas flow rate: | 45 sccm |
| Time: | 120 sec |

Conditions for transferring the organic film pattern to the $SiO_2$ film.

| | |
|---|---|
| Chamber pressure: | 2.0 Pa |
| RF power: | 2,200 W |
| $C_5F_{12}$ gas flow rate: | 20 sccm |
| $C_2F_6$ gas flow rate: | 10 sccm |
| Ar gas flow rate: | 300 sccm |
| $O_2$ gas flow rate: | 60 sccm |
| Time: | 90 sec |

The pattern cross sections were observed with an electron microscope (S-4700) manufactured by Hitachi, Ltd. Table 10 shows the result.

TABLE 10

| | Composition for forming organic film | Pattern profile after etching for transferring to substrate |
|---|---|---|
| Example 5-1 | UDL-1 | vertical profile |
| Example 5-2 | UDL-2 | vertical profile |
| Example 5-3 | UDL-3 | vertical profile |
| Example 5-4 | UDL-4 | vertical profile |
| Example 5-5 | UDL-5 | vertical profile |
| Example 5-6 | UDL-6 | vertical profile |
| Example 5-7 | UDL-7 | vertical profile |
| Example 5-8 | UDL-8 | vertical profile |
| Example 5-9 | UDL-9 | vertical profile |
| Example 5-10 | UDL-10 | vertical profile |
| Example 5-11 | UDL-11 | vertical profile |
| Example 5-12 | UDL-12 | vertical profile |
| Example 5-13 | UDL-13 | vertical profile |
| Example 5-14 | UDL-14 | vertical profile |
| Example 5-15 | UDL-15 | vertical profile |
| Example 5-16 | UDL-16 | vertical profile |
| Example 5-17 | UDL-17 | vertical profile |
| Example 5-18 | UDL-18 | vertical profile |
| Example 5-19 | UDL-19 | vertical profile |
| Example 5-20 | UDL-20 | vertical profile |
| Example 5-21 | UDL-21 | vertical profile |
| Example 5-22 | UDL-22 | vertical profile |
| Example 5-23 | UDL-23 | vertical profile |
| Example 5-24 | UDL-24 | vertical profile |
| Example 5-25 | UDL-25 | vertical profile |
| Comparative Example 5-1 | comparative UDL-1 | vertical profile |
| Comparative Example 5-2 | comparative UDL-3 | vertical profile |
| Comparative Example 5-3 | comparative UDL-4 | vertical profile |

As shown in Table 10, as a result of any of the compositions for forming an organic film of the present invention (Examples 5-1 to 5-25), the resist upper layer film pattern was favorably transferred to the final substrate, confirming that the compositions for forming an organic film of the present invention are suitably used in fine processing according to the multilayer resist method. In Comparative Examples 5-1 and 5-2 the heat resistance was insufficient, but the patterns were formed. Further, in Comparative Example 5-3, solvent resistance was also insufficient, but the patterns were formed.

Example 6: Patterning Test (Examples 6-1 to 6-25, Comparative Examples 6-1 to 6-3)

Coating films were formed by the same methods as those in Example 5, except that the compositions (UDL-1 to -25, comparative UDL-1, -3, and -4) for forming an organic film prepared above were each applied onto a $SiO_2$ wafer substrate having a trench pattern (trench width: 10 μm, trench depth: 0.10 μm) and baked at 450° C. for 60 seconds under such a nitrogen stream that the oxygen concentration was controlled to 0.2% or less. Then, the coating films were subjected to patterning and dry etching, and the resulting pattern profiles were observed.

TABLE 11

| | Composition for forming organic film | Pattern profile after etching for transferring to substrate |
|---|---|---|
| Example 6-1 | UDL-1 | vertical profile |
| Example 6-2 | UDL-2 | vertical profile |
| Example 6-3 | UDL-3 | vertical profile |
| Example 6-4 | UDL-4 | vertical profile |
| Example 6-5 | UDL-5 | vertical profile |
| Example 6-6 | UDL-6 | vertical profile |
| Example 6-7 | UDL-7 | vertical profile |
| Example 6-8 | UDL-8 | vertical profile |
| Example 6-9 | UDL-9 | vertical profile |
| Example 6-10 | UDL-10 | vertical profile |
| Example 6-11 | UDL-11 | vertical profile |
| Example 6-12 | UDL-12 | vertical profile |
| Example 6-13 | UDL-13 | vertical profile |
| Example 6-14 | UDL-14 | vertical profile |
| Example 6-15 | UDL-15 | vertical profile |
| Example 6-16 | UDL-16 | vertical profile |
| Example 6-17 | UDL-17 | vertical profile |
| Example 6-18 | UDL-18 | vertical profile |
| Example 6-19 | UDL-19 | vertical profile |
| Example 6-20 | UDL-20 | vertical profile |
| Example 6-21 | UDL-21 | vertical profile |
| Example 6-22 | UDL-22 | vertical profile |
| Example 6-23 | UDL-23 | vertical profile |
| Example 6-24 | UDL-24 | vertical profile |
| Example 6-25 | UDL-25 | vertical profile |
| Comparative Example 6-1 | comparative UDL-1 | pattern collapse |
| Comparative Example 6-2 | comparative UDL-3 | pattern collapse |
| Comparative Example 6-3 | comparative UDL-4 | pattern collapse |

As shown in Table 11, as a result of any of the compositions for forming an organic film of the present invention (Examples 6-1 to 6-25), the resist upper layer film pattern was favorably transferred to the final substrate, confirming that the compositions for forming an organic film of the present invention are suitably used in fine processing according to the multilayer resist method. Meanwhile, in Comparative Examples 6-1 to 6-3, even when solvent resistance was achieved and a cured film was formed, the pattern was poorly filled. Hence, pattern collapse occurred at patterning, and favorable patterns were not obtained in the end.

From the above, it was revealed that the inventive materials for forming an organic film containing the inventive compound for forming an organic film have heat resistance to 400° C. or higher and high filling and planarizing properties even in an oxygen-free inert gas. Thus, the inventive materials for forming an organic film are quite useful as organic film materials used in multilayer resist methods. Moreover, the inventive patterning processes using these materials can precisely form a fine pattern even when a body to be processed is a stepped substrate.

It should be noted that the present invention is not restricted to the above-described embodiments. The embodiments are merely examples so that any embodiments that have substantially the same feature and demonstrate the same functions and effects as those in the technical concept as disclosed in claims of the present invention are included in the technical range of the present invention.

The invention claimed is:

1. A material for forming a resist underlayer film, comprising:

(A) a compound for forming a resist underlayer film shown by the following general formula (1A); and (B) an organic solvent,

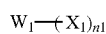  (1A)

wherein $W_1$ represents an organic group with a valency of n1, n1 represents an integer of 4, and $X_1$ represents any of groups shown by the following general formulae (1B) and (1C),

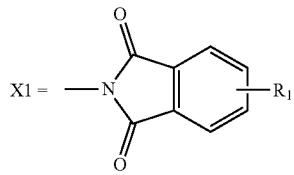  (1B)

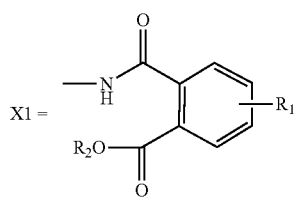  (1C)

wherein $R_1$ represents any of groups shown by the following formula (1D), and two or more kinds of $R_1$ may be used in combination; $R_2$ represents a hydrogen atom or a linear or branched, saturated or unsaturated hydrocarbon group having 1 to 20 carbon atoms, and a methylene group constituting $R_2$ may be substituted with an oxygen atom or a carbonyl group,

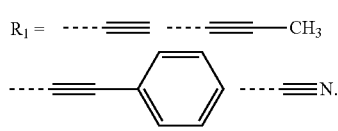  (1D)

2. The material for forming a resist underlayer film aft organic film according to claim 1, wherein the component (A) is a compound shown by the following general formula (1E),

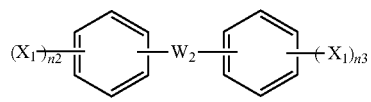  (1E)

wherein $W_2$ represents a single bond or a divalent organic group, n2 and n3 represent integers that satisfy n2+n3=4, the benzene rings in the formula optionally have a substituent thereon, and an organic group in $W_2$ and a substituent on the benzene ring optionally bond to each other to form a cyclic organic group; $X_1$ represents any of groups shown by the general formulae (1B) and (1C).

3. The material for forming a resist underlayer film according to claim 2, wherein $W_2$ in the general formula (1E) represents any of a single bond and groups shown by the following formula (1F),

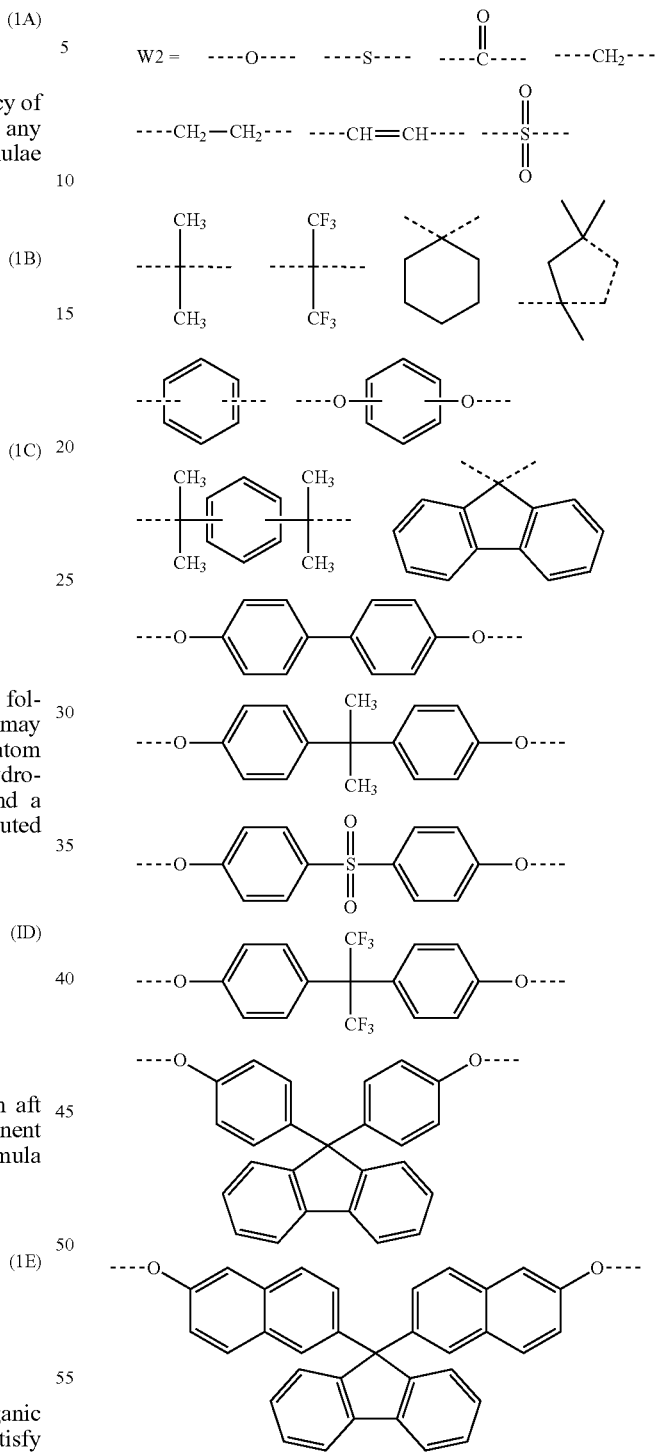  (1F)

wherein an aromatic ring in the above formula may have a substituent thereon.

4. The material for forming a resist underlayer film according to claim 2, wherein n2 and n3 in the general formula (1E) satisfy the relation n2=2, n3=2, n2+n3=4, and the $X_1$ is a group represented by the following general formula (1G),

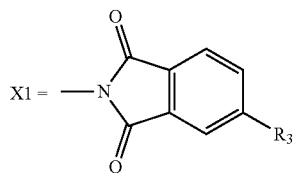

wherein, $R_3$ represents any of groups shown by the following formula (1H), and two or more kinds of $R_3$ may be used in combination.

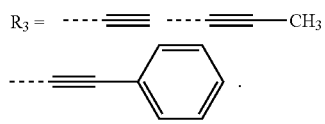

5. The material for forming a resist underlayer film according to claim 1, wherein the component (A) satisfies $1.00 \leq Mw/Mn \leq 1.10$ where Mw is a weight average molecular weight and Mn is a number average molecular weight measured by gel permeation chromatography in terms of polystyrene.

6. The material for forming a resist underlayer film according to claim 1, wherein the component (B) is a mixture of one or more kinds of organic solvent having a boiling point of lower than 180° C. and one or more kinds of organic solvent having a boiling point of 180° C. or higher.

7. The material for forming a resist underlayer film according to claim 1, further comprising at least one of (C) an acid generator, (D) a surfactant, (E) a crosslinking agent, and (F) a plasticizer.

8. A substrate for manufacturing a semiconductor device, comprising a resist underlayer film on the substrate, the resist underlayer film being formed by curing the material for forming a resist underlayer film according to claim 1.

9. A method for forming a resist underlayer film employed in a semiconductor device manufacturing process, the method comprising:
spin-coating a substrate to be processed with the material for forming a resist underlayer film according to claim 1; and
heating the substrate to be processed coated with the material for forming a resist underlayer film under an inert gas atmosphere at a temperature of 50° C. or higher to 600° C. or lower within a range of 10 seconds to 7200 seconds to obtain a cured film.

10. The method for forming a resist underlayer film according to claim 9, wherein the inert gas has an oxygen concentration of 1% or less.

11. The method for forming a resist underlayer film according to claim 9, wherein the substrate to be processed has a structure or a step with a height of 30 nm or more.

12. A method for forming a resist underlayer film employed in a semiconductor device manufacturing process, the method comprising:
spin-coating a substrate to be processed with the material for forming a resist underlayer film according to claim 1;
heating the substrate to be processed coated with the material for forming a resist underlayer film in air at a temperature of 50° C. or higher to 250° C. or lower within a range of 5 seconds to 600 seconds to form a coating film; and
then heating under an inert gas atmosphere at a temperature of 200° C. or higher to 600° C. or lower within a range of 10 seconds to 7200 seconds to obtain a cured film.

13. A patterning process comprising:
forming a resist underlayer film on a body to be processed from the material for forming a resist underlayer film according to claim 1;
forming a silicon-containing resist middle layer film on the resist underlayer film from a silicon-containing resist middle layer film material;
forming a resist upper layer film on the silicon-containing resist middle layer film from a photoresist composition;
forming a circuit pattern in the resist upper layer film;
transferring the pattern to the silicon-containing resist middle layer film by etching using the resist upper layer film having the formed pattern as a mask;
transferring the pattern to the resist underlayer film by etching using the silicon-containing resist middle layer film having the transferred pattern as a mask; and
further transferring the pattern to the body to be processed by etching using the resist underlayer film having the transferred pattern as a mask.

14. The patterning process according to claim 13, wherein the circuit pattern is formed by a lithography using light with a wavelength of 10 nm or more to 300 nm or less, a direct drawing by electron beam, a nanoimprinting, or a combination thereof.

15. The patterning process according to claim 13, wherein when the circuit pattern is formed, the circuit pattern is developed by alkaline development or development with an organic solvent.

16. The patterning process according to claim 13, wherein the body to be processed is a semiconductor device substrate or the semiconductor device substrate coated with any of a metal film, a metal carbide film, a metal oxide film, a metal nitride film, a metal oxycarbide film, and a metal oxynitride film.

17. The patterning process according to claim 16, wherein as the body to be processed, a body to be processed comprising silicon, titanium, tungsten, hafnium, zirconium, chromium, germanium, copper, silver, gold, aluminum, indium, gallium, arsenic, palladium, iron, tantalum, iridium, cobalt, manganese, molybdenum, or an alloy thereof is used.

18. A patterning process comprising:
forming a resist underlayer film on a body to be processed from the material for forming a resist underlayer film according to claim 1;
forming a silicon-containing resist middle layer film on the resist underlayer film from a silicon-containing resist middle layer film material;
forming an organic antireflective film on the silicon-containing resist middle layer film;
forming a resist upper layer film on the organic antireflective film from a photoresist composition, so that a 4-layered film structure is constructed;
forming a circuit pattern in the resist upper layer film;
transferring the pattern to the organic antireflective film and the silicon-containing resist middle layer film by etching using the resist upper layer film having the formed pattern as a mask;
transferring the pattern to the resist underlayer film by etching using the silicon-containing resist middle layer film having the transferred pattern as a mask; and further transferring the pattern to the body to be processed by etching using the resist underlayer film having the transferred pattern as a mask.

19. A patterning process comprising:
    forming a resist underlayer film on a body to be processed from the material for forming a resist underlayer film according to claim 1;
    forming an inorganic hard mask selected from a silicon oxide film, a silicon nitride film, a silicon oxynitride film, a titanium oxide film, and a titanium nitride film on the resist underlayer film;
    forming a resist upper layer film on the inorganic hard mask from a photoresist composition;
    forming a circuit pattern in the resist upper layer film;
    transferring the pattern to the inorganic hard mask by etching using the resist upper layer film having the formed pattern as a mask;
    transferring the pattern to the resist underlayer film by etching using the inorganic hard mask having the transferred pattern as a mask; and
    further transferring the pattern to the body to be processed by etching using the resist underlayer film having the transferred pattern as a mask.

20. The patterning process according to claim 19, wherein the inorganic hard mask is formed by a CVD method or an ALD method.

21. A patterning process comprising:
    forming a resist underlayer film on a body to be processed from the material for forming a resist underlayer film according to claim 1;
    forming an inorganic hard mask selected from a silicon oxide film, a silicon nitride film, a silicon oxynitride film, a titanium oxide film, and a titanium nitride film on the resist underlayer film;
    forming an organic antireflective film on the inorganic hard mask;
    forming a resist upper layer film on the organic antireflective film from a photoresist composition, so that a 4-layered film structure is constructed;
    forming a circuit pattern in the resist upper layer film;
    transferring the pattern to the organic antireflective film and the inorganic hard mask by etching using the resist upper layer film having the formed pattern as a mask;
    transferring the pattern to the resist underlayer film by etching using the inorganic hard mask having the transferred pattern as a mask; and
    further transferring the pattern to the body to be processed by etching using the resist underlayer film having the transferred pattern as a mask.

22. A compound for forming a resist underlayer film shown by the following general formula (1A),

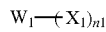
(1A)

wherein $W_1$ represents an organic group with a valency of n1, n1 represents an integer of 4, and $X_1$ represents any of groups shown by the following general formulae (1B) and (1C),

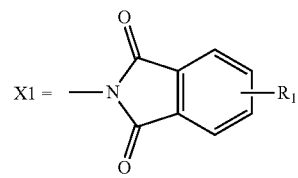
(1B)

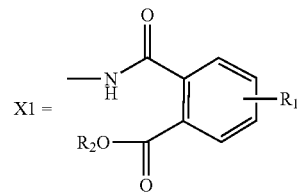
(1C)

wherein $R_1$ represents any of groups shown by the following formula (1D), and two or more kinds of $R_1$ may be used in combination; $R_2$ represents a hydrogen atom or a linear or branched, saturated or unsaturated hydrocarbon group having 1 to 20 carbon atoms, and a methylene group constituting $R_2$ may be substituted with an oxygen atom or a carbonyl group,

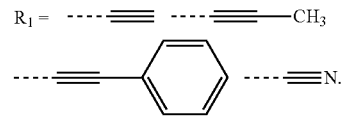
(1D)

23. The compound according to claim 22, wherein the compound for forming a resist underlayer film is shown by the following general formula (1E),

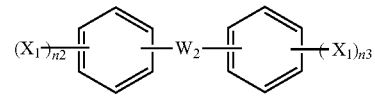
(1E)

wherein $W_2$ represents a single bond or a divalent organic group, n2 and n3 represent integers that satisfy n2+n3=4, the benzene rings in the formula optionally have a substituent thereon, and an organic group in $W_2$ and a substituent on the benzene ring optionally bond to each other to form a cyclic organic group; $X_1$ represents any of groups shown by the general formulae (1B) and (1C).

24. The compound according to claim 23, wherein $W_2$ in the general formula (1E) represents any of a single bond or groups shown by the following formula (1F),

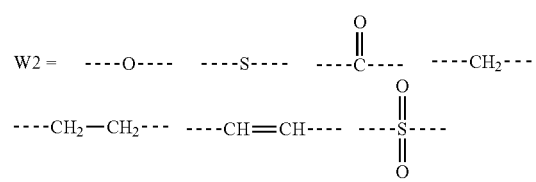
(1F)

-continued

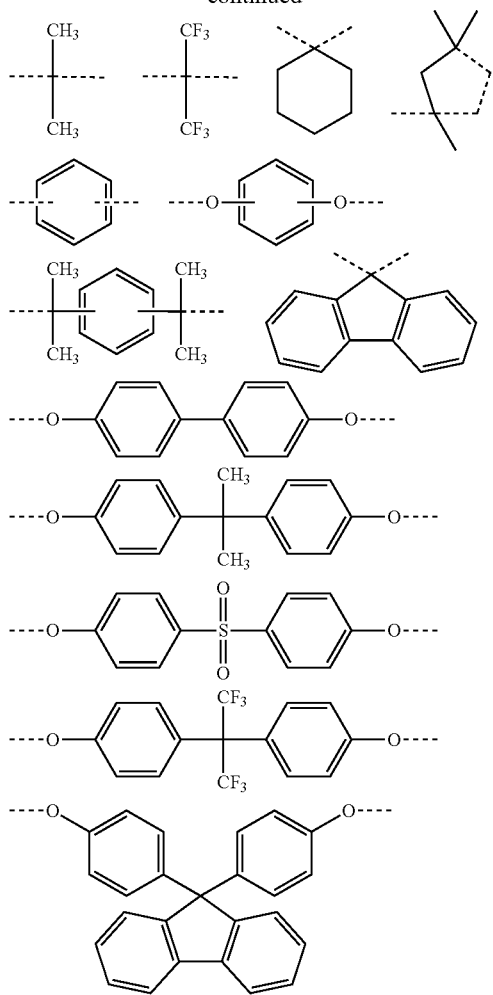

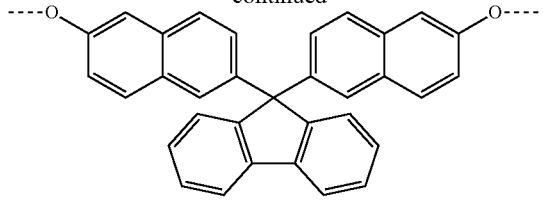

wherein an aromatic ring in the above formula may have a substituent thereon.

25. The compound according to claim 23, wherein n2 and n3 in the general formula (1E) satisfy the relation n2=2, n3=2, n2+n3=4, and the $X_1$ is a group represented by the following general formula (1G),

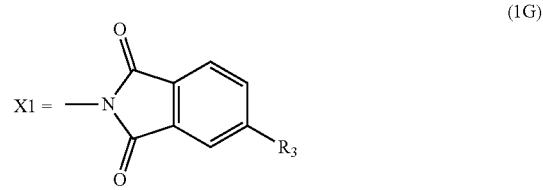

(1G)

wherein, $R_3$ represents any of groups shown by the following formula (1H), and two or more kinds of $R_3$ may be used in combination

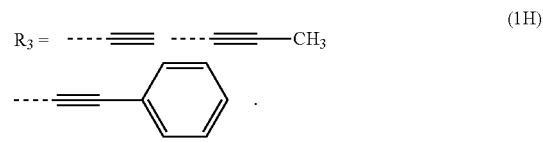

(1H)

* * * * *